US006544987B2

(12) United States Patent
Guo et al.

(10) Patent No.: US 6,544,987 B2
(45) Date of Patent: Apr. 8, 2003

(54) COMPOUNDS, COMPOSITIONS, AND METHODS FOR STIMULATING NEURONAL GROWTH AND ELONGATION

(75) Inventors: Chuangxing Guo, Encinitas, CA (US); Liming Dong, San Diego, CA (US); Xinjun J. Hou, San Diego, CA (US); Darin Vanderpool, San Diego, CA (US); Jesus Ernest Villafranca, San Diego, CA (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/726,314

(22) Filed: Dec. 1, 2000

(65) Prior Publication Data

US 2002/0061881 A1 May 23, 2002

Related U.S. Application Data

(60) Provisional application No. 06/168,246, filed on Dec. 1, 1999.

(51) Int. Cl.[7] ............... A61K 31/535; A61P 25/28; C07D 417/00; C07D 421/00
(52) U.S. Cl. ............... 514/231.5; 514/227.5; 514/227.8; 514/231.2; 514/231.5; 514/316; 514/317; 514/318; 514/319; 544/59; 544/60; 544/106; 544/111; 546/192; 546/193; 546/195
(58) Field of Search ............... 514/227.5, 227.8, 514/231.2, 231.5, 316, 317, 318, 319; 544/59, 60, 106, 111; 546/192, 193, 195

(56) References Cited

U.S. PATENT DOCUMENTS

| | | | |
|---|---|---|---|
| 5,192,773 A | 3/1993 | Armistead et al. | 514/315 |
| 5,219,851 A | 6/1993 | Hamilton et al. | 514/233.5 |
| 5,330,993 A | 7/1994 | Armistead et al. | 514/330 |
| 5,411,955 A | 5/1995 | Strasser et al. | 514/214 |
| 5,494,925 A | 2/1996 | Court et al. | 514/362 |
| 5,516,797 A | 5/1996 | Armistead et al. | 514/548 |
| 5,612,350 A | 3/1997 | Or et al. | 514/291 |
| 5,614,547 A | 3/1997 | Hamilton et al. | 514/423 |
| 5,622,970 A | 4/1997 | Armistead et al. | 514/315 |
| 5,665,774 A | 9/1997 | Armistead et al. | 514/533 |
| 5,696,135 A | 12/1997 | Steiner et al. | 514/317 |
| 5,721,256 A | 2/1998 | Hamilton et al. | 514/330 |
| 5,786,378 A | 7/1998 | Hamilton et al. | 514/423 |
| 5,798,355 A | 8/1998 | Steiner et al. | 514/248 |
| 5,801,187 A | 9/1998 | Li et al. | 514/365 |
| 5,801,197 A | 9/1998 | Steiner et al. | 514/548 |
| 5,846,979 A | 12/1998 | Hamilton et al. | 514/311 |
| 5,874,449 A | 2/1999 | Hamilton et al. | 514/330 |

FOREIGN PATENT DOCUMENTS

| | | |
|---|---|---|
| DE | 41 41 218 | 6/1993 |
| DE | 42 17 719 | 12/1993 |
| DE | 195 42 189 | 5/1997 |
| DE | 198 02 350 | 7/1998 |
| EP | 0 187 500 | 12/1985 |
| EP | 0 947 506 | 10/1999 |
| WO | WO 92/04348 | 3/1992 |
| WO | WO 96/16951 | 6/1996 |
| WO | WO 96/16970 | 6/1996 |
| WO | WO 96/40140 | 12/1996 |
| WO | WO 96/40633 | 12/1996 |
| WO | WP 96/41609 | 12/1996 |
| WO | WO 97/14439 | 4/1997 |
| WO | WO 97/18194 | 5/1997 |
| WO | WO 98/29116 | 7/1998 |
| WO | WO 98/29117 | 7/1998 |
| WO | WO 98/37882 | 9/1998 |
| WO | WO 99/45006 | 9/1999 |
| WO | WO 99/62511 | 12/1999 |
| WO | WO 00/04892 | 2/2000 |
| WO | WO 00/05232 | 2/2000 |
| WO | WO 00/32588 | 6/2000 |
| WO | WO 00/46181 | 8/2000 |
| WO | WO 00/16603 | 3/2001 |

OTHER PUBLICATIONS

US 5,654,332, 8/1997, Armistead (withdrawn)
Abdaoui, M., et al., *Phosphorus, Sulfur, and Silicon, 118*:39–47 (1996).
Abdaoui, M., et al., *Tetrahedron 56*:2427–2435 (2000).
Aouf, N., et al. *Tetrahedron Letters 32*(45):6545–6546 (1991).
Babine, R., et al., *Bioorganic & Medicinal Chemistry Letters 6*(4):385–390 (1996).
Bagshawe, *Drug Dev. Res.*, 34: 220–230 (1995).
Baumgarten, et al., *Physiol. Chem.*, *209*:145 (1932).
Bertolini, G., et al., *J. Med. Chem 40*:2011–2016 (1997).
Bodor, N., *Advances in Drug Research 13*:256–331 (1984).
Brunwin, D., et al., *J. Chem. Soc.*, pp. 1321–1327 (1973).
2, Bundgaard, H., *Design of Prodrugs*, pp. 355–360 (1985).
2, Cameron, A., et. al., *Proc. Natl. Acad. Sci. USA 92*:1784–1788 (1995).
2, Cheeseright, T., et al. *J. Chem. Soc. 1*:1953–1955 (1994).
2, Cheeseright, T., et al., *J. Chem. Soc. 1*:1595–1600 (1994).
Davies, C., et al., *Synthetic Communications, 26*(4):687–696 (1996).
DeWynter, G., et al., *Tetrahedron 52*(3):993–1004 (1996).
DeWynter, G., et al., *Tetrahedron 49*(1): 65–76 (1993).
Dragovich, P., et al., *J. Med. Chem. 42*:1213–1224 (1999).
Etzkorn, et al., *Biochemistry 33*:2380–2388 (1994).
Fischer, G., et al., *Biochimica et Biophysica Acta 43*:1101 (1984).

(List continued on next page.)

Primary Examiner—Mukund J. Shah
Assistant Examiner—Tamthom N. Truong
(74) *Attorney, Agent, or Firm*—Peter C. Richardson; Paul H. Ginsburg; Lorraine B. Ling

(57) ABSTRACT

The present invention concerns methods, pharmaceutical compounds, and compositions for stimulating neurite outgrowth in nerve cells leading to nerve regeneration. These methods, compounds and compositions inhibit rotamase enzyme activity associated with binding proteins.

15 Claims, No Drawings

OTHER PUBLICATIONS

Fischer, G., et al., *Biochimica et Biophysica Acta* 791:87–97 (1984).
Fischer, G., et al., *Nature,* 337(2):476–478 (Feb. 1998).
Flanagan, et al., *Letters to Nature* 352:803–807 (Agu. 29, 1991).
Harding, M., et al., *Nature,* 341:758–760 (Oct. 26, 1989).
Ibbett, A., et al., *Acta Cryst.,* C50:1283–1284 (1994).
International Search Report, International Appln. No. PCT/US 00/32679, Jan. 12, 2000.
Jayaraman, T., et al. *Bio., Chem.,* 267(14):9474–9477 (1992).
Kohno, H., et al., *Heterocycles,* 51(1):102–117 (1999).
Larsen, Design and Application of Prodrugs, *Drug Design and Development* (Krosgaard–Larsen et al, ed. Harwood Academic Publishers 1990).
Lee, C., et al., *J. Org. Chem.* 55:6098–6104 (1990).
Lee, C., et al., *J. Koren Chem. Soc.,* 42(2);245–247 (1998).
Lowe, G. et al, J. Chem. Soc. Perkin Trans I, (1973) p 1321–28.
Lyons, W., et al., *Proc. Natl. Acad. Sci. USA,* 91:3191–3195 (Apr. 1994).
Muller, G., et al., *J. Org. Chem.* 54:4471–4473 (1989).
Nutt, R., et al., *J. Med. Chem.* 24:692–698 (1981).
Patt, W., et al., *J. Med. Chem.* 35:2562–2572 (1992).
Reddy, K., *J. Chem. Soc.,* 1:419–420 (1985).
Regainia, Z., et al., *Tetrahedron* 56:381–387 (2000).
Shan, D., et al., *J. Pharm Sci.,* 86(7):765–767 (Jul. 1997).
Siekierka, J., et al., *Nature,* 341:755–757 (Oct. 26, 1989).
Snyder, S., et al., *Nature Medicine,* 1(1):32–37 (Jan. 1995).
Solomon et al., "Immunophilins and The Nervous System," *Nature Med.,* 1(1) 32–37 (1995).
Steinbaugh, B., et al., *Bioorganic & Medicinal Chemistry Letters,* 4(16):2029–2034 (1994).
Bagshawe, *Drug Dev. Res.,* 34: 220–230 (1995).
Brunwin, David, et al., *J. Chem. Soc. Perkin Trans. I,* pp 1321–28 (1973).
Fischer, G., et al., *Biomed., Biochim. Acta* 43(10):1101–1111 (1984).
Larsen, Design & Application of Prodrug, *Drug Design and Development*(1990)).
Snyder, S., et al., *Nature Med.,* 1(1):32–37 (1995).

COMPOUNDS, COMPOSITIONS, AND METHODS FOR STIMULATING NEURONAL GROWTH AND ELONGATION

CROSS-REFERENCED TO RELATED APPLICATION

This application claims priority from U.S. Provisional Application No. 60/168,246 filed Dec. 1, 1999.

TECHNICAL FIELD AND INDUSTRIAL APPLICABILITY OF THE INVENTION

The present invention relates to methods and pharmaceutical compounds and compositions for stimulating neurite outgrowth in nerve cells leading to nerve regeneration. For example, the compositions comprise compounds that inhibit the peptidyl-prolyl isomerase (rotamase) enzyme activity associated with the FK-506 binding proteins (FKBP), such as FKBP 12 and FKBP 52. The methods comprise treating nerve cells with compositions comprising the rotamase-inhibiting compound. The methods of the invention can be used to promote repair of neuronal damage caused by disease or physical trauma.

BACKGROUND OF THE INVENTION

Inmunophilins are a family of soluble proteins that serve as receptors for important immunosuppressant drugs such as cyclosporin A, FK-506 and rapamycin. An immunophilin of particular interest are the FK-506 binding proteins (FKBP). For a review of the role of immunophilins in the nervous system, see Solomon et al., "Immunophilins and the Nervous System," *Nature Med.*, 1(1), 32–37 (1995).

The 12-kiloDalton FK-506 binding protein, FKBP12, binds FK-506 with high affinity. Such binding has been directly measured using microcalorimetry and radiolabeled FK-506, e.g., [$^3$H]dihydro-FK-506 (see Siekierka et al., *Nature*, 341, 755–57 (1989); and U.S. Pat. No. 5,696,135 to Steiner et al.) and 32-[1-$^{14}$C]-benzoyl-FK-506 (see Harding et al., *Nature*, 341, 758–60 (1989)). Binding affinity of other compounds for FKBP can be determined directly by microcalorimetry or from competitive binding assays using either tritiated or $^{14}$C-labelled FK-506, as described by Siekierka et al. or Harding et al.

FK-506-binding protein FKBP12 participates in a variety of significant cellular functions. FKBP12 catalyzes cis-trans isomerization of peptidyl-prolyl linkages. This peptidyl-prolyl isomerase enzyme activity is also referred to as rotamase activity. Such activity is readily assayed by methods known in the art (see Fischer et al., *Biochim. Biophys. Acta* 791, 87 (1984); Fischer et al., *Biomed. Biochim. Acta* 43, 1101 (1984); and Fischer et al., *Nature* 337, 476–478 (1989)). U.S. Pat. Nos. 5,192,773 and 5,330,993 to Armistead et al. report FKBP binding affinities that were correlated with rotamase-inhibiting activities for many compounds.

FK-506 and compounds that bind FKBP competitively with FKBP stimulate outgrowth of neurites (axons) in nerve cells (see U.S. Pat. No. 5,696,135 to Steiner et al.). Lyons et al. (*Proc. Natl. Acad, Sci, USA*, 91, 3191–95 (1994)) demonstrated that FK-506 acts to enhance or potentiate the effectiveness of nerve growth factor (NGF) in stimulating neurite outgrowth in a rat pheochromocytoma cell line. The mechanism of stimulation of such neurite outgrowth appears to be 10- to 100-fold potentiation of the action of nerve growth factor.

Potency for inhibition of the peptidyl-prolyl isomerase (rotamase) enzyme activity of FKBP by FK-506, and by compounds that competitively inhibit FK-506 binding to FKBP, empirically correlates with activity for stimulation of neurite outgrowth. Because of the close correlation between rotamase inhibition and neurotrophic action, it has been proposed that the rotamase may convert a protein substrate into a form that promotes neural growth (see U.S. Pat. No. 5,696,135). For example, it has been found that FKBP12 forms bound complexes with the intracellular calcium ion channels—the ryanodine receptor (RyR) and the inositol 1,4,5-triphosphate receptor (IP$_3$R) (Jayaraman et al., *J. Biol. Chem.*, 267, 9474–9477 (1992); Cameron et al., *Proc. Natl. Acad. Sci*, USA, 92, 1784–1788 (1995)), helping to stabilize calcium release. For both the RyR and the IP$_3$R, it has been demonstrated that FK-506 and rapamycin are capable of dissociating FKBP12 from these receptors. In both cases, the "stripping" off of FKBP12 leads to increased leakiness of the calcium channels and lower intracellular calcium concentrations. It has been suggested that calcium flux may be associated with stimulation of neurite outgrowth.

In addition, FK-506—FKBP bound complexes bind to and inhibit calcineurin, a cytoplasmic phosphatase. The phosphatase activity of calcineurin is necessary for dephosphorylation and subsequent translocation into the nucleus of nuclear factor of activated T-cells (NF-AT) (see Flanagan et al., *Nature*, 352, 803–807 (1991)). NF-AT is a transcription factor that initiates interleukin-2 gene activation, which in turn mediates T-cell proliferation; these steps are important to the activation of an immune response. Calcineurin-inhibiting activity is correlated with the immunosuppressant activity of FK-506 and related compounds.

Calcineurin inhibition, however, does not correlate with the stimulation of neurite outgrowth. Therefore, compounds that are potent inhibitors of rotamase but not strong inhibitors of calcineurin are desired since they should be neurotrophic but non-immunosuppressive.

Such neurotrophic agents desirably find use in augmenting neurite outgrowth, and hence in promoting neuronal growth and regeneration in various pathological situations where neuronal repair can be facilitated, including peripheral nerve damage caused by injury or diseases such as diabetes, brain damage associated with stroke, and for the treatment of neurological disorders related to neurodegeneration, including Parkinson's disease, Alzheimer's disease, and amyotrophic lateral sclerosis (ALS).

Such neurotrophic agents should also be useful for the treatment of memory impairment, for the treatment of hair loss, for the treatment of hearing loss, and for the treatment of vision disorder. See WO 00/16603 and WO 00/32588. Further, such use is preferably without the associated effect of immunosuppression, since long-term use of immunosuppressants is associated with side effects such as kidney toxicity, neurological deficits, and vascular hypertension.

Various inhibitors of rotamase enzyme activity, FKBP-binding compounds, or immunomodulating compounds are known. See, e.g., U.S. Pat. Nos. 5,192,773; 5,330,993; 5,516,797; 5,612,350; 5,614,547; 5,622,970; 5,654,332; 5,665,774; 5,696,135; 5,721,256; 5,798,355; 5,786,378; 5,846,979; 5,801,187; 5,801,197 and 6,080,753. See also EP 947,506 and International Publication Nos. WO 96/41609, WO 96/40633, WO 96/40140, WO 98/29116, WO 98/29117, WO 97/14439, WO 98/37882, WO 99/45006, WO 00/27811, WO 00/09102, WO 00/05232, WO 00/46181 and WO 99/6251.

In view of the variety of disorders that may be treated by stimulating neurite outgrowth and the relatively few neurotropic agents having an affinity for FKBP-type immunophilins, there remains a need for additional neurotrophic agents. In particular, there is a need for those neurotropic agents that are potent inhibitors of the enzyme activity and especially of the cis-trans propyl isomerase (rotamase) activity of the FKBP-type immunophilins, particularly the immunophilin FKBP-12. Such compounds will desirably have physical and chemical properties suitable for use in pharmaceutical preparations, e.g., bioavailability, half-life, and efficient delivery to the active site. In view of the desired properties, small organic molecules are preferred over proteins. Furthermore, such compounds will not significantly inhibit the protein phosphatase calcineurin and therefore lack any significant immunosuppressive activity.

According to International Publication Nos. WO 00/46181 and WO 00/46222, binding to FKBP is not necessary for neuronal activity.

SUMMARY OF THE INVENTION

It is therefore an object of the invention to provide small-molecule neurotrophic compounds, preferably through affinity for FKBP-type immunophilins. Once bound to these proteins, the neurotrophic compounds are potent inhibitors of the enzyme activity associated with immunophilin proteins, particularly rotamase enzyme activity. An additional object is to provide inhibitor compounds of the present invention that do not exert any significant immunosuppressive activity in addition to their neurotrophic activity. It is a further object of the invention to provide effective processes for synthesizing such compounds as well as useful intermediates therefore. Another object of the invention is to provide methods for treating patients having neurological trauma or disorders as a result of, or associated with, conditions that include (but are not limited to) neuralgias, muscular dystrophy, Bell's palsy, myasthenia gravis, Parkinson's disease, Alzheimer's disease, multiple sclerosis, ALS, stroke and ischemia associated with stroke, neural parapathy, other neural degenerative diseases, motor neuron diseases, and nerve injuries including spinal cord injuries. Another object of the invention is to provide methods for treating patients with hair loss, vision disorder, memory impairment, and hearing loss.

Such objects have been achieved by the neurotrophic compounds of the present invention, which maybe used to stimulate the growth and regeneration of neurons. The administration of these compounds to individuals requiring therapeutic stimulation of neuronal growth and regeneration provides effective therapies in various pathological situations where neuronal repair can be facilitated, including peripheral nerve damage caused by injury or disease such as diabetes, brain damage associated with stroke, and for the treatment of neurological disorders related to neurodegeneration, including Parkinson's disease, Alzheimer's disease, and amyotrophic lateral sclerosis.

To achieve these and other objectives, as embodied and broadly described, in a first aspect, the present invention relates to a compound of formula (I):

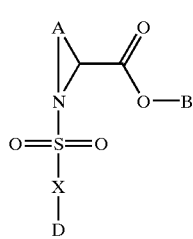

or a pharmaceutically acceptable salt, solvate, pharmaceutically acceptable prodrug or pharmaceutically active metabolite thereof, wherein:

A is $C_3$–$C_5$ alkylene optionally substituted with one or more suitable substituents and optionally any one of the $CH_2$ groups of the alkylene group may be replaced by O, S, SO or $SO_2$;

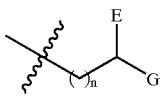

where E and G are independently Ar, H, $C_1$–$C_6$ straight or branched alkyl, $C_1$–$C_6$ straight or branched alkenyl, $C_1$–$C_6$ straight or branched alkyl or alkenyl that is substituted with a $C_5$–$C_7$ cycloalkyl, $C_1$–$C_6$ straight or branched alkyl or alkenyl that is substituted with a $C_5$–$C_7$ cycloalkenyl, or Ar substituted with $C_1$–$C_6$ straight or branched alkyl or alkenyl, wherein, in each case, one or two of the $CH_2$ groups of the alkyl or alkenyl chains may be replaced by 1–2 moieties selected from the group consisting of oxygen, sulfur, SO, $SO_2$, and

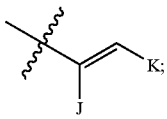

where J is H, $C_1$–$C_6$ straight or branched alkyl, or $C_1$–$C_6$ straight or branched alkenyl; and K is Ar or substituted 5–7 membered cycloalkyl with substituents at positions 3 and 4 which are independently selected from the group consisting of H, OH, —O—$(CH_2)_m$—alkyl, —O—$(CH_2)_m$-alkenyl and carbonyl, wherein m is 1–4;

where Ar is selected from the group consisting of unsubstituted and substituted phenyl, 1-napthyl, 2-naphthyl, 2-furyl, 3-furyl, 2-thienyl, 3-thienyl, 2-pyridyl, 3-pyridyl, 4-pyridyl, and monocyclic and bicyclic heterocyclic ring systems with each ring having 5 or 6 ring atoms optionally, including 1–4 heteroatoms independently selected from O, N and S; wherein when substituted, the substitutents are from one to three substituents independently selected from the group consisting of hydrogen, halo, hydroxyl, nitro, trifluoromethyl, trifluoromethoxy, $C_1$–$C_6$ straight or branched alkyl, $C_2$–$C_6$ straight or branched alkenyl, O—($C_1$–$C_4$ straight or branched alkyl), O—($C_2$–$C_4$ straight or branched alkenyl), O-benzyl, O-phenyl, 1,2-methylenedioxy, amino, carboxyl and phenyl; and n is an integer from 0 to 4;

D is $C_1$–$C_6$ straight or branched alkyl, $C_1$–$C_6$ straight or branched alkenyl, $C_5$–$C_7$ cycloalkyl, $C_5$–$C_7$ cycloalkenyl substituted with $C_1$–$C_4$ straight or branched alkyl or $C_1$–$C_4$ straight or branched alkenyl, [($C_2$–$C_4$)-alkyl or ($C_2$–$C_4$)- alkenyl)]-Ar, or Ar; and X is NR$^{10}$ or O, where R$^{10}$ is H, C$_1$–C$_4$ alkyl, or C$_1$–C$_4$ alkenyl.

In a second aspect, the invention relates to a pharmaceutical composition comprising a therapeutically effective amount of the compound of formula (I) or its pharmaceutically acceptable salt and a pharmaceutically acceptable carrier.

In a third aspect, the invention relates to a method of treating a neurological disorder in an animal, comprising administering to the animal a therapeutically effective amount of a compound of formula (I) or its pharmaceutically acceptable salt, prodrug, solvate, or its pharmaceutically active metabolite.

In a fourth aspect, the invention relates to processes of making the compounds of formula (I).

In a fifth aspect, the invention relates to a method of treating hair loss, memory impairment, or vision disorder in an animal comprising administration to the animal a therapeutically effective amount of a compound of formula (I) or its pharmaceutically acceptable salt, prodrug, solvate, or its pharmaceutically active metabolite.

In a sixth aspect, the invention relates to compounds of formula (II):

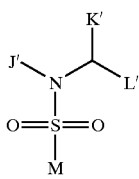

and pharmaceutically acceptable salts, prodrugs, solvates, or pharmaceutically active metabolites thereof, wherein:

J' is hydrogen, or substituted or unsubstituted alkyl;

K' is substituted or unsubstituted alkyl; or J' and K' taken together with the adjacent nitrogen atom form a heterocycle ring which may contain another heteroatom;

M is selected from the group consisting of —OR$_1$,

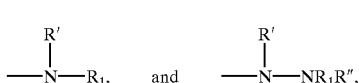

wherein:

R$^1$ is hydrogen, substituted or unsubstituted alkyl, alkenyl, aryl, cycloalkyl, heteroaryl, heterocycloalkyl, or cycloalkenyl, or C(R$^{11}$)(R$^{12}$)(R$^{13}$), wherein R$^{11}$ and R$^{12}$ each independently is substituted or unsubstituted alkyl, or R$^{11}$ and R$^{12}$ together with the atom to which they are bound form a cycloalkyl, and R$^{13}$ is H, OH, substituted or unsubstituted alkyl, aryl, heteroaryl, heterocycloalkyl, or (CH$_2$)$_n$—O—W$^1$, where n is 0, 1, 2, or 3, W$^1$ is R or C(O)R$^2$, and R$^2$ is substituted and unsubstituted alkyl;

R' is selected from the group consisting of hydrogen, substituted and unsubstituted alkyl, hydroxyl, and amino; or R$^1$ and R' taken together with the adjacent nitrogen atom form a substituted or unsubstituted heterocycle;

R" is hydrogen or substituted or unsubstituted alkyl; or

R$^1$ and R" taken together with the adjacent nitrogen atom form a substituted or unsubstituted heterocycle;

L' is

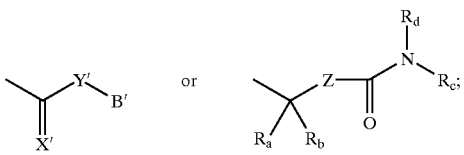

wherein X' is selected from O, S and N;
Y' is selected from O, NH, S, a direct bond, and NRf, wherein R$_f$ is substituted or unsubstituted alkyl; or
X' and Y' taken together with the adjacent carbon atom form a heterocycle ring; or
the L' NSO$_2$M moiety of formula (II) forms a 5-membered-cyclic sulfamide ring;
B' is hydrogen or

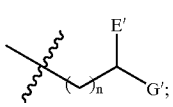

where n is an integer from 0 to 4;
E' and G' are independently H, substituted or unsubstituted alkyl, aryl, heteroaryl, heterocycloalkyl, alkenyl, cycloalkyl, or cycloalkenyl, wherein, in each case, one or two of the CH$_2$ groups of the alkyl or alkenyl chains may be replaced by 1–2 moieties selected from the group consisting of oxygen, sulfur, SO and SO$_2$, or

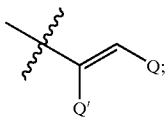

where Q' is H, or substituted or unsubstituted alkyl or alkenyl; and
Q is substituted or unsubstituted cycloalkyl, heterocycloalky, aryl, or heteroaryl;
R$_a$ and R$_b$ are independently hydrogen, substituted or unsubstituted alkyl or cycloalkyl;
Z is O, NH, CH$_2$ or NR$_e$, wherein R$_e$ is substituted or unsubstituted alkyl; and
R$_c$ and R$_d$ are independently hydrogen,

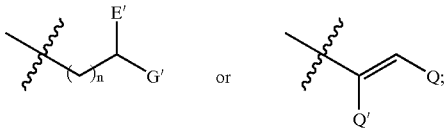

wherein E', G', Q', Q, and n are as defined above.

In a seventh aspect, the invention relates to a pharmaceutical composition comprising a therapeutically effective amount of a compound of formula (II) or its pharmaceutically acceptable salt, solvate, prodrug, or pharmaceutically active metabolite and a pharmaceutically acceptable carrier.

In an eighth aspect, the invention relates to a method of treating a neurological disorder in an animal, comprising administering to the animal a therapeutically effective amount of a compound of formula (H) or its pharmaceutically acceptable salt, solvate, prodrug, or its pharmaceutically active metabolite.

In a ninth aspect, the invention relates to processes of making the compounds of formula (II).

In a tenth aspect, the invention relates to a method of treating hair loss, memory impairment, or vision disorder in an animal comprising administration to the animal a therapeutically effective amount of a compound of formula (II) or its pharmaceutically acceptable salt, prodrug, solvate, or its pharmaceutically active metabolite.

In an eleventh aspect, the invention relates to a process of producing a compound of formula (II) comprising reacting a sulfamoyl halide and an amine in the presence of lutidine (preferably 3,5-lutidine) to produce the compound.

Other features, objects, and advantages of the invention will become apparent from the following detailed description of the invention.

DETAILED DESCRIPTION AND PREFERRED EMBODIMENTS OF THE INVENTION

As used in the present application, unless otherwise stated, the following definitions apply:

In accordance with a convention used in the art,

is used in structural formulas herein to depict the bond that is the point of attach t of the moiety or substituent to the core or backbone structure.

Where chiral carbons are included in chemical structures, unless a particular orientation is depicted, both sterioisomeric forms are intended to be encompassed.

An "alkyl group" is intended to mean a straight- or branched chain monovalent radical of saturated and/or unsaturated carbon atoms and hydrogen atoms, such as methyl (Me), ethyl (Et), propyl, isopropyl, butyl (Bu), isobutyl, t-butyl (t-Bu), ethenyl, pentenyl, butenyl, propenyl, ethynyl, butynyl, propynyl, pentynyl, hexynyl, and the like, which may be unsubstituted (i.e., containing only carbon and hydrogen) or substituted by one or more suitable substituents as defined below (e.g., one or more halogens, such as F, Cl, Br, or I, with F and Cl being preferred). A "lower alkyl group" is intended to mean an alkyl group having from 1 to 4 carbon atoms in its chain.

A "cycloalkyl group" is intended to mean a non-aromatic monovalent monocyclic, bicyclic, or tricyclic radical containing 3, 4, 5, 6, 7, 8, 9, 10, 11, 12, 13, or 14 carbon ring atoms, each of which may be saturated or unsaturated, and which may be unsubstituted or substituted by one or more suitable substituents as defined below, and to which may be fused one or more heterocycloalkyl groups, aryl groups, or heteroaryl groups, which themselves may be unsubstituted or substituted by one or more substituents. Illustrative examples of cycloalkyl groups include the following moieties:

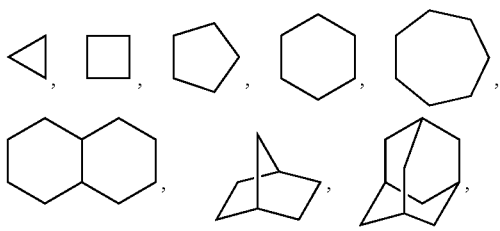

A "heterocycloalky group" is intended to mean a non-aromatic monovalent monocyclic, bicyclic, or tricyclic radical, which is saturated or unsaturated, containing 3, 4, 5, 6, 7, 8, 9, 10, 11, 12, 13, 14, 15, 16, 17, or 18 ring atoms, which includes 1, 2, 3, 4, or 5 heteroatoms selected nitrogen, oxygen, and sulfur, where the radical is unsubstituted or substituted by one or more suitable substituents as defined below, and to which may be fused one or more cycloalkyl groups, aryl groups, or heteroaryl groups, which themselves may be unsubstituted or substituted by one or more suitable substituents. Illustrative examples of heterocycloalkyl groups include the following moieties:

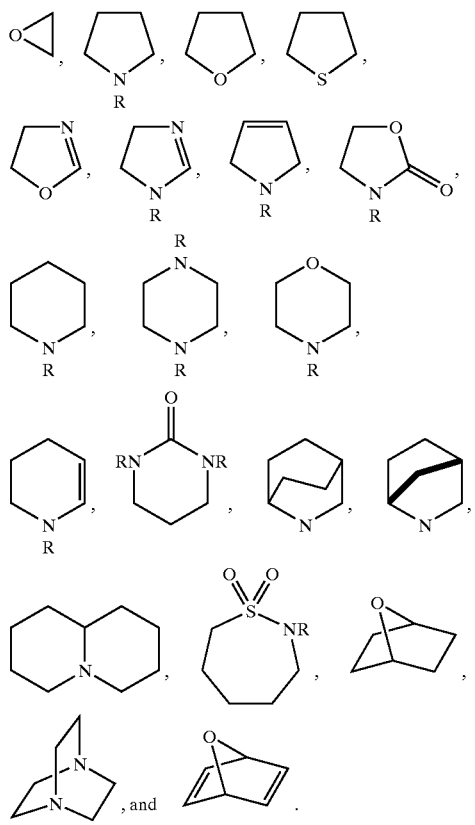

An "aryl group" is intended to mean an aromatic monovalent monocyclic, bicyclic, or tricyclic radical containing 6, 10, 14, or 18 carbon ring atoms, which may be unsubstituted or substituted by one or more suitable substituents as defined below, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Illustrative examples of aryl groups include the following moieties:

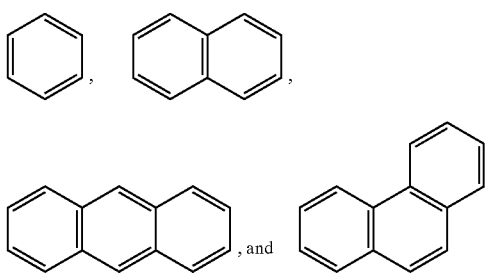

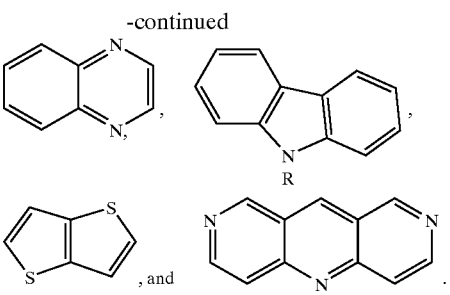

A "heteroaryl group" is intended to mean an aromatic monovalent monocyclic, bicyclic, or tricyclic radical containing 4, 5, 6, 7, 8, 9, 10, 11, 12, 13, 14, 15, 16, 17, or 18 ring atoms, including 1, 2, 3, 4, or 5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Illustrative examples of heteroaryl groups include the following moieties:

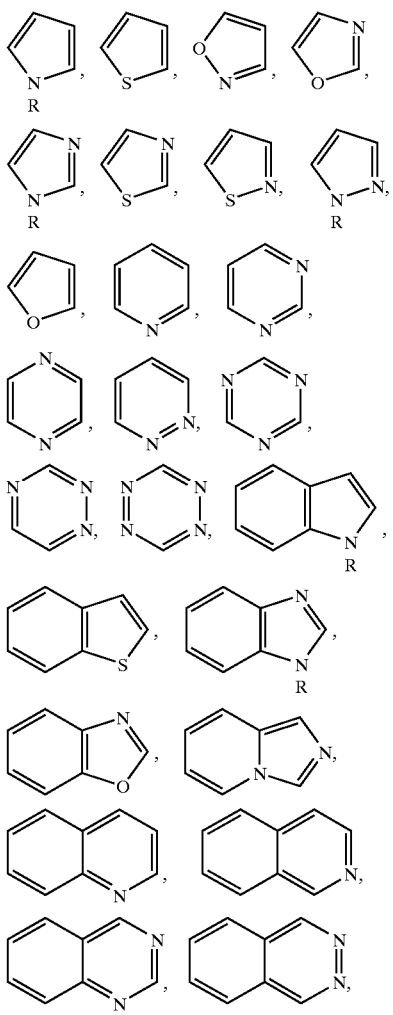

A "heterocycle" is intended to mean a heteroaryl or heterocycloalkyl group (each of which, as defined above, are optionally substituted).

An "acyl group" is intended to mean a —C(O)—R radical, where R is a substituent as defined below.

A "thioacyl group" is intended to mean a —C(S)—R radical, where R is a substituent as defined below.

A "sulfonyl group" is intended to mean a —SO$_2$R radical, where R is a substituent as defined below.

A "hydroxy group" is intended to mean the radical —OH.

An "amino group" is intended to mean the radical —NH$_2$.

An "alkylamino group" is intended to mean the radical —NHR$_a$, where R$_a$ is an alkyl group.

A "dialkylamino group" is intended to mean the radical —NR$_a$R$_b$, where R$_a$ and R$_b$ are each independently an alkyl group.

An "alkoxy group" is intended to mean the radical —OR$_a$, where R$_a$ is an alkyl group. Exemplary alkoxy groups include methoxy, ethoxy, propoxy, and the like.

An "alkoxycarbonyl group" is intended to mean the radical —C(O)OR$_a$, where R$_a$ is an alkyl group.

An "alkylsulfonyl group" is intended to mean the radical —SO$_2$R$_a$, where R$_a$ is an alkyl group.

An "alkylaminocarbonyl group" is intended to mean the radical —C(O)NHR$_a$, where R$_a$ is an alkyl group.

A "dialkylaminocarbonyl group" is intended to mean the radical —C(O)NR$_a$R$_b$, where R$_a$ and R$_b$ are each independently an alkyl group.

A "mercapto group" is intended to mean the radical —SH.

An "alkylthio group" is intended to mean the radical —SR$_a$, where R$_a$ is an alkyl group.

A "carboxy group" is intended to mean the radical —C(O)OH.

A "carbamoyl group" is intended to mean the radical —C(O)NH$_2$.

An "aryloxy group" is intended to mean the radical —OR$_c$, where R$_c$ is an aryl group.

A "heteroaryloxy group" is intended to mean the radical —OR$_d$, where R$_d$ is a heteroaryl group.

An "arylthio group" is intended to mean the radical —SR$_c$, where R$_c$ is an aryl group.

A "heteroarylthio group" is intended to mean the radical —SR$_d$, where R$_d$ is a heteroaryl group.

The term "suitable organic moiety" is intended to mean any organic moiety recognizable, such as by routine testing, to those skilled in the art as not adversely affecting the inhibitory activity of the inventive compounds. Illustrative examples of suitable organic moieties include, but are not limited to, hydroxyl groups, alkyl groups, oxo groups, cycloalkyl groups, heterocycloalkyl groups, aryl groups, heteroaryl groups, acyl groups, sulfonyl groups, mercapto groups, alkylthio groups, alkoxy groups, carboxy groups, amino groups, alkylamino groups, dialkylamino groups, carbamoyl groups, arylthio groups, heteroarylthio groups, and the like.

The term "substituent" or "suitable substituent" is intended to mean any suitable substituent that may be recognized or selected, such as through routine testing, by those skilled in the art. Illustrative examples of suitable substituents include hydroxy groups, halogens, oxo groups, alkyl groups, acyl groups, sulfonyl groups, mercapto groups, alkylthio groups, alkyloxy groups, cycloalkyl groups, heterocycloalkyl groups, aryl groups, heteroaryl groups, carboxy groups, amino groups, alkylamino groups, dialkylamino groups, carbamoyl groups, aryloxy groups, heteroaryloxy groups, arylthio groups, heteroarylthio groups, and the like.

The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

A "prodrug" is intended to mean a compound that is converted under physiological conditions or by solvolysis or metabolically to a specified compound that is pharmaceutically active.

A "pharmaceutically active metabolite" is intended to mean a pharmacologically active product produced through metabolism in the body of a specified compound.

Prodrugs and active metabolites of compounds of the formula I, or II may be identified using routine techniques known in the art. See, e.g., Bertolini et al., *J. Med. Chem.*, 40, 2011–2016 (1997); Shan, et al., *J. Pharm. Sci.*, 86 (7), 765–767; Bagshawe, *Drug Dev. Res.*, 34, 220–230 (1995); Bodor, *Advances in Drug Res.*, 13, 224–331 (1984); Bundgaard, *Design of Prodrugs* (Elsevier Press 1985); and Larsen, *Design and Application of Prodrugs*, Drug Design and Development (Krogsgaard-Larsen et al., eds., Harwood Academic Publishers, 1991).

A "solvate" is intended to mean a pharmaceutically acceptable solvate form of a specified compound that retains the biological effectiveness of such compound. Examples of solvates include compounds of the invention in combination with water, isopropanol, ethanol, methanol, dimethyl sulfoxide, ethyl acetate, acetic acid, or ethanolamine.

A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophaosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1, 4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phylacetates, phenylpropionates, phylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If the neurotrophic compound of formula I or II is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as apsartic acid or glutamic acid; aromatic acid, such as benzoic acid or cinnamic acid; sulfonic acid, such as p-toluenesulfonic acid or ethanesulfonic acid; or the like.

If the neurotrophic compound of formula I or II is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that they may exist in different crystal forms, all of which are intended to be within the scope of the present invention and specified formulas.

The neurotrophic compounds of formula I, and II and the intermediates used in the process of the present invention, may exist as single stereoisomers, racemates, and/or mixtures of enantiometers and/or diastereomers. All such single stereoisomers, racemates, and mixtures thereof are intended to be within the broad scope of the nonstereospecific structural formulae. Preferably, however, the compounds of formula I and II and the intermediate compounds used in the process of the present invention are used in optically pure form.

As generally understood by those skilled in the art, an optically pure compound is one that is enantiomerically pure. As used herein, the term "optically pure" is intended to mean a compound comprising at least a sufficient amount of a single enantiomer to yield a compound having the desired pharmacological activity. Preferably, "optically pure" is intended to mean a compound that comprises at least 90% of a single isomer (80% enantiomeric excess (e.e.)), more preferably at least 95% (90% e.e.), even more preferably at least 97.5% (95% e.e.), and most preferably at least 99% (98% e.e.). Preferably, the neurotrophic compounds of the present invention are optically pure.

Neurotrophic compounds of the invention are represented by the formula (I) and (II) defined above. Preferably, the neurotrophic compounds inhibit the rotamase (peptidyl-prolyl isomerase) enzyme activity of FKBP, in particular, FKBP12. In addition to compounds of the formula (I) and (II), neurotrophic compounds of the invention include pharmaceutically acceptable derivatives of such compounds, such as prodrugs, pharmaceutically active metabolites, and pharmaceutically acceptable salts and solvates thereof.

Particularly preferred are compounds of the formula (I'):

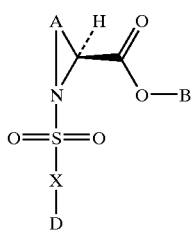
(I')

wherein A, B, D, E and X are as previously defined for the compound of formula (I).

Preferably, A is an unbranched $C_3$–$C_5$ alkylene group wherein any one of the $CH_2$ groups of the alkylene group is optionally substituted by S. More preferably, A is an unbranched unsubstituted $C_3$ or $C_4$ alkylene group (i.e., 1,3-propylene or 1,4-butylene). Even more preferably, A is $C_4$ alkylene.

Preferably, B is

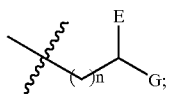

wherein E is selected from the group consisting of H, benzyl, 3-pyridyl, 2-phenylethyl and 3-phenylpropyl; G is selected from the group consisting of phenyl, 3-pyridyl, 3-phenylpropyl, 3-phenoxyphenyl and 4-phenoxyphenyl; and n is 0–4. More preferably B is selected from the group consisting of:

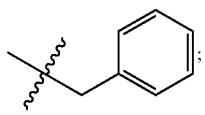

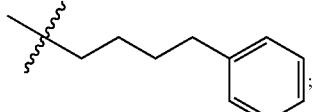

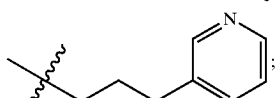

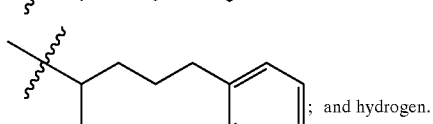; and hydrogen.

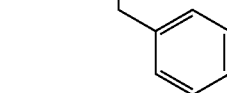

Preferably, D is selected from the group consisting of phenyl, 4-methylphenyl, 4-methoxyphenyl, 2-thienyl, 2,4,6-triisopropylphenyl, 4-fluorophenyl, 3-methoxyphenyl, 2-methoxyphenyl, 3,5-dimethoxyphenyl, 3,4,5-trimethoxyphenyl, methyl, 1-naphthyl, 8-quinolyl, 1-(5-N,N-dimethylamino)-naphthyl, 4-iodophenyl, 2,4,6-trimethylphenyl, benzyl, 4-nitrophenyl, 2-nitrophenyl, 4-chlorophenyl, 1,1-dimethylpropyl and E-styrenyl. Even more preferably D is selected from the group consisting of phenyl, 1,1-dimethylpropyl and 3,4,5-trimethoxyphenyl.

Preferably, X is NH or O.

Especially preferred species of compounds represented by the above formula (I) are the following:

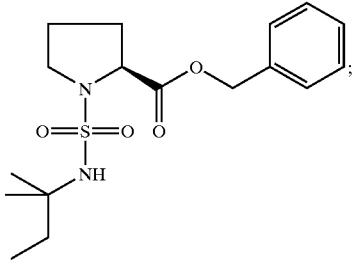;

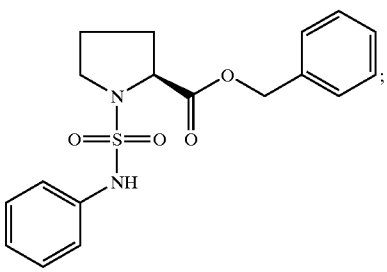;

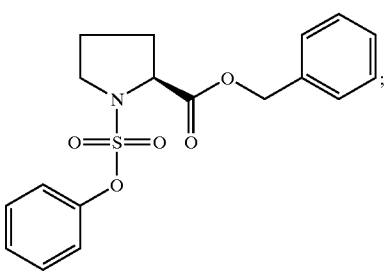;

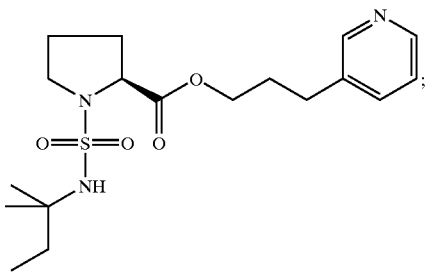;

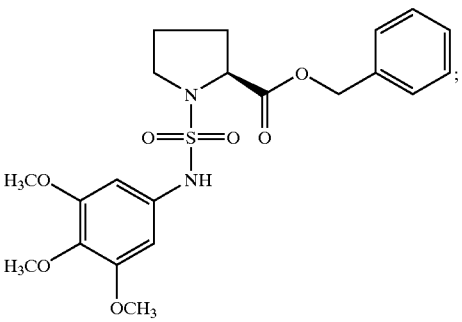;

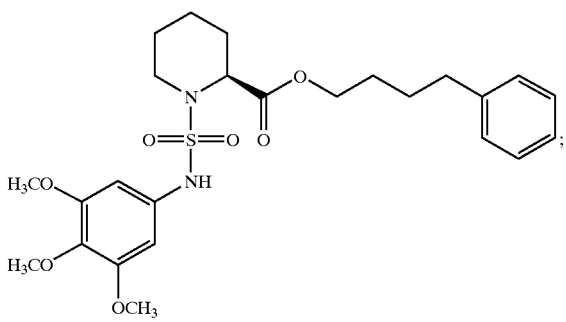

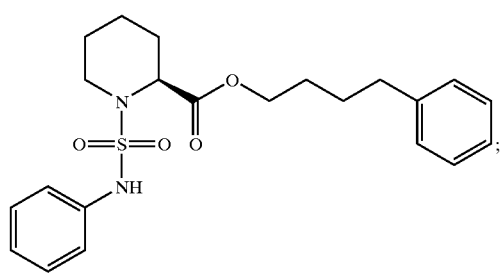

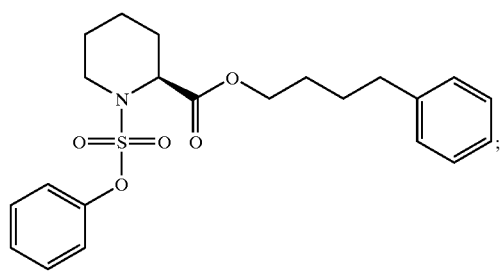

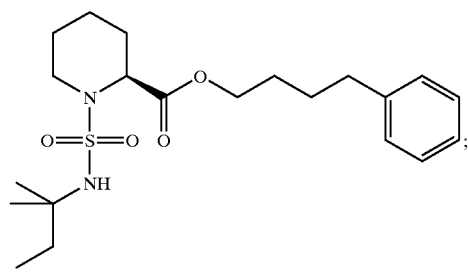

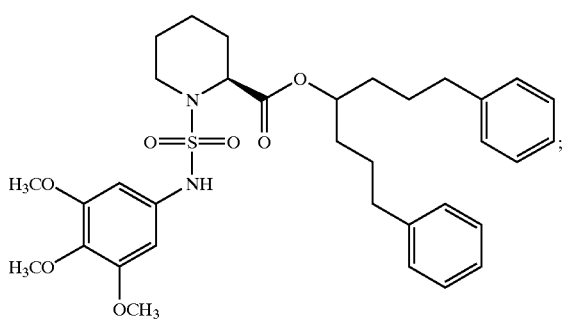

and

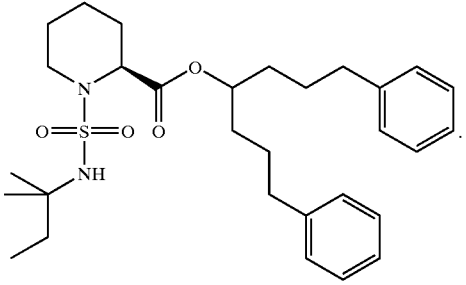

Especially preferred moieties for the variables of formula (II) are presented below and in the following examples.

Preferred examples of J' are hydrogen, ($C_1$–$C_5$) alkyl which can be substituted with substituted or unsubstituted aryl, such as phenyl or halogenated phenyl.

Preferred examples of K' are ($C_1$–$C_5$) alkyl which can be substituted with substituted or unsubstituted aryl, such as phenyl or halogenated phenyl;

Alternatively, J' and K' taken together with the adjacent nitrogen atom form a 5–7 membered heterocycle ring which may contain another heteroatom such as S, and O, and moieties selected from $SO_2$, and NR, wherein R is selected from hydrogen, and substituted or unsubstituted alkyl, aryl and heteroaryl; or J' and K' taken together with the adjacent nitrogen atom form azo-bicyclo[2.2.1] heptane or azo-bicyclo[2.2.2] octane optionally substituted with substituted or unsubstituted alkyl or aryl or one or more halogens;

In preferred embodiments, $R_1$ is $C_4$–$C_6$ cycloalkenyl, hydroxy, halogen, hydroxyl, $NO_2$, $CF_3$, $C_1$–$C_6$ alkyl, $C_2$–$C_6$ alkenyl, $C_4$ alkenyloxy, benzyloxy, phenoxy, amino, phenyl, or $C_1$–$C_4$ alkyloxy. $R^{11}$ and $R^{12}$ can each independently be $C_1$–$C_6$ alkyl. $R^{13}$ R can be $C_1$–$C_6$, or $(CH_2)_n$—O—$W^1$, where n is 0, 1, 2, or 3, $W^1$ is $R^2$ or $C(O)R^2$, and $R^2$ is $C_1$–$C_3$ alkyl optionally substituted with, for example, one or two methoxy groups.

A preferred R' group is ($C_1$–$C_5$) alkyl. Alternatively, RI and R' taken together with an adjacent nitrogen atom can form a substituted or unsubstituted heterocycle, which can be saturated or unsaturated or aromatic and can be substituted with, e.g., $C_1$–$C_4$ alkyl, hydroxy or halogen;

Preferred examples of R" are hydrogen or substituted or unsubstituted ($C_1$–$C_5$) alkyl. Alternatively, $R_1$ and R" taken together with an adjacent nitrogen form a substituted or unsubstituted heterocycle, which can be saturated or unsaturated or aromatic and can be substituted with, e.g., ($C_1$–$C_4$) alkyl, hydroxy or halogen.

Preferred examples of Y' are a direct bond or $NR_f$, wherein $R_f$ is ($C_1$–$C_5$) alkyl which may be substituted with, e.g., phenyl or halogenated phenyl.

Preferred examples of E' and G' are $C_1$–$C_6$ straight or branched alkyl, $C_1$–$C_6$ straight or branched alkenyl, $C_1$–$C_6$ straight or branched alkyl or alkenyl that is substituted with a $C_5$–$C_7$ cycloalkyl, $C_1$–$C_6$ straight or branched alkyl or alkenyl that is substituted with a $C_5$–$C_7$ cycloalkenyl, or heterocycle substituted with $C_1$–$C_6$ straight or branched alkyl or alkenyl.

Preferred examples of Q' are $C_1$–$C_6$ straight or branched alkyl or $C_1$–$C_6$ straight or branched alkenyl.

Preferred examples of Q are substituted 5–7 membered cycloalkyl with substituents at positions 3 and 4 which are independently selected from H, OH, —O—$(CH_2)_m$-alkyl, —O—$(CH_2)_m$-alkenyl and carbonyl, wherein m is 1–4.

Preferred examples of useful aryl and heteroaryl groups for the compounds of formula (II), such as for E', G', and Q, are phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S. The aryl and heteroaryl groups may contain one to three substituents independently selected from hydrogen, halo, hydroxyl, nitro, trifluoromethyl, trifluoromethoxy, $C_1$–$C_6$ straight and branched alkyl, $C_2$–$C_6$ straight and branched alkenyl, O—($C_1$–$C_4$ straight and branched alkyl), O—($C_2$–$C_4$ straight and branched alkenyl), O-benzyl, O-phenyl, 1,2-methylenedioxy, amino, carboxyl and phenyl;

Preferred examples of $R_a$ and $R_b$ are ($C_1$–$C_5$) alkyl with or without, for example, aryl substitution, or ($C_3$–$C_7$) cycloalkyl.

Preferred example of Z is NRe, wherein $R_e$ is ($C_1$–$C_4$) alkyl which may be substituted with phenyl or halogenated phenyl.

The compounds of the invention also include pharmaceutically acceptable derivatives of compounds of the formula (I) and (II). A "pharmaceutically acceptable derivative" denotes a prodrug, pharmaceutically active metabolite, or pharmaceutically acceptable salt, ester, salt of such ester, or hydrate of a compound of this invention. Such compounds, when administered to a patient, are capable of directly or indirectly yielding a compound of this invention, or a metabolic residue or product thereof, and thereby inhibit FKBP rotamase activity or promote or augment neurite outgrowth.

The compounds of formula (I) and (II) as well as metabolites thereof may be used in pharmaceutical compositions in the form of pharmaceutically acceptable salts. Such salts are preferably derived from inorganic or organic acids and bases. Exemplary acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate. Exemplary base salts include ammonium salts, alkali metal salts, such as sodium and potassium salts, alkaline earth metal salts, such as calcium and magnesium salts, salts with organic bases, such as dicyclohexylamine salts, N-methyl-D-glucosamine salt, and salts with amino acids such as arginine and lysine. Also, the basic nitrogen-containing groups can be quaternized with such agents as: lower alkyl halides, such as methyl, ethyl, propyl, and butyl chlorides, bromides or iodides; dialkyl sulfates, such as dimethyl, diethyl, dibutyl, and diamyl sulfates; long-chain halides such as decyl, lauryl, myristyl and stearyl chlorides, bromides, and iodides; and aralkyl halides, such as benzyl and phenethyl bromides. Water- or oil-soluble or dispersible products may be prepared from such salts.

In addition, the compounds of the invention may be modified by appending appropriate functionalities to enhance selective biological properties. Such modifications, which are within the purview of the ordinarily skilled artisan, include those increasing biological penetration into a given biological system (e.g., blood, lymphatic system, central nervous system), increasing oral availability, increasing solubility to allow administration by injection, altering metabolism, and altering rate of excretion.

Some of the compounds described herein contain one or more centers of asymmetry and may thus give rise to enantiomers, diastereoisomers, rotamers, and other stereoisomeric forms. The present invention is meant to include all such possible stereoisomers as well as their racemic and optically pure forms. Optically active (R) and (S) isomers may be prepared using chiral synthons or chiral reagents, or resolved using conventional techniques. When the compounds described herein contain olefinic double bonds, they are intended to include both E and Z geometric isomers.

Moreover, the chemical formulae referred to herein may exhibit the phenomenon of tautomerism. As the formulae drawings within this specification can only represent one of the possible tautomeric forms, it should be understood that the invention encompasses any tautomeric form that can be generated by employing the tools disclosed or in a known manner, and is not limited to any one tautomeric form depicted by the formulae.

EXAMPLES

The following examples are illustrative of the present invention and are not intended to be limitations thereon. Unless otherwise specified, all percentages are based on 100% by weight of the final compound.

Abbreviations that are used in the description of the invention include the following: EDC is 1-(3-dimethylaminopropyl)-3-ethylcarbodiimide hydrochloride; DCC is 1,3-Dicyclohexylcarbodiimide; DMAP is 4-dimethylaminopyridine; DMF is N,N-dimethylformamide; HATU is O-(7-azabenzotriazol-1-yl)-N,N,N',N'-tetramethyluronium hexafluorophosphate; HRMS is high resolution mass spectrum; DEAD is diethyl azodicarboxylate; MS is mass spectrum; THF is tetrahydrofuran; DIEA is diisopropylethylamine; HOBt is 1-hydroxybenzotiazole hydrate; Pd—C is palladium on carbon; atm is (atmosphere); and MOPS is (4-morpholinepropanesulfonic acid, sodium salt).

The compounds of the present invention may be readily prepared by standard techniques of organic chemistry, utilizing the general synthetic pathways depicted below. Unless otherwise indicated, the starting materials are either commercially available or can be prepared by conventional techniques. The oxy sulfonyl compounds of the present invention may be prepared in the manner depicted in Scheme 1 below. As described in Scheme 1, amino acids 1 protected by suitable blocking groups P on the amino acid nitrogen may be reacted with alcohols B'OH to generate esters 2. After removal of the protecting group, the free amine may be reacted with chlorosulfonic acid followed by phosphorous pentachloride to provide the chlorosulfonyl 4. The chlorosulfonyl 4 may then be reacted with various alcohols D'OH to provide a final product 5. Depending on the structure of the final product being synthesized, it may prove to be more efficient to prepare a compound of formula 5, and then substitute the B' group with a B" group. This may be carried out as depicted in Scheme 1, wherein the product 5 is hydrolyzed to the corresponding alcohols 6 which may then be reacted with alcohols B"OH to provide final products Scheme 1

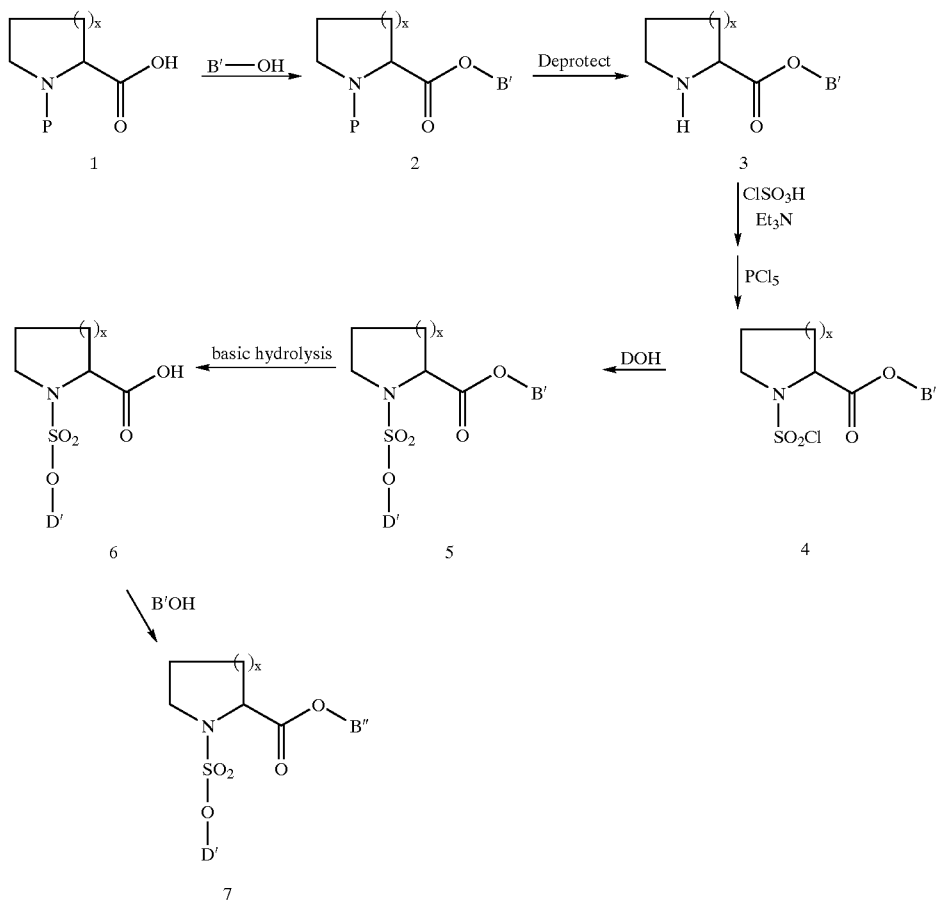

In the compounds depicted above in Scheme 1, B' and B" are independently:

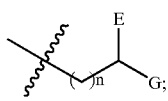

wherein E and independently Ar, H, $C_1$–$C_6$ straight or branched alkyl, $C_1$–$C_6$ straight or branched alkenyl, $C_1$–$C_6$ straight or branched alkyl or alkenyl that is substituted with a $C_5$–$C_7$ cycloalkyl, $C_1$–$C_6$ straight or branched alkyl or alkenyl that is substituted with a $C_5$–$C_7$ cycloalkenyl, or Ar substituted $C_1$–$C_6$ straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

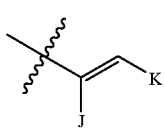

provided that both B' or B" and D' are not H; J is H, $C_1$–$C_6$ straight or branched alkyl or $C_1$–$C_6$ straight or branched alkenyl;

K is Ar or substituted 5–7 membered cycloalkyl with substituents at positions 3 and 4 which are independently selected from the group consisting of H, OH, —O—$(CH_2)_m$-alkyl, —O—$(CH_2)_m$-alkenyl and carbonyl, wherein m is 1–4;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, $C_1$–$C_6$ straight or branched alkyl, $C_2$–$C_6$ straight or branched alkenyl, O—($C_1$–$C_4$ straight or branched alkyl), O—($C_2$–$C_4$ straight or branched alkenyl), O-benzyl, O-phenyl, 1,2-methylenedioxy, amino, carboxyl and phenyl;

n is 0 to 4;

D' is $C_1$–$C_6$ straight or branched alkyl, $C_1$–$C_6$ straight or branched alkenyl, $C_5$–$C_7$ cycloalkyl, $C_5$–$C_7$ cycloalkenyl substituted with $C_1$–$C_4$ straight or branched alkyl or $C_1$–$C_4$ straight or branched alkenyl, [($C_2$–$C_4$)-alkyl or ($C_2$–$C_4$)-alkenyl)]-Ar or Ar; and x is 0–1.

The following compounds were prepared according to the general Scheme 1 depicted above:

Example 1

Synthesis of 1-Phenoxy sulfonyl-piperidine-2S-carboxylic acid 4-phenyl-butyl ester (Compound 13)

Step 1: Synthesis of piperidine-1,2S-dicarboxylic acid 1-tert-butyl ester 2S-methyl ester (compound 8):

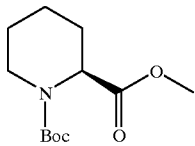

Compound 8 was prepared from racemic pipecolic acid via the published procedures. See R. F. Nutt et al., J. Med. Chem., 24, pp. 692–698 (1981) and C. E. Davies et al., Synth. Comm., 26 (4), pp. 687–696 (1996). These references are herein incorporated by reference.

Spectral analysis were consistent with the desired product: $^1$H NMR (CDCl$_3$): δ4.92 and 4.75 (1H, 2 s for two rotamers), 4.0–3.8 (1H, m), 3.74 (3H, s), 3.0–2.7 (1H, m), 2.15 (1H, m), 1.44 (9H, br s). MS (FAB): 244 (M$^+$+H).

Step 2: Synthesis of piperidine-1,2S-dicarboxylic acid 1-tert-butyl ester (compound 9):

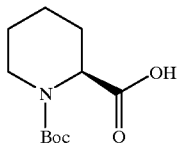

To a methanol solution (25 mL) of compound 8 (28 g, 0.115 mol) was added 2N sodium hydroxide solution (25 mL) at 25° C. After about 20 hours, the solution was concentrated and acidified to a pH of about 2 by the addition of 10% hydrochloric acid (ice-cold). The suspension was extracted with EtOAc (ethyl acetate) (3×100 mL). The combined organic layers were then washed with saturated sodium chloride solution (1×150mL) and dried over sodium sulfate. Evaporation afforded 27 g (quantitative) pale-yellow solid.

Spectral analysis of the pale-yellow solid were consistent with compound 8: $^1$H NMR (CDCl$_3$): δ4.92 and 4.77 (1H, 2 s for two rotamers), 4.1–3.8 (1H, m), 3.1–2.8 (1H, m), 2.3–2.2 (1H, m), 1.41 (9H, br s).

Step 3: Synthesis of piperidine-1,2S-dicarboxylic acid 1-tert-butyl ester 2S-(4-phenyl-butyl) ester (compound 10):

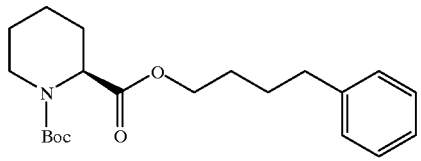

To a CH$_2$Cl$_2$ solution of compound 9 and 1-phenyl-butan-4-ol was added DCC and DMAP at about 25° C. After several hours, the suspension was filtered and the filtrate was concentrated. For example, the suspension is filtered for about 20 hours. The crude oil was passed through a pad of silica gel (5% EtOAc in hexanes) to provide compound 10.

Step 4: Synthesis of piperidine-2S-carboxylic acid 4-phenyl-butyl ester (compound 11):

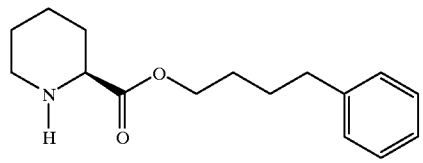

To a CH$_2$Cl$_2$ solution of compound 10 was added trifluoroacetic acid slowly at about 25° C. After about several hours, the CH$_2$Cl$_2$ and trifluoroacetic acid were removed in vacuo and the residue redissolved in CHCl$_3$. The resulting solution was then washed with saturated Na$_2$CO$_3$ and dried with Na$_2$SO$_4$. Evaporation yielded compound 11.

Step 5: Synthesis of 1-chlorosulfonyl-piperidine-2S-carboxylic acid 4-phenyl-butyl ester (compound 12):

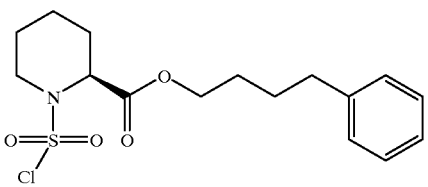

To a CH$_2$Cl$_2$ solution of compound 11 was added Et$_3$N and ClSO$_3$H slowly. The mixture was allowed to warm to about 25° C. and stirred at that temperature for several hours. The solution was then concentrated in vacuo after which benzene was added and evaporated to remove trace amounts of Et$_3$N and water. The residue was added to benzene and PCl$_5$. The suspension was heated at reflux for about 30 minutes, then cooled to about 25° C. and poured into an ice-cold sodium hydroxide solution. The aqueous mixture was extracted with EtOAc. The combined organic layers were washed with a saturated NaHCO$_3$ solution, dried over sodium sulfate and concentrated. The residue was purified by column chromatography (5% EtOAc in hexanes) affording compound 12.

Spectral analysis of the product was consistent with compound 12: $^1$H NMR (CDCl$_3$): δ7.3–7.1 (5H, m), 4.74 (1H, m), 4.2–4.1 (2H, m), 3.88 (1H, d, J=11 Hz), 2.7–2.5 (2H, m), 2.12 (1H, m), 1.88 (1H, m). HRMS (FAB): calculated: 360.1036; found 360.1033.

Step 6: Synthesis of I-phenoxy sulfonyl-piperidine-2S-carboxylic acid 4-phenylbutyl ester (compound 13):

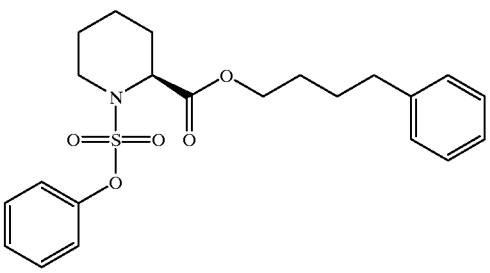

At about 0° C., an ethylene glycol dimethyl ether solution (1 mL) of compound 12 (100 mg, 0.28 mmol) and phenol (58 mg, 0.62 mmol) was added NaH (16 mg, 90%, 0.62 mmol) in three portions. The resulting suspension was then stirred at about 25° C. for 1 hour and poured into a saturated ice-cold NH$_4$Cl solution (10 mL). The aqueous mixture was extracted with EtOAc (2×20 mL). The combined organic layers were then dried over sodium sulfate and concentrated. The residue was purified by column chromatography (CH$_2$Cl$_2$) to yield 11.3 mg (10%) of a colorless oil.

Spectral analysis of the colorless oil was consistent with compound 13: $^1$H NMR (CDCl$_3$): δ7.4–7.1 (10H, m), 4.50 (1H, m), 4.12 (2H, m), 3.68 (1H, dd, J=11, 1.6 Hz), 3.39 (1H, td, J=11, 1.7 Hz), 2.6–2.5 (2H, m), 2.07 (1H, d, J=10.8 Hz). MS (FAB): 418 (M$^+$+H) HRMS (FAB): calculated: 440.1508; found 440.1520.

Example 2

Synthesis of 1-Phenoxy sulfonyl-pyrrolidine-2S-carboxylic acid benzyl ester (Compound 15)

Step 1: Synthesis of 1-chlorosulfonyl-pyrrolidine-2S-carboxylic acid benzyl ester (compound 14):

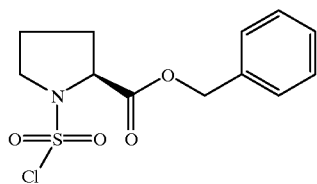

Compound 14 was prepared from pyrrolidine-2-carboxylic acid benzyl ester (commercially available from BACHEM) in a manner analogous to the synthetic method of Example 1—Step 5 set forth above. An 87% yield of compound 14 was obtained.

Spectral analysis of the product was consistent with compound 14: $^1$H NMR (CDCl$_3$): δ7.4–7.1 (5H, m), 5.12 (3H, s), 4.40 (1H, m), 3.67 (1H, m), 3.49 (1H, m). MS (FAB): 326 (M$^+$+Na), 321 (M$^+$+NH$_4$).

Step 2: Synthesis of I-phenoxy sulfonyl-pyrrolidine-2S-carboxylic acid benzyl ester (compound 15):

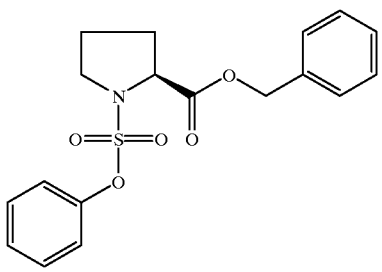

Compound 15 was prepared from compound 14 in a manner analogous to the synthetic method of Example 1—Step 6 set forth above. An 8% yield of compound 15 was obtained.

Spectral analysis of the product was consistent with compound 15: $^1$H NMR (CDCl$_3$): δ7.5–7.2 (10H, m), 5.13 (2H, s), 4.46 (1H, m), 3.7–3.5 (2H, m), 2.4–1.9 (4H, m). HRMS (FAB): calculated: 362.1062; found: 362.1070.

The sulfamoyl compounds of the present invention may be prepared in the manner depicted in Scheme 2 below. As described in Scheme 2, amino acids 1 protected by suitable blocking groups P on the amino acid nitrogen may be reacted with alcohols B'OH to generate esters 2. After removal of the protecting group, the free amine may be reacted with chlorosulfonic acid followed by pentachloride to provide the chlorosulfonyl 4. The chlorosulfonyl 4 may then be reacted with various amines D'NH$_2$ to provide a final product 16. Depending on the structure of the final product being synthesized, it may prove to be more efficient to prepare a compound of formula 16, and then substitute the B' group with an B" group. This may be carried out as depicted in Scheme 2, wherein the product 16 is hydrolyzed to the corresponding alcohols 17 which may then be reacted with alcohols B"OH to provide final products 18.

Scheme 2

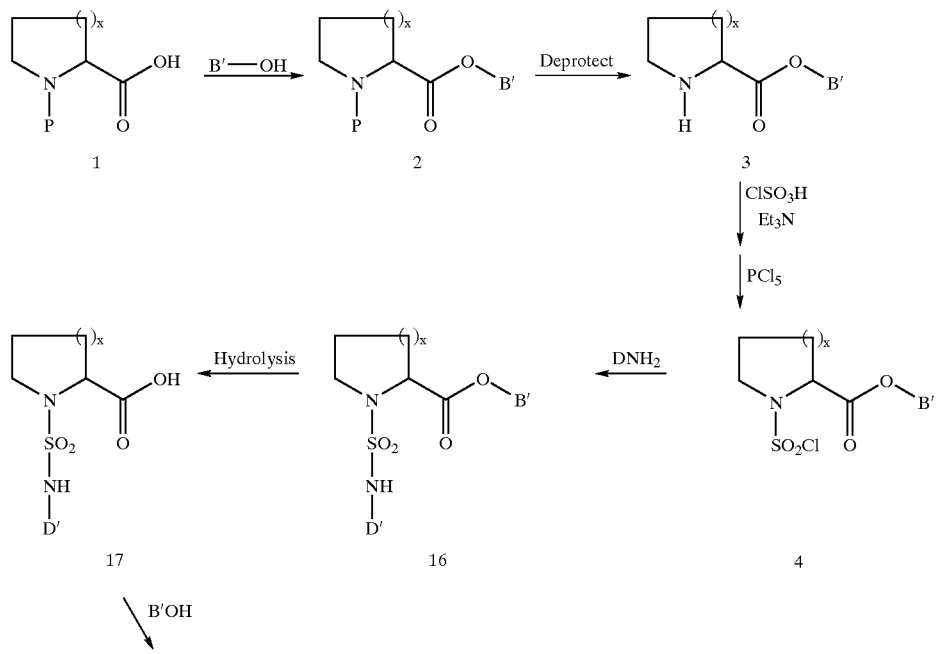

-continued

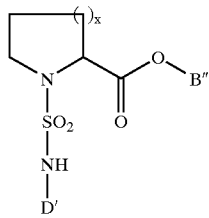

18

In the compounds depicted above in Scheme 2, B' and B" are independently:

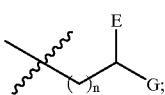

wherein E and G are independently Ar, H, $C_1$–$C_6$ straight or branched alkyl, $C_1$–$C_6$ straight or branched alkenyl, $C_1$–$C_6$ straight or branched alkyl or alkenyl that is substituted with a $C_5$–$C_7$ cycloalkyl, $C_1$–$C_6$ straight or branched alkyl or alkenyl that is substituted with a $C_5$–$C_7$ cycloalkenyl, or Ar substituted $C_1$–$C_6$ straight or branched alkyl or alkenyl, wherein, in each case, one or two of the $CH_2$ groups of the alkyl or alkenyl chains may contain 1–2 heteroatoms selected from the group consisting of oxygen, sulfur, SO and $SO_2$ in chemically reasonable substitution patterns, or

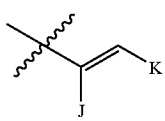

provided that both B' or B" and D' are not H; J is H, $C_1$–$C_6$ straight or branched alkyl or $C_1$–$C_6$ straight or branched alkenyl;

K is Ar or substituted 5–7 membered cycloalkyl with substituents at positions 3 and 4 which are independently selected from the group consisting of H, OH, —O—$(CH_2)_m$-alkyl, —O—$(CH_2)_m$-alkenyl and carbonyl, wherein m is 1–4;

Ar is selected from the group consisting of phenyl, 1-napthyl, 2-naphthyl, 2-furyl, 3-furyl, 2-thienyl, 3-thienyl, 2-pyridyl, 3-pyridyl, 4-pyridyl, monocyclic and bicyclic heterocyclic ring systems with individual ring sizes being 5 or 6 which may contain in either or both rings a total of 1–4 heteroatoms independently selected from O, N and S; wherein Ar may contain one to three substituents which are independently selected from the group consisting of hydrogen, halo, hydroxyl, nitro, trifluoromethyl, trifluoromethoxy, $C_1$–$C_6$ straight or branched alkyl, $C_2$–$C_6$ straight or branched alkenyl, O—($C_1$–$C_4$ straight or branched alkyl), O—($C_2$–$C_4$ straight or branched alkenyl), O-benzyl, O-phenyl, 1,2-methylenedioxy, amino, carboxyl and phenyl;

n is 0 to 4;

D' is $C_1$–$C_6$ straight or branched alkyl, $C_1$–$C_6$ straight or branched alkenyl, $C_5$–$C_7$ cycloalkyl, $C_5$–$C_7$ cycloalkenyl substituted with $C_1$–$C_4$ straight or branched alkyl or $C_1$–$C_4$ straight or branched alkenyl, [($C_2$–$C_4$)-alkyl or ($C_2$–$C_4$)-alkenyl)]-Ar or Ar; and x is 0–1.

The following compounds were prepared according to the general Scheme 2 depicted above:

Example 3

Synthesis of 1-(3,4,5-Trimethoxy-phenylsulfamoyl)-piperidine-2S-carboxylic acid 4-phenyl-1-(3-phenyl-propyl)-butyl ester (Compound 22)

Step 1: Synthesis of piperidine-1,2S-dicarboxylic acid 1-tert-butyl ester 2S-methyl ester (compound 8):

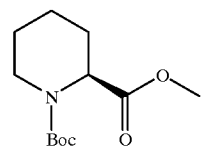

Compound 8 was prepared from racemic pipecolic acid via the published procedures. See R. F. Nutt et al., J. Med. Chem., 24, pp. 692–698 (1981) and C. E. Davies et al., Synth. Comm., 26 (4), pp. 687–696 (1996). These references are herein incorporated by reference.

Spectral analysis were consistent with the desired product: $^1$H NMR (CDCl$_3$):δ4.92 and 4.75 (1H, 2 s for two rotamers), 4.0–3.8 (1H, m), 3.74 (3H, s), 3.0–2.7 (1H, m), 2.15 (1H, m), 1.44 (9H, br s). MS (FAB): 244 (M$^+$+H).

Step 2: Synthesis of piperidine-1,2S-dicarboxylic acid 1-tert-butyl ester (compound 9):

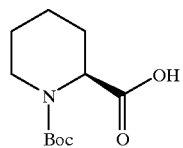

To a methanol solution (25mL) of compound 8 (28 g, 0.115 mol) was added 2N sodium hydroxide solution (25 mL) at 25° C. After about 20 hours, the solution was concentrated and acidified to a pH of about 2 by the addition of 10% hydrochloric acid (ice-cold). The suspension was extracted with EtOAc (3×100 mL). The combined organic layers were then washed with saturated sodium chloride solution (1×150 mL) and dried over sodium sulfate. Evaporation afforded 27 g (quantitative) pale-yellow solid.

Spectral analysis of the pale-yellow solid were consistent with compound 8: $^1$H NMR (CDCl$_3$):δ4.92 and 4.77 (1H, 2 s for two rotamers),4.1–3.8 (1H, m), 3.1–2.8 (1H, m), 2.3–2.2 (1H, m), 1.41 (9H, br s).

Step 3: Synthesis of piperidine-1,2S-dicarboxylic acid 1-tert-butyl ester 2S-[4-phenyl-1-(3-phenyl-propyl)-butyl] ester (compound 19):

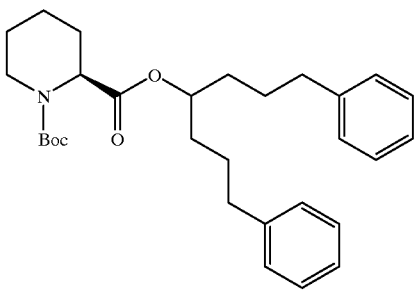

To a CH$_2$Cl$_2$ solution (100 mL) of compound 9 (2.22 g, 9.7 mmol) and 1,7-diphenyl-heptan-4-ol (2 g, 7.5 mmol) was added DCC (4.62 g, 22.4 mmol) and DMAP (0.55 g, 4.5 mmol) at 25° C. After about 2.5 hours, the suspension was filtered and the filtrate was concentrated. The crude oil was passed through a pad of silica gel (5% EtOAc in hexanes) to provide 3.6 g (quantitative) of colorless oil (compound 19).

Step 4: Synthesis of piperidine-2S-carboxylic acid 4-phenyl-1-(3-phenyl-propyl)-butyl ester (compound 20):

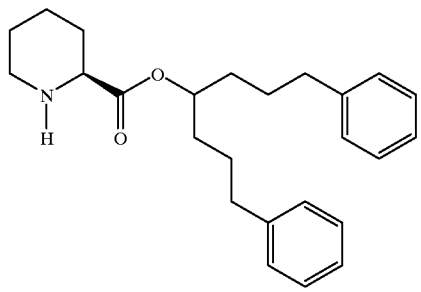

To a CH$_2$Cl$_2$ solution (10 mL) of compound 19 was added trifluoroacetic acid (3 mL) slowly at 25° C. After about 4 hours, the CH$_2$Cl$_2$ and trifluoroacetic acid were removed in vacuo and the residue redissolved in CHCl$_3$ (100 mL). The resulting solution was then washed with saturated Na$_2$CO$_3$ (2×50 mL) and dried with Na$_2$SO$_4$. Evaporation yielded 3 g (95%) of a pale yellow oil (compound 20).

Spectral analysis of the pale-yellow oil was consistent with compound 20: $^1$H NMR (CDCl$_3$):δ7.3–7.0 (10H, 2 m), 4.92 (1H, m), 3.22 (1H, m), 3.00 (1H, m), 12.7–2.4 (5H, m).

Step 5: Synthesis of 1-chlorosulfonyl-piperidine-2S-carboxylic acid 4-phenyl-1-(3-phenyl-propyl)-butyl ester (compound 21):

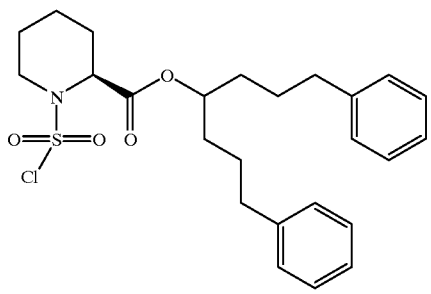

To a CH$_2$Cl$_2$ solution (70 mL) of compound 20 (2.75 g, 7.3 mmol) was added Et$_3$N(2 mL) and ClSO$_3$H (0.97 g, 8.3 mmol) slowly. The mixture was allowed to warm to about 25° C. and stirred at that temperature for about 2 hours. The solution was then concentrated in vacuo after which benzene (2×20 mL) was added and evaporated to remove trace amounts of Et$_3$N and water. The residue was added to benzene (20 mL) and PCl$_5$ (1.97 g, 9.4 mmol). The suspension was heated at reflux for about 30 minutes, then cooled to about 25° C. and poured into an ice-cold sodium hydroxide solution (50 mL). The aqueous mixture was extracted with EtOAc (2×75 mL). The combined organic layers were washed with a saturated NaHCO$_3$ solution (1×100 mL), dried over sodium sulfate and concentrated. The residue was purified by column chromatography (5% EtOAc in hexanes) affording 2.2 g (63%) of a yellow oil.

Spectral analysis of the yellow oil was consistent with compound 21: $^1$H NMR (CDCl$_3$):δ7.4–7.1 (10H, m), 5.05 (1H, m), 4.8 (1H, m), 3.98 (1H, m), 3.7–3.5 (1H, m), 2.7–2.5 (4H, m), 2.18 (1H, m), 1.95 (1H, m).

Step 6: Synthesis of 1-(3,4,5-trimethoxy-phenylsulfamoyl)-piperidine-2S-carboxylic acid 4-phenyl-1-(3-phenyl-propyl)-butyl ester (compound 22):

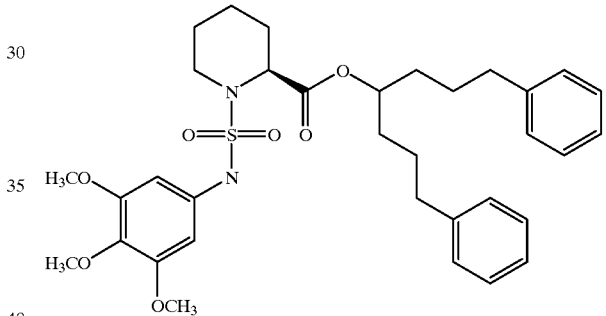

To a pyridine solution (1.5 mL) of 3,4,5-trimethoxyanaline (115 mg, 0.53 mmol) was added compound 21 (100 mg, 0.21 mmol) in CH$_2$Cl$_2$ (1 mL) at about 25° C. After about 6 hours, the suspension was washed with ice-cold 5% HCl solution (1×50 mL) and saturated copper sulfate solution (2×50 mL). After removal of the solvent, the residue was purified by column chromatography (3.5% CH$_3$OH in CH$_2$Cl$_2$) to yield 35 mg (27%) of a pale yellow oil.

Spectral analysis of the oil was consistent with compound 22: $^1$H NMR (CDCl$_3$):δ7.3–7.1 (11H, m), 6.48 (2H, m), 5.07 (1H, m), 4.76 (1H, m), 3,83 (6H, s), 3.81 (3H, s), 3.69 (1H, d, J=11.2 Hz), 3.10 (1H, td, J=11 , 1.9 Hz), 2.61 (4H, m), 2.23 (1H, d, J=10.9 Hz). HRMS (FAB): calculated: 625.2947; found 625.2962.

Example 4

Synthesis of 1-(1,1-Dimethyl-propylsulfamoyl)-piperidine-2S-carboxylic acid 4-phenyl-1-(3-phenyl-propyl)-butyl ester (compound 23)

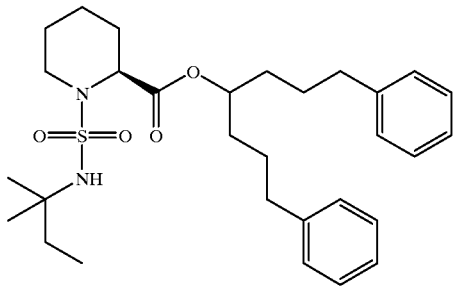

Compound 23 was prepared from compound 21 by a synthetic method analogous to that of Example 3—Step 6. A 9% yield was obtained.

Spectral analysis of the product was consistent with compound 23: $^1$H NMR (CDCl$_3$):δ7.3–7.1 (10H, m), 5.02 (1H, m), 4.98 (1H, s), 4.71 (1H, d, J=1.8 Hz), 3.65 (1H, d, J=11.0 Hz), 3.02 (1H, td, J=11, 1.7 Hz), 2.60 (4H, m), 2.20 (1H, d, J=11.9 Hz), 1.29 (6H, s), 0.86 (3H, t, J=6.4 Hz). HRMS (FAB): calculated: 529.3100; found 529.3113.

Example 5

Synthesis of 1-Phenylsulfamoyl-piperidine-2S-carboxylic acid 4-phenyl-butyl ester (Compound 24)

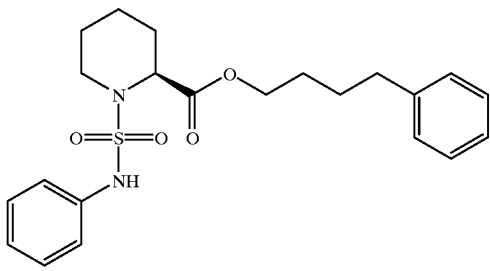

Compound 24 was prepared from compound 12 by a synthetic method analogous to that of Example 3–Step 6. A 33% yield was obtained.

Spectral analysis of the product was consistent with compound 24: $^1$H NMR (CDCl$_3$):δ7.3–7.0 (11H, m), 4.69 (1H, m), 4.2–4.1 (2H, m), 3.58 (1H, d, J=10.6 Hz), 3.01 (1H, td, J=10.6, 1.7 Hz), 2.6–2.5 (2H, m), 2.18 (1H, d, J=11.7 Hz). HRMS (FAB): calculated: 417.1848; found 417.1838.

Example 6

Synthesis of 1-(3,4,5-Trimethoxy-phenylsulfamoyl-piperidine-2S-carboxylic acid 4-phenyl-butyl ester (compound 25)

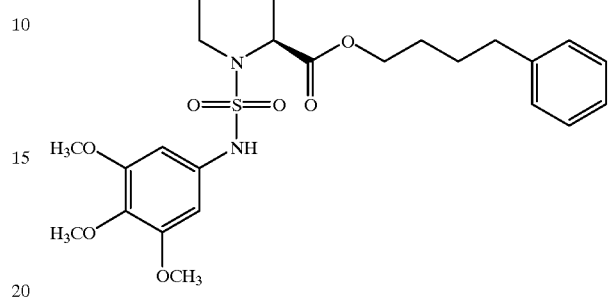

Method I: Compound 25 was prepared from compound 12 by a synthetic method analogous to that of Example 3—Step 6. A 13% yield was obtained.

Spectral analysis of the product was consistent with compound 25: $^1$H NMR (CDCl$_3$):δ7.3–7.1 (6H, m), 6.42 (2H, s), 4.69 (1H, m), 4.2–4.1 (1H, m), 3.78 (6H, s), 3.76 (3H, s), 3.63 (1H, d, J=10.8 Hz), 3.02 (1H, td, J=10.8, 1.8 Hz), 2.6 (2H, m), 2.19 (1H, d, J=11.9 Hz). MS (FAB): 506 (M$^+$). HRMS (FAB): calculated: 639.1141; found 639.1124.

Example 7

Synthesis of 1-(1,1-Dimethyl-propylsulfamoyl)-piperidine-2S-carboxylic acid 4-phenyl-butyl ester (Compound 26)

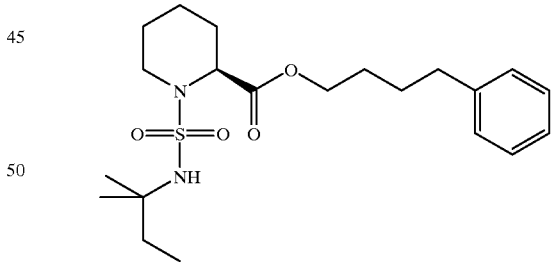

Compound 26 was prepared from compound 12 by a synthetic method analogous to that of Example 3—Step 6. A 38% yield was obtained.

Spectral analysis of the product was consistent with compound 26: $^1$H NMR (CDCl$_3$):δ7.3–7.1 (5H, m), 4.9 (1H, s), 4.63 (1H, d, J=2.3 Hz), 4.2–4.0 (1H, m), 3.58 (1H, d, J=10.7 Hz), 2.92 (1H, td, J=10.7, 1.8 Hz), 2.6–2.5 (2H, m), 2.14 (1H, d, J=11.8 Hz), 1.22 (6H, s), 0.82 (3H, t, J=6.6 Hz). HRMS (FAB): calculated: 411.2318; found 411.2308.

Example 8

Synthesis of 1-(1,1-Dimethyl-propylsulfamoyl)-pyrrolidine-2S-carboxylic acid Benzyl ester (Compound 27)

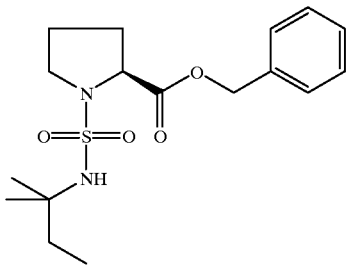

Compound 27 was prepared from compound 14 by a synthetic method analogous to that of Example 3—Step 6. A 42% yield was obtained.

Spectral analysis of the product was consistent with compound 27: $^1$H NMR (CDCl$_3$):δ7.4–7.2 (5H, m), 5.09 (2H, AB), 4.45 (1H, br s), 4.40 (1H, m), 3.40 (1H, m), 2.20 (1H, m), 1.23 (6H, s), 0.83 (3H, t, J=6.7 Hz). MS (FAB): 355 (M$^+$+H). Analysis calculated for C$_{17}$H$_{26}$N$_2$O$_4$S: C 57.60 H 7.39 N 7.90 S 9.05; found: C 57.75 H 7.56 N 7.83 S 9.14

Example 9

Synthesis of 1-Phenylsulfamoyl-pyrrolidine-2S-carboxylic acid Benzyl ester (Compound 28)

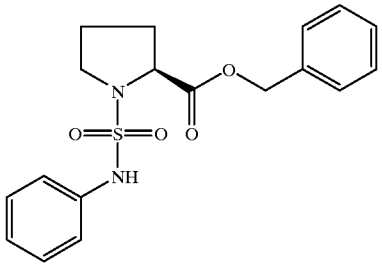

Compound 28 was prepared from compound 14 by a synthetic method analogous to that of Example 3—Step 6. A 59% yield was obtained.

Spectral analysis of the product was consistent with compound 28: $^1$H NMR (CDCl$_3$):δ7.6–7.0 (5H, m), 6.78 (1H, br s), 5.02 (2H, s), 4.50 (1H, dd, J=7.6, 3.4 Hz), 3.5–3.1 (2H, m), 2.4–1.8 (4H, m). HRMS (FAB): calculated: 361.1222; found: 361.1226.

Example 10

Synthesis of 1-(3,4,5-Trimethoxy-phenylsulfamoyl)-pyrrolidine-2S-carboxylic acid Benzyl ester (Compound 29)

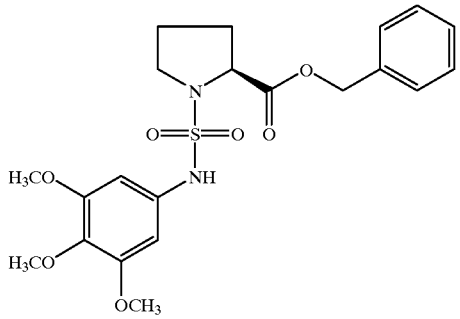

Compound 29 was prepared from compound 14 by a synthetic method analogous to that of Example 3—Step 6. A 29% yield was obtained.

Spectral analysis of the product was consistent with compound 29: $^1$H NMR (CDCl$_3$):δ7.5–7.3 (5H, m), 6.76 (1H, br s), 6.45 (2H, s), 5.03 (2H, AB), 4.46 (1H, dd, J=7.4, 3.2 Hz), 3.77 (6H, s), 3.75 (3H, s), 3.5–3.2 (2H, m), 2.2–1.8 (4H, m). HRMS (FAB): calculated: 451.1539; found: 451.1522.

Example 11

Synthesis of 1-(1,1-Dimethyl-propylsulfamoyl)-pyrrolidine-2S-carboxylic acid 3-pyridin-3-yl-propyl ester (Compound 31)

Step 1: Synthesis of 1-(1,1-Dimethyl-propylsulfamoyl)-pyrrolidine-2S-carboxylic acid (compound 30):

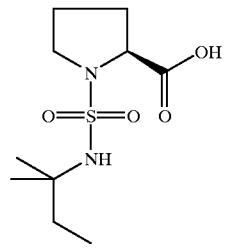

To a methanol solution (1 mL) of compound 27 (32 mg, 0.09 mmol) was added palladium on charcoal (3 mg) at about 25° C. The suspension was kept under hydrogen atmosphere (1 atmospheres) for about 1.5 hours and filtered through a pad of celite. The filtrate was concentrated to provide 24 mg (quantitative) of a colorless oil.

Spectral analysis of the colorless oil was consistent with compound 30: $^1$H NMR (CDCl$_3$):δ8.3 (1H, br s), 4.4 (1H, br s), 4.37 (1H, dd, J=7.6, 3.2 Hz), 3.41 (1H, t, J=6.2 Hz), 2.3–1.8 (4H, m), 1.60 (2H, m), 1.22 (6H, s), 0.83 (3H, t, J=6.3 Hz).

Step 2: Synthesis of 1-(1,1-Dimethyl-propylsulfamoyl)-pyrrolidine-2S-carboxylic acid 3-pyridin-3-yl-propyl ester (compound 31):

33

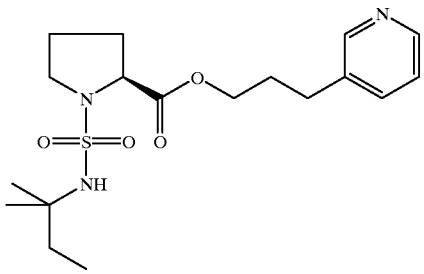

34

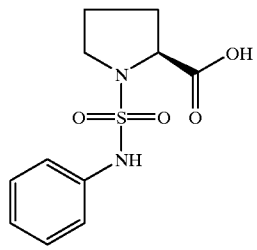

To a CH$_2$Cl$_2$ solution (1 mL) of compound 30 (24 mg, 0.09 mmol) and 3-pyridin-3-yl-propan-1-ol was added EDC (22.5 mg, 0.12 mmol) and HOBT (16 mg, 0.12 mmol) at about 25° C. After about 20 hours, the mixture was diluted with EtOAc (50 mL), washed with saturated NH$_4$Cl solution (2×50 mL), dried over sodium sulfate and concentrated. The residue was purified by column chromatography (50% EtOAc in hexanes) yielding 29 mg (85%) of a pale yellow oil.

Spectral analysis of the colorless oil was consistent with compound 31: $^1$H NMR (CDCl$_3$):δ8.43 (2H, br s), 7.53 (1H, m), 7.1 (1H, m), 4.48 (1H, br s), 4.32 (1H, dd, J=7.7, 3.3 Hz), 4.2–4.0 (2H, m), 3.40 (2H, t, J=6.1 Hz), 2.62 (2H, m), 2.3–2.1 (1H, m), 1.55 (2H, m), 1.23 (6H, s), 0.83 (3H, t, J=6.4 Hz). HRMS (FAB): calculated: 384.1957; found: 384.1963.

Example 12

Synthesis of 1-Phenylsulfamoyl-pyrrolidine-2S-carboxylic acid 3-pyridin-3-yl-propyl ester (Compound 33)

Step 1: Synthesis of 1-Phenylsulfamoyl-pyrrolidine-2S-carboxylic acid (compound 32):

Compound 32 was synthesized from compound 28 by a synthetic method analogous to that set forth in Example 11—Step 1. An 81% yield was obtained.

Step 2: Synthesis of I-Phenylsulfamoyl-pyrrolidine-2S-carboxylic acid 3-pyridin-3-yl-propyl ester (compound 33):

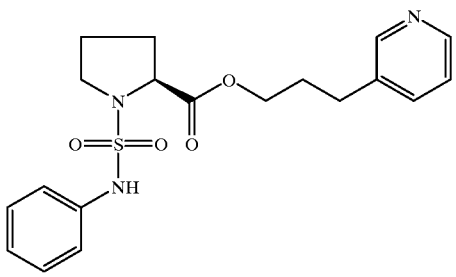

Compound 33 was prepared from compound 32 by a synthetic method analogous to that of Example 11—Step 2. A 30% yield was obtained.

Spectral analysis of the product was consistent with compound 33: $^1$H NMR (CDCl$_3$):δ8.48 (2H, br s), 7.82 (1H, br s), 7.52 (1H, m), 7.3–7.0 (6H, m), 4.40 (1H, dd, J=7.8, 3.5 Hz), 4.2–4.0 (2H, m), 3.43 (2H, t, J=6.2 Hz), 2.71 (2H, m), 2.3–2.1 (1H, m). HRMS (FAB): calculated: 390.1488; found: 390.1476.

The compounds of the formula (II) may be readily prepared by standard techniques of organic chemistry, utilizing the general synthetic pathways depicted below. The benzyl esters of the present invention may be prepared in the manner depicted in Scheme 3 below:

Scheme 3

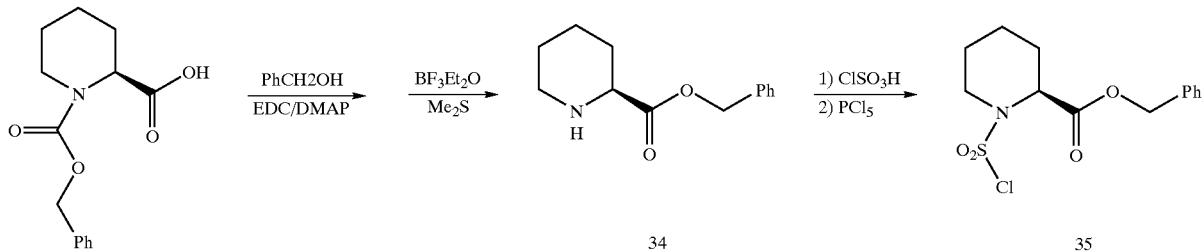

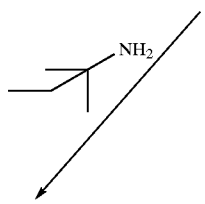

-continued
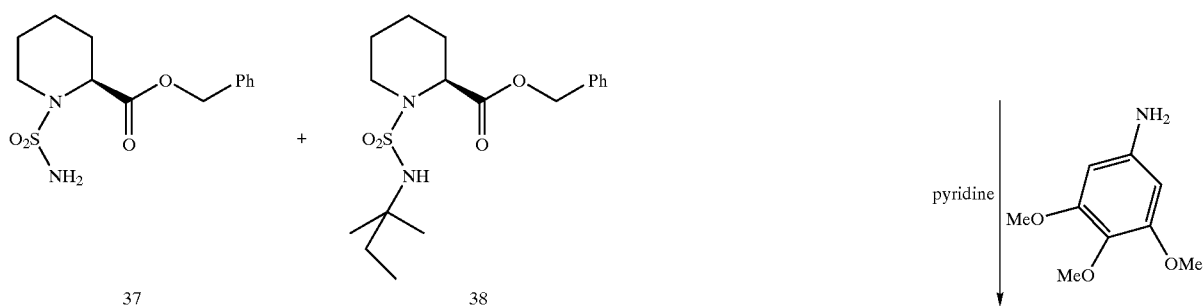
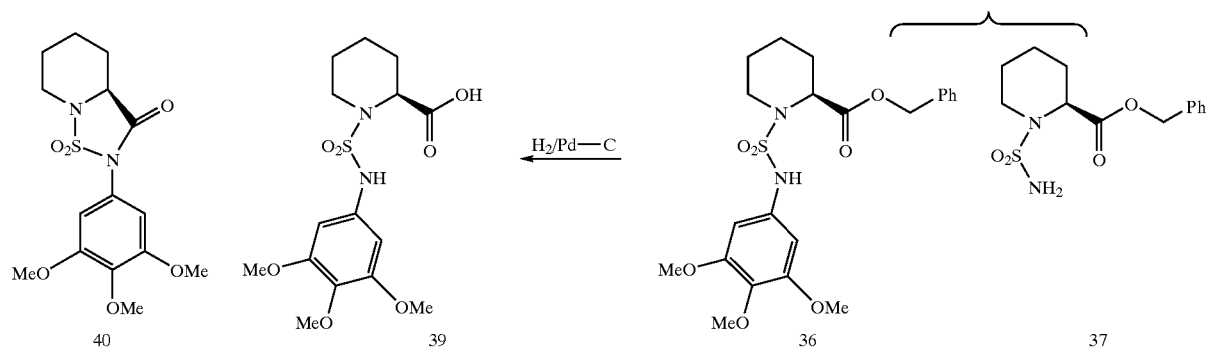
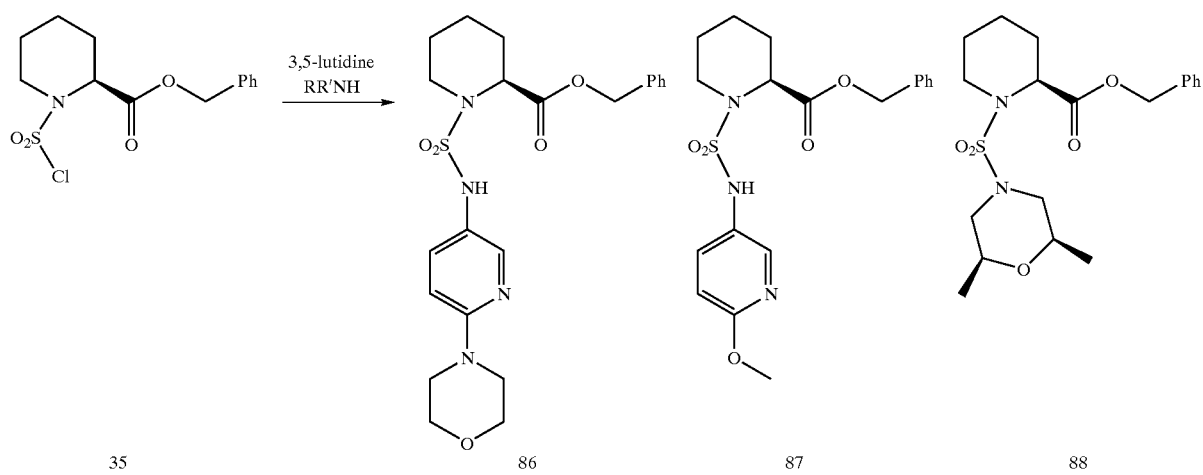
35
Method II
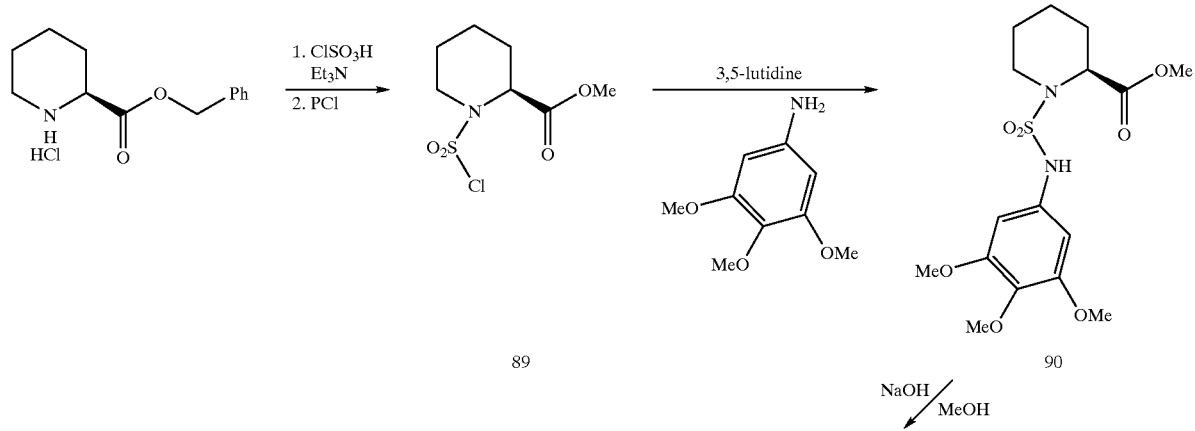

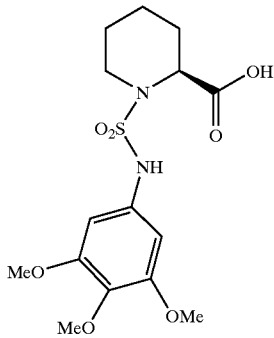

39

EDC, RNH$_2$
CH$_2$Cl$_2$

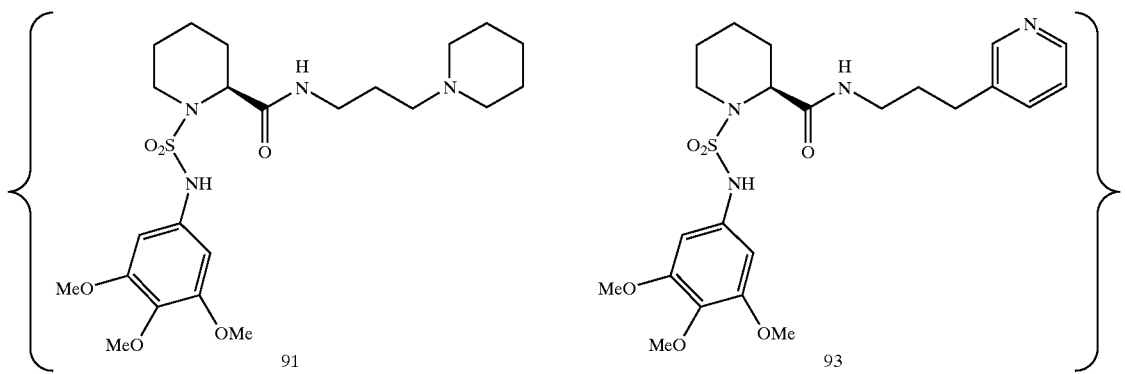

The following compounds were prepared according to Scheme 3 depicted above:

Example 13

Synthesis of 1-(3,4,5-Trimethoxy-phenylsulfamoyl)-piperidine-2S-carboxylic acid Benzyl ester (Compound 36) and 1-sulfamoyl-piperidine-2S-carboxylic acid Benzyl ester (Compound 37)

Step 1: Synthesis of piperidine-2S-carboxylic acid benzyl ester (compound 34):

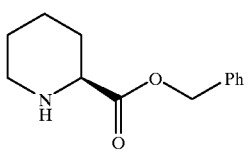

To a CH$_2$Cl$_2$ solution (60 mL) of (S)-(1)-1-(carbobenzyloxy)-2-piperidincarboxylic acid (10 g, 38.0 mmol) and benzyl alcohol (4.72 mL, 45.6 mmol) were added EDC (14.6 g, 76 mmol) and DMAP (1.39 g, 11.4 mmol) at 25° C. After 20 hours, the suspension was diluted with 100 mL of Et$_2$O, washed with brine (2×100 mL), dried over MgSO$_4$ and concentrated. The crude oil was passed through a pad of silica gel (5% EtOAc in hexanes) to provide 12.3 g of colorless oil, which was dissolved in a 1:1 (v/v, 100 mL) mixture of Me$_2$S and CH$_2$Cl$_2$, followed by addition of BF$_3$•Et$_2$O. After 20 hours at 25° C., the mixture was concentrated, diluted with EtOAc (100 mL), washed with ice-cold 5% NaOH solution (1×80 mL) and dried over Na$_2$SO$_4$. After removal of solvent in vacuo, 5 g of brown oil was obtained (66% yield).

Spectral analysis of the product was consistent with compound 34: $^1$H NMR (CDCl$_3$):δ7.45–7.3 (5H, m), 5.24 (2H, AB), 4.41 (1H, br s), 3.92 (1H, dd, J=11, 3.9 Hz), 3.50 (1H, br d), 3.08 (1H, m), 2.23 (1H, m).

Step 2: Synthesis of 1-Chlorosulfonyl-piperidine-2S-carboxylic acid benzyl ester (compound 35):

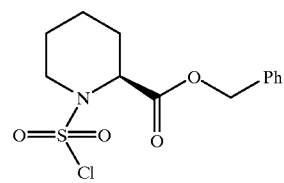

Compound 35 was prepared from compound 34 by a synthetic method analogous to that of Example 3—Step 5. An 83% yield of compound 35 was obtained.

Spectral analysis of the product was consistent with compound 35: $^1$H NMR (CDCl$_3$):δ7.5–7.3 (5H, m), 5.22 (2H, s), 4.88 (1H, d, J=5.7 Hz), 3.97 (1H, d, J=12.8 Hz), 3.7–3.5 (1H, m), 2.22 (1H, dd, J=12.7, 1.9 Hz), 2.0–1.9 (1H, m), 1.8–1.65 (3H, m), 1.5–1.3 (1H, m).

Step 3: Synthesis of 1-(3,4,5-Trimethoxy-phenylsulfamoyl)-piperidine-2S-carboxylic acid benzyl ester (compound 36) and 1-sulfamoyl-piperidine-2S-carboxylic acid benzyl ester (compound 37):

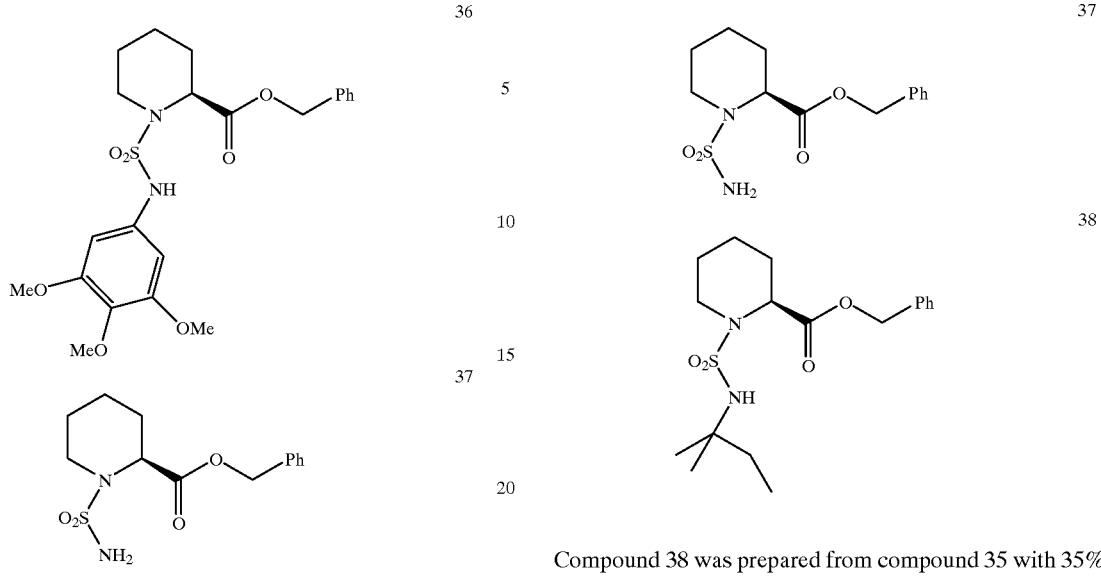

36

37

38

Compound 36 was prepared from compound 35 by a synthetic method analogous to Example 3—Step 6. Compound 36 was obtained in 21% yield. Compound 37 was also isolated from the reaction in 30% yield.

Spectral analysis of the product was consistent with compound 36: $^1$H NMR (CDCl$_3$):δ7.45–7.3 (5H, m), 7.08 (1H, br s), 6.49 (2H, s), 5.24 (2H, q (AB), $J_{app}$=12 Hz), 4.82 (1H, br d, J=2.5 Hz), 3.84 (6H, s), 3.81 (3H, s), 3.69 (1H, br d, J=11.5 Hz), 3.11(1H, td, J=11.8, 3 Hz), 2.30(1H, d, J=13 Hz). MS (FAB): 464 (M$^+$).

Spectral analysis of the product was consistent with compound 37: $^1$H NMR (CDCl$_3$):δ7.45–7.3 (5H, m), 5.19 (2H, AB), 4.87 (2H, br s), 4.77 (1H, br d, J=4.2 Hz), 3.64 (1H, br d), 3.00 (1H, td, J=12.3, 3 Hz), 2.32 (1H, br d).

Compound 38 was prepared from compound 35 with 35% yield by a synthetic method analogous to Example 3—Step 6. Compound 37 was also isolated from the reaction in 44% yield.

Spectral analysis of the product was consistent with compound 38: $^1$H NMR (CDCl$_3$):δ7.45–7.28 (5H, m), 5.20 (2H, q (AB), $J_{app}$=12 Hz), 4.89 (1H. s), 4.78 (1H, d, J=3 Hz), 3.64 (1H, br d, J=11.5 Hz), 3.03 (1H, td, J=11.8, 3.2 Hz), 2.28 (1H, d, J=13.5 Hz), 1.28 (6H, s), 0.89 (3H, t, J=6 Hz). HRMS (FAB): calculated for C$_{18}$H$_{28}$N$_2$O$_4$SNa (M+Na$^+$) 391.1667; found 391.1670.

Example 14

Synthesis of 1-(1,1-Dimethyl-propylsulfamoyl)-piperidine-2S-carboxylic acid Benzyl ester (Compound 38) and 1-sulfamoyl-piperidine-2S-carboxylic acid Benzyl ester (Compound 37)

Step 1: Synthesis of 1-Chlorosulfonyl-piperidine-2S-carboxylic acid benzyl ester (compound 35):

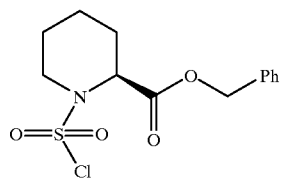

Compound 35 was prepared analogous to Example 13—Step 2.

Step 2: Synthesis of 1-(1, 1-Dimethyl-propylsulfamoyl)-piperidine-2S-carboxylic acid benzyl ester (compound 38) and 1-sulfamoyl-piperidine-2S-carboxylic acid benzyl ester (compound 37):

Example 15

Synthesis of 1-(3,4,5-Trimethoxy-phenylsulfamoyl)-piperidine-2S-carboxylic acid (Compound 39)

Step 1: Synthesis of 1-(3,4,5-Trimethoxy-phenylsulfamoyl)-piperidine-2S-carboxylic acid benzyl ester (compound 36):

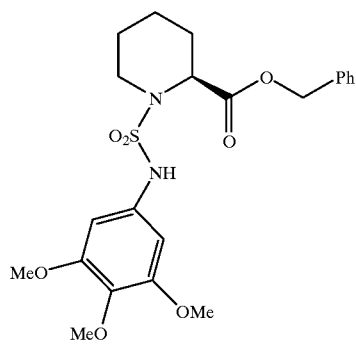

Compound 36 was prepared analogous to Example 13—Step 3.

Step 2: Synthesis of 1-(3,4,5-Trimethoxy-phenylsulfamoyl)-piperidine-2S-carboxylic acid (compound 39):

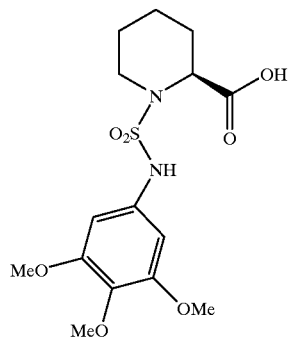

Method I: A methanol solution (5 mL) of compound 36 (240 mg, 0.52 mmol) was added 10% Pd on carbon (24 mg) and kept under hydrogen atmosphere (1 atm) for 1.5 hours. After filtering off the catalyst, the solvent was removed to give 200 mg of white solid (quantitative).

Spectral analysis of the product was consistent with compound 39: $^1$H NMR (CDCl$_3$):δ8–7.8 (1H, br s), 7.22 (1H, br s), 4.78 (1H, br d, J=3 Hz), 3.82 (6H, s), 3.81 (3H, s), 3.70 (1H, brd, J=13 Hz), 3.19 (1H, td, J=13, 3Hz), 2.25 (1H, d, J=12.8 Hz).

Example 16

Synthesis of 1,1-Dioxo-2-(3,4,5-trimethoxy-phenyl)-hexahydro-1-[1,2,5] Thiadiazolo [2,3-]pyridin-3-one (Compound 40)

Step 1: Synthesis of 1-(3,4,5-Trimethoxy-phenylsulfamoyl)-piperidine-2S-carboxylic acid (compound 39):

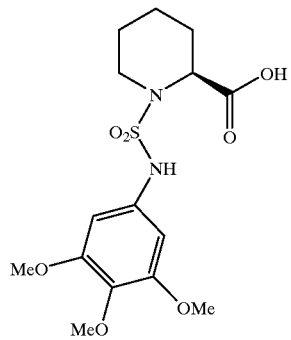

Compound 39 was prepared analogous to Example 15—Step 2.

Step 2: Synthesis of 1,1-Dioxo-2-(3,4,5-trimethoxy-phenyl)-hexahydro-1-[1,2,5] thiadiazolo [2,3] pyridin-3-one (compound 40):

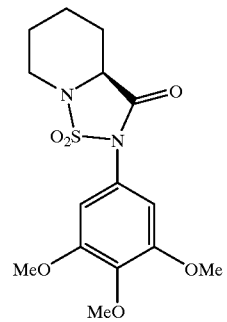

To a DMF solution (2 mL) of compound 39 (30 mg, 0.13 mmol) were added O-(7-azabenzotriazol-1-yl)-1,1,3,3-tetramethyl amonium hexafluorophosphate (HATU, 61 mg, 0.6 mmol) and diisopropyl ethyl amine (50 μM). The mixture was stirred at 25° C. for 24 hours, diluted with Et$_2$O (25 mL), washed with brine (3×30 mL) and dried over MgSO$_4$. After evaporation of organic solvents, the residue was purified by column chromatography (50% EtOAc in hexanes) to give 20 mg (43% yield) of off-white solid.

Spectral analysis of the product was consistent with compound 40: $^1$H NMR (CDCl$_3$):δ6.63 (2H, s), 3.93 (1H, dd, J=13, 3 Hz), 3.87 (9H, s), 3.84 (1h, br d), 3.07 (1H, td, J=13, 3 Hz), 2.3 (1H, m), 2.1 (1H, m).MS (ESP) 379 (M+Na$^+$).

Example 17

Synthesis of (S)-1-(6-Morpholin-4-yl-pyridin-3-ylsulfamoyl)-piperidine-2-carboxylic acid Benzyl ester (compound 86)

Step 1: Synthesis of 1-Chlorosulfonyl-piperidine-2S-carboxylic acid benzyl ester (compound 35):

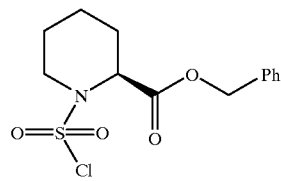

Compound 35 was prepared analogous to Example 13—Step 2.

Step 2: Synthesis of (S)-1-(6-Morpholin-4-yl-pyridin-3-ylsulfamoyl)-piperidine-2-carboxylic acid benzyl ester (compound 86:)

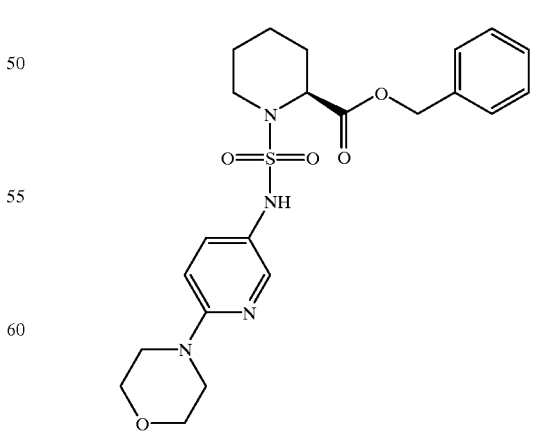

Compound 86 was prepared from the sulfamoyl chloride (compound 35) and 6-morpholin-4-yl-pyridin-3-ylamine by a synthetic method analogous to the method II of compound 25 synthesis. During the work-up of the reaction, concentrated cupric sulfate solution instead of HCl solution was used to wash off 3,5-lutidine. A 72% yield was obtained for the title compound.

Spectral analysis of the product was consistent with compound 86: $^1$H NMR (CDCl$_3$):δ8.09 (1H, d, J=2.4 Hz), 7.51 (1H, dd, J=9, 2.7 Hz), 7.42–7.31 (5H, m), 6.78 (1H, br s), 6.59 (1H, d, J=9 Hz), 5.23 (2H, AB), 4.76 (1H, br d), 3.81 (4H, t, J=4.5 Hz), 3.61 (1H, br d), 3.47 (1H, t, J=4.8 Hz), 3.10 (1H, td, J=12.6, 3.3 Hz), 2.27 (1H, m). HRMS (MALDI) calculated for C$_{22}$H$_{28}$N$_4$O$_5$SNa (M+Na$^+$) 483.1673; found 483.1691.

Example 18

Synthesis of 1-(6-Methoxy-pyridin-3-ylsulfamoyl)-piperidine-2S-carboxylic acid Benzyl ester (Compound 87)

Step 1: Synthesis of 1-Chlorosulfonyl-piperidine-2S-carboxylic acid benzyl ester (compound 35):

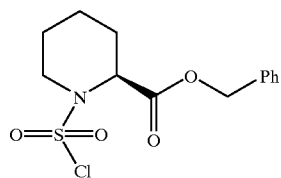

Compound 35 was prepared analogous to Example 13—Step 2.
Step 2: Synthesis of 1-(6-Methoxy-pyridin-3-ylsulfamoyl)-piperidine-2S-carboxylic acid benzyl ester (compound 87):

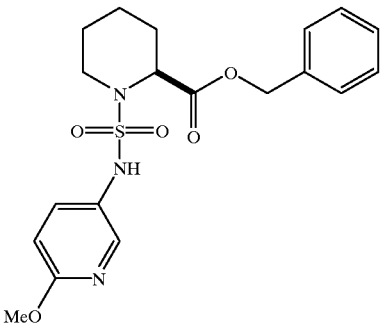

Compound 87 was prepared from the sulfamoyl chloride (compound 35) and 6-methoxy-pyridin-3-ylamine by a synthetic method analogous to the method II of compound 25 synthesis. During the work-up of the reaction, concentrated cupric sulfate solution instead of HCl solution was used to wash off 3,5-lutidine. An 89% yield was obtained for the title compound.

Spectral analysis of the product was consistent with compound 87: $^1$H NMR (CDCl$_3$):δ8.04 (1H, d, J=3 Hz), 7.56 (1H, dd, J=9, 2.7 Hz), 7.42–7.32 (5H, m), 6.97 (1H, br s), 6.69 (1H, d, J=9.3 Hz), 5.23 (2H, AB), 4.77 (1H, br d), 3.91 (3H, s), 3.62 (1H, br d), 3.09 (1H, td, J=12.3, 3 Hz), 2.28 (1H, m). HRMS (MALDI) calculated for C$_{19}$H$_{23}$N$_3$O$_5$SNa (M+Na$^+$) 428.1251; found 428.1249.

Example 19

Synthesis of 1(S)-1-(cis-2,6-Dimethyl-morpholine-4-sulfonyl)-piperidine-2-carboxylic acid Benzyl ester (Compound 88)

Step 1: Synthesis of 1-Chlorosulfonyl-piperidine-2S-carboxylic acid benzyl ester (compound 35):

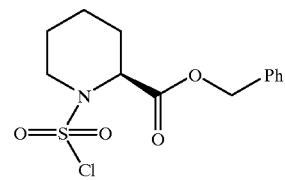

Compound 35 was prepared analogous to Example 13—Step 2.
Step 2: Synthesis of (S)-1-(cis-2,6-Dimethyl-morpholine-4-sulfonyl)-piperidine-2-carboxylic acid benzyl ester (compound 88):

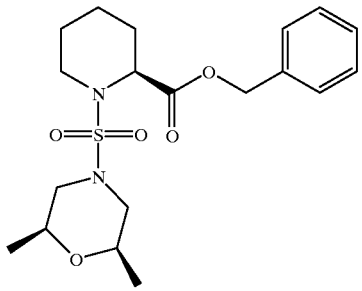

Compound 88 was prepared from the sulfamoyl chloride (compound 35) and cis-2,6-dimethyl-morpholine by a synthetic method analogous to the method II of compound 25 synthesis. A 99% yield was obtained for the title compound.

Spectral analysis of the product was consistent with compound 88: $^1$H NMR (CDCl$_3$):δ7.4–7.3 (5H, m), 5.19 (2H, AB), 4.57 (1H, br d), 3.68 (1H, br d), 3.52 (2H, m), 3.46–3.26 (3H, m), 2.41 (2H, q, J=12 Hz), 2.19 (1H, m). HRMS (MALDI) calculated for C$_{19}$H$_{29}$N$_2$O$_5$S (M+H$^+$) 397.1792; found 397.1806.

Example 20

Synthesis of Compound 89

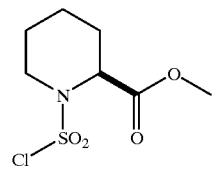

Compound 89 was prepared from (S)-piperidine-2-carboxylic acid methyl ester hydrochloride salt by a method analogous to the synthesis of compound 21. A 26% yield was obtained for the title compound.

Spectral analysis of the product was consistent with compound 89: $^1$H NMR (CDCl$_3$):δ4.83 (1H, br d), 3.98 (1H, br d), 3.80 (3H, s), 3.64–3.52 (1H, m), 2.19 (1H, m), 1.96 (1H, m).

Example 21

Synthesis of (S)-1-(3,4,5-Trimethoxy-phenylsulfamoyl)-piperidine-2-carboxylic acid Methyl ester (Compound 90)

Step 1: Synthesis of compound 89:

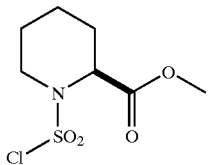

Compound 89 was prepared analogous to Example 20.

Step 2: Synthesis of (S)-1-(3,4,5-Trimethoxy-phenylsulfamoyl)-piperidine-2-carboxylic acid methyl ester (compound 90):

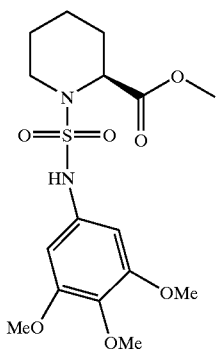

Compound 90 was prepared from the sulfamoyl chloride (compound 89) and 3,4,5-trimethoxy-phenylamine by a synthetic method analogous to the method It of compound 25 synthesis. An 88% yield was obtained for the title compound.

Spectral analysis of the product was consistent with compound 90: $^1$H NMR (CDCl$_3$):δ7.09 (1H, s), 6.50 (2H, s), 4.77 (1H, br s), 3.85 (6H, s), 3.81 (6H, s), 3.70 (1H, br d), 3.11 (1H, td, J=12.6, 2.7 Hz), 2.27 (1H, br d). HRMS (MALDI) calculated for C$_{16}$H$_{25}$N$_2$O$_7$S (M+H$^+$) 389.1382; found 389.1395.

Example 20.5

Synthesis of (S)-2-(6-Phenyl-hexanoyl)- piperidine-1-sulfonic acid (3,4,5-trimethoxy-phenyl)-amide (Compound 119)

Step 1: Synthesis of (S)-1-(3,4,5-Trimethoxy-phenylsulfamoyl)-piperidine-2-carboxylic acid methyl ester (compound 90):

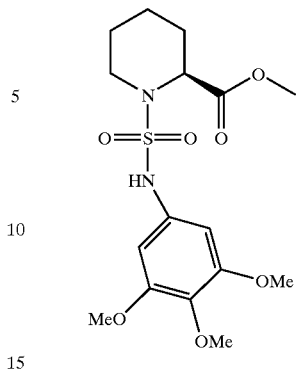

Compound 90 was prepared analogous to Example 21—Step 2.

Step 2: Synthesis of (S)-2-(6-Phenyl-hexanoyl)- piperidine-1-sulfonic acid (3,4,5-trimethoxy-phenyl)-amide (compound 119):

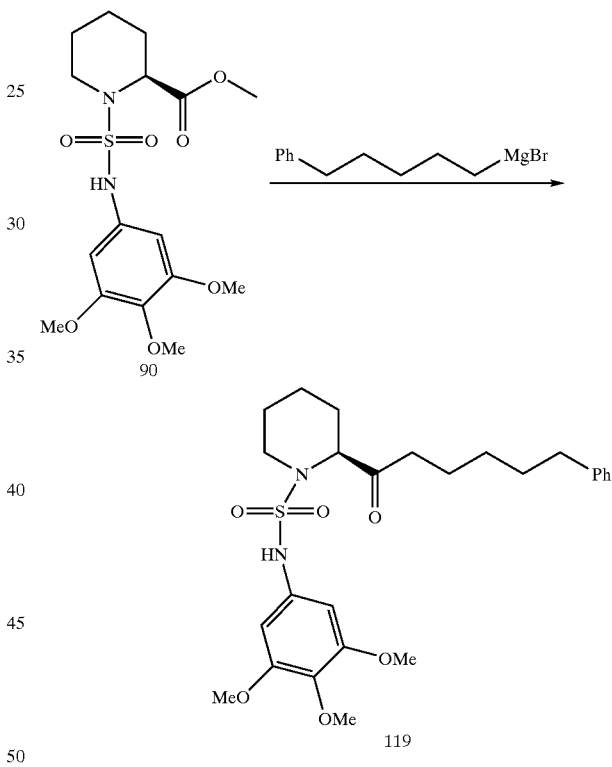

At 40° C., 5-phenylpentylbromide solution (1.15 g, 5 mmol) in ether (5 mL) was slowly added to magnesium turnings with vigorous agitation under Argon. The exothermic reaction was initialized after addition of one quarter of the bromide solution. Once the addition was completed, the suspension was heated at reflux for 30 minutes and most of magnesium was dissolved. The resulted 1M Grignard reagent was cooled to −70° C. and added the methyl ester (compound 90, 100 mg, 0.25 mmol) in THF solution (2 mL). The mixture was warmed to 25° C. and stirred at that temperature for 20 hours. Saturated amonium chloride (1 mL) was introduced to quench the reaction. The suspension was extracted with ether (1×50 mL). The organic phase was collected, dried and concentrated. The residue was purified by flash column chromatography (25% EtOAc in hexanes) followed by preparative TLC (1% THF in CH$_2$Cl$_2$) to give 1.2 mg (1% yield) of the title compound.

Spectral analysis of the product was consistent with compound 119: $^1$H NMR (CDCl$_3$):δ7.33–7.1 (5H, m), 6.91 (1H, s), 6.50 (2H, s), 4.60 (1H, br d), 3.85 (6H, s), 3.81 (3H, s), 3.67 (1H, br d), 3.13 (1H, td, J=12.6, 3 Hz), 2.61 (2H, t, J=7.8 Hz), 2.50 (2H, m), 2.22 (1H, br d). LCMS: 503 (M–H$^+$).

Example 22

Synthesis of 1-(3,4,5-Trimethoxy-phenylsulfamoyl)-piperidine-2S-carboxylic acid (Compound 39)

Step 1: Synthesis of (S)-1-(3,4,5-Trimethoxy-phenylsulfamoyl)-piperidine-2-carboxylic acid methyl ester (compound 90):

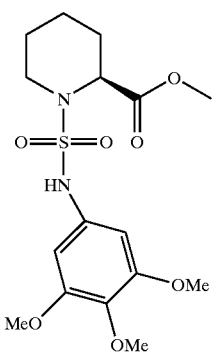

Compound 90 was prepared analogous to Example 21—Step 2.

Step 2: Synthesis of 1-(3,4,5-Trimethoxy-phenylsulfamoyl)-piperidine-2S-carboxylic acid (compound 39):

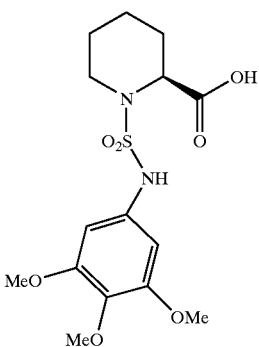

Method II: At 0° C., the methyl ester (compound 90, 700 mg, 2.35 mmol) in methanol (5 mL) was treated with 1% NaOH solution (5 mL). After 24 hours at 25° C., the mixture was concentrated in vacuo, and acidified by addition of ice-cold 10% HCl solution (pH~1). The aqueous solution was extracted with CH$_2$Cl$_2$ (3×50 mL). Combined organic layers were dried and concentrated to afford 540 mg (81% yield) of the title compound as a white foam.

Example 23

Synthesis of (S)-1-(3,4,5-Trimethoxy-phenylsulfamoyl)-piperidine-2-carboxylic acid (3-piperidin-1-yl-propyl)-amide (Compound 91)

Step 1: Synthesis of 1-(3,4,5-Trimethoxy-phenylsulfamoyl)-piperidine-2S-carboxylic acid (compound 39):

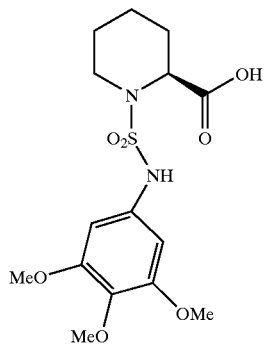

Compound 39 was prepared analogous to Example 22—Step 2.

Step 2: Synthesis of (S)-1-(3,4,5-Trimethoxy-phenylsulfamoyl)-piperidine-2-carboxylic acid (3-piperidin-1-yl-propyl)-amide (compound 91):

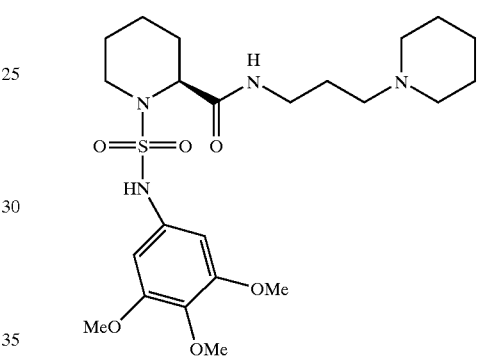

To a CH$_2$Cl$_2$ solution (1.5 mL) of the carboxylic acid (compound 39, 79 mg, 0.211 mmol) and the N-aminopropyl piperidine (100 mg, 0.703 mmol) was added EDC (121 mg, 0.633 mmol). The mixture was stirred for 20 hours and concentrated in vacuo. The residue was purified by reverse phase HPLC to give 55 mg (52% yield) of the title compound.

Spectral analysis of the product was consistent with compound 91: $^1$H NMR (CDCl$_3$):δ7.79 (1H, br t), 6.54 (2H, s), 4.41 (1H, br s), 3.83 (6H, s), 3.81 (3H, s), 3.72 (1H, br d), 3.61 (2H, br d), 3.52–3.38 (2H, m), 3.33–3.22 (1H, m), 3.11 (2H, m), 2.64 (2H, m). HRMS (MALDI) calculated for C$_{23}$H$_{39}$N$_4$O$_6$S (M+H$^+$) 499.2590; found 499.2580.

Example 24

Synthesis of Compound 92

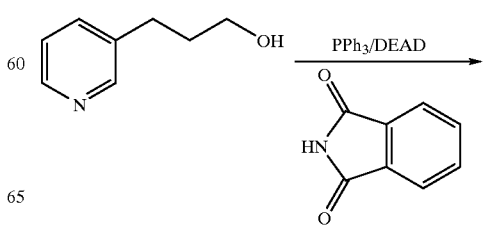

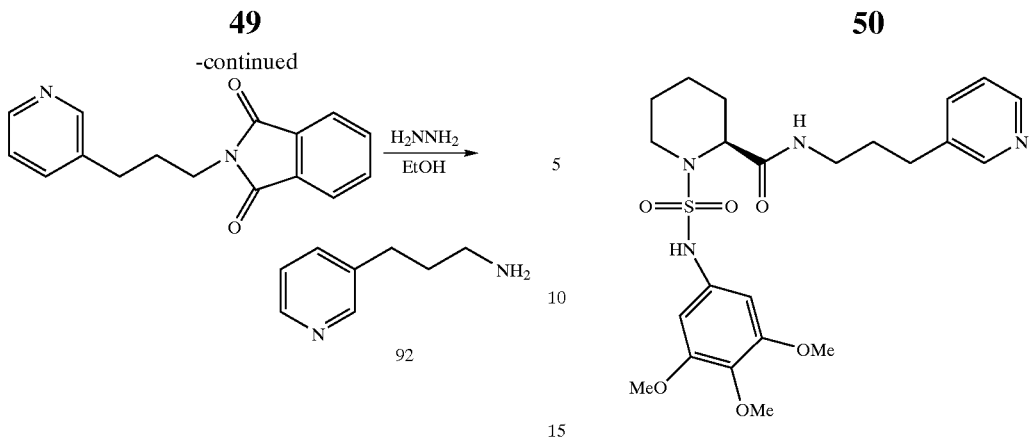

To a THF solution (50 mL) of 3-pyridinepropanol (2g, 14.6 mmol) were added phthalimide (2.6 g, 17.5 mmol), triphenylphosphine (4.59 g, 17.5 mmol) and diethyl azodicarboxylate (3.05 g, 17.5 mmol) sequentially. The solution was stirred for 48 hours and concentrated. The syrup was redissolved in EtOAc (100 mL), washed with brine (2×100 mL), dried and concentrated. The residue was added EtOH (50 mL), followed by hydrazine (0.5 g). The solution was heated at 55° C. for 30 minutes. Large amount of precipitate was produced. The suspension was filtered after cooled to room temperature. The filtrate was concentrated in vacuo to give a reddish oil which was treated with 1% HCl solution (10 mL). The aqueous solution was washed with EtOAc (25 mL) and $Et_2O$ (25 mL), and basified to pH>12 by addition of ice-cold 10% NaOH solution (5 mL). The mixture was extracted with $CH_2Cl_2$ (3×30 mL). Combined organic layers were dried and concentrated to give 1.45 g (74% yield for two steps) of the title compound as a pale yellow oil.

Example 25

Synthesis of (S)-1-(3,4,5-Trimethoxy-phenylsulfamoyl)-piperidine-2-carboxylic acid (3-pyridin-3-yl-propyl)-amide (Compound 93)

Step 1: Synthesis of 1-(3,4,5-Trimethoxy-phenylsulfamoyl)-piperidine-2S-carboxylic acid (compound 39):

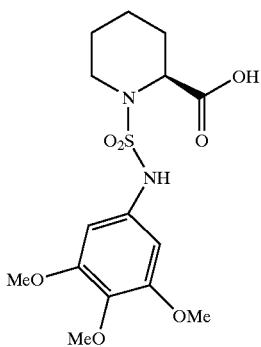

Compound 39 was prepared analogous to Example 22—Step 2.

Step 2: Synthesis of (S)-1-(3,4,5-Trimethoxy-phenylsulfamoyl)-piperidine-2-carboxylic acid (3-pyridin-3-yl-propyl)-amide (compound 93):

Compound 93 was prepared from the carboxylic acid (compound 39) and 3-pyridin-3-yl-propylamine by a synthetic method analogous to the synthesis of compound 91. An 8.5% yield was obtained for the title compound.

Spectral analysis of the product was consistent with compound 93: $^1H$ NMR $(CDCl_3)$:δ8.46 (2H, m), 8.07 (1H, br s), 7.53 (1H, d, J=7.8 Hz), 7.24 (1H, dd), 6.52 (2H, s), 6.41 (1H, br t), 4.48 (1H, br d), 3.81 (10H, two s and one m), 3.23 (2H, m), 2.96 (1H, br t), 2.61 (1H, t, J=7.2 Hz), 1.75 (2H, p, J=7.5 Hz). HRMS (MALDI) calculated for $C_{23}H_{33}N_4O_6S$ $(M+H^+)$ 493.2121; found 493.2101.

The sulfamide compounds of the present invention may be prepared in the manner depicted in Scheme 4 below:

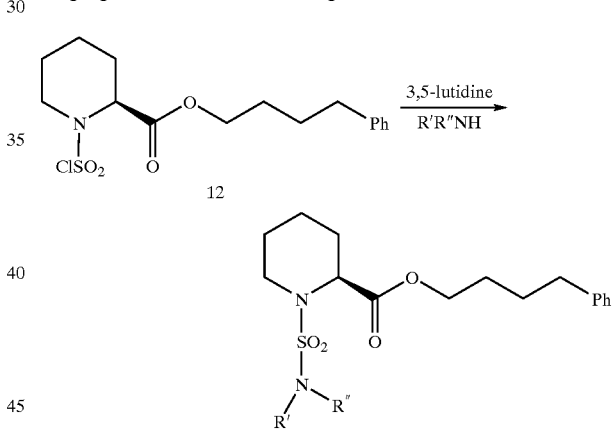

wherein R' is H, OH, and methyl;

R" is hydrogen, 4-methoxyphenyl, phenyl, 3,5-dimethoxyphenyl, 3-nitro-4-methoxyphenyl, 3-amino-4-methoxyphenyl,

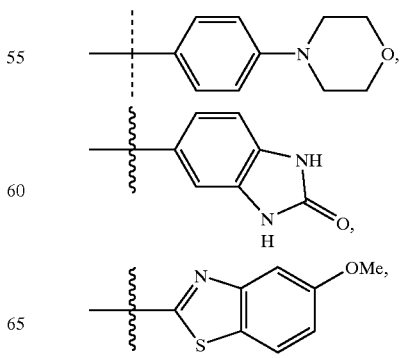

-continued

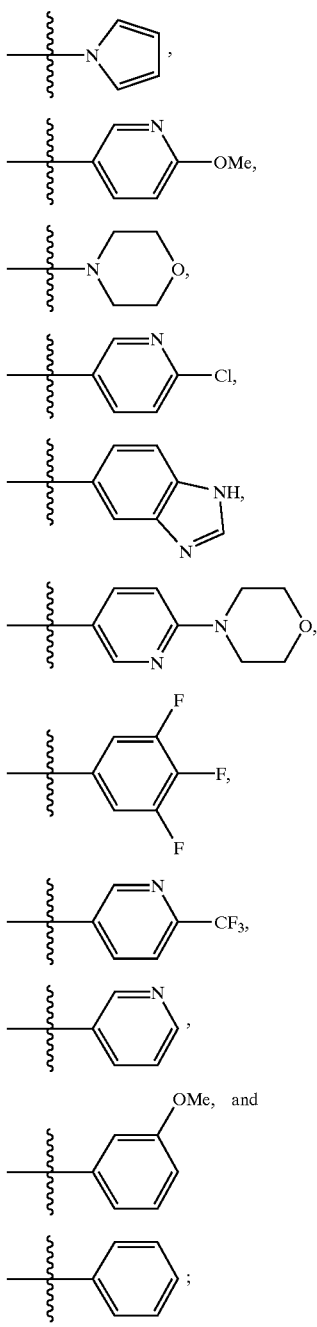

R' and R" can form

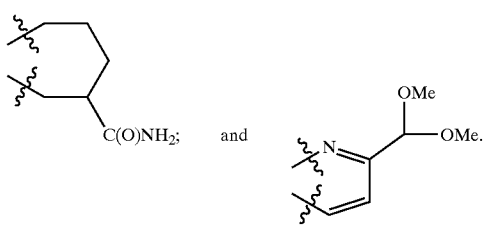

The following compounds were prepared according to Scheme 4 depicted above:

Example 26

Synthesis of piperidine-2S-carboxylic acid 4-phenyl-butyl ester (Compound 11)

Step 1: Synthesis of piperidine-1,2S-dicarboxylic acid 1-tert-butyl ester 2S-(4-phenyl-butyl) ester (compound 10):

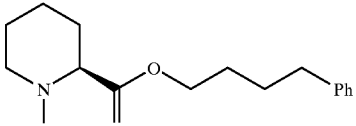

Compound 10 was prepared analogous to Example 1—Step 3.

Step 2: Synthesis of piperidine-2S-carboxylic acid 4-phenyl-butyl ester (compound 11):

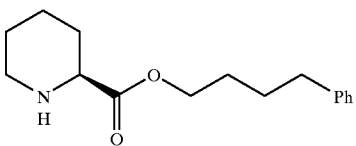

Method I: Compound 10 was treated with trifluoroacetic acid at 25° C., affording compound 11 in 90% yield.

Method II: To a CH$_2$Cl$_2$ solution (80 mL) of (S)-(1)-1-(carbobenzyloxy)-2-piperidincarboxylic acid (12.8 g, 48.6 mmol) and 1-phenyl-butan-4-ol (8.6 mL, 55.9 mmol) were added EDC (14 g, 72.9 mmol) and DMAP (2 g, 16.5 mmol) at 25° C. After 20 hours, the suspension was diluted with 120 mL of Et$_2$O, washed with brine (2×100 mL), dried over MgSO$_4$ and concentrated. The crude oil was passed through a pad of silica gel (5% EtOAc in hexanes) to provide 18 g (94% yield) of colorless oil, which was dissolved in 100 mL of EtOH. The solution was added 10% Pd on carbon (1 g) and kept under hydrogen atmosphere (1 atm) for 20 hours. The catalyst was filtered off. After removal of solvent in vacuo, 12.5 g of brown oil was obtained (~98% yield).

Example 27

Synthesis of 1-(3,4,5-Trimethoxy-phenylsulfamoyl)-piperidine-2S-carboxylic acid 4-phenyl-butyl ester (Compound 25) and 1-Sulfamoyl-piperidine-2S-carboxylic acid 4-phenyl-butyl ester (Compound 41)

Step 1: Synthesis of 1-chlorosulfonyl-piperidine-2S-carboxylic acid 4-phenyl-butyl ester (compound 12):

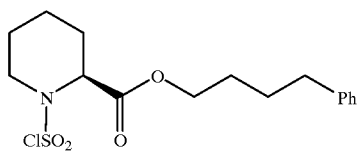

Compound 12 was prepared analogous to Example 1—Step 5.

Step 2: Synthesis of 1-(3,4,5-Trimethoxy-phenylsulfamoyl)-piperidine-2S-carboxylic acid 4-phenyl-butyl ester (compound 25) and 1-Sulfamoyl-piperidine-2S-carboxylic acid 4-phenyl-butyl ester (compound 41):

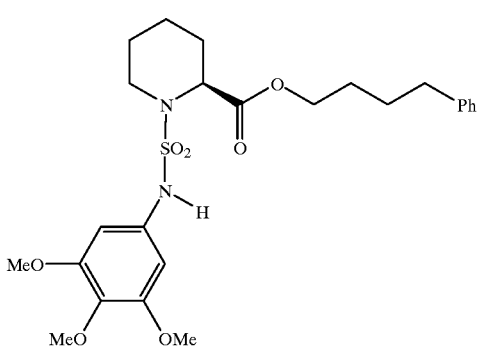

25

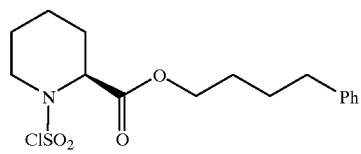

Compound 12 was prepared analogous to Example 1—Step 5.

Step 2: Synthesis of (S)-1-(4-morpholin-4-yl-phenylsulfamoyl)-piperidine-2-carboxylic 4-phenyl-butyl ester (compound 42):

41

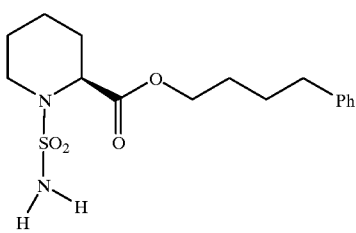

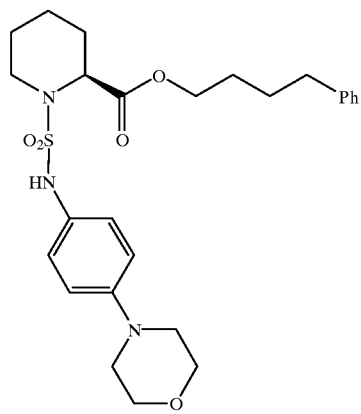

Method I: Compound 25 was prepared from compound 12 by a synthetic method analogous to Example 3—Step 6. Compound 25 was obtained in 13% yield. Compound 41 was also isolated from the reaction in 32% yield.

Spectral analysis of the product was consistent with compound 25: $^1$H NMR (CDCl$_3$):δ7.3–7.1 (6H, m), 6.42 (2H, s), 4.69 (1H, m), 4.2–4.1 (1H, m), 3.78 (6H, s), 3.76 (3H, s), 3.63 (1H, d, J=12.8 Hz), 3.02 (1H, td, J=12.8, 3 Hz), 2.6 (2H, m), 2.19 (1H, d, J=12 Hz). MS (FAB): 506 (M$^+$). HRMS (FAB): calculated for C$_{25}$H$_{34}$N$_2$O$_7$SCs (M+Cs$^+$) 639.1141; found 639.1124. Analysis for C$_{25}$H$_{34}$N$_2$O$_7$S: calculated. C 59.27% H 6.76% N 5.53% S 6.33%; found C 59.35% H 6.79% N 5.54% S 6.34%.

Spectral analysis of the product was consistent with compound 41: $^1$H NMR (CDCl$_3$): δ7.35–7.1 (5H, m), 4.90 (2H, br s), 4.72 (1H, m), 4.15 (2H, m), 3.63 (1H, br d, J=11.5 Hz), 3.00 (1H, td, J=11.8, 3.3 Hz), 2.65 (2H, m), 2.27 (2H, d, J=13.5 Hz).

Method II: To a 3,5-lutidine solution (1 mL) of 3,4,5-trimethoxyaniline (176 mg, 0.96 mmol) was added compound 12 (115 mg, 0.32 mmol) in CH$_2$Cl$_2$ (1 mL) at 25° C. After 20 hours, the mixture was diluted with EtOAc (200 mL) and washed with 5% HCl solution (ice-cold, 1×50 mL) and brine (1×50 mL). The solution was dried over MgSO$_4$ and concentrated. The residue was purified by column chromatography (25–30% EtOAc in hexanes) to provide 165 mg (quantitative) of compound 25 as a white solid.

Example 28

Synthesis of (S)-1-(4-morpholin-4-yl-phenylsulfamoyl)-piperidine-2-carboxylic 4-phenyl-butyl ester (Compound 42)

Step 1: Synthesis of 1-chlorosulfonyl-piperidine-2S-carboxylic acid 4-phenyl-butyl ester (compound 12):

Compound 42 was prepared from compound 12 by a synthetic method analogous to the method II of compound 25 synthesis. A 25% yield was obtained.

Spectral analysis of the product was consistent with compound 42: $^1$H NMR (CDCl$_3$): δ7.35–7.1 (7H, m), 6.93 (1H, s), 6.86 (2H, d, J=8.5 Hz), 4.72 (1H, m), 4.21 (2H, m), 3.85 (4H, m), 3.61 (1H, br d), 3.15–3 (5H, m), 2.65 (2H, m), 2.21 (1H, br d). HRMS (MALDI): calculated for C$_{26}$H$_{35}$N$_3$O$_5$S (M$^+$) 501.2292; found 501.2314.

Example 29

Synthesis of 1-[(4-methoxy-phenyl)-methyl-sulfamoyl]-piperidine-2S-carboxylic acid 4-phenyl-butyl ester (Compound 43)

Step 1: Synthesis of 1-chlorosulfonyl-piperidine-2S-carboxylic acid 4-phenyl-butyl ester (compound 12):

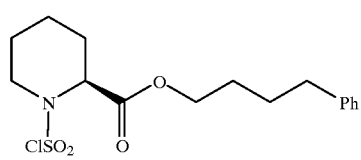

Compound 12 was prepared analogous to Example 1—Step 5.

Step 2: Synthesis of 1-[(4-Methoxy-phenyl)-methyl-sulfamoyl]-piperidine-2S-carboxylic acid 4-phenyl-butyl ester (compound 43):

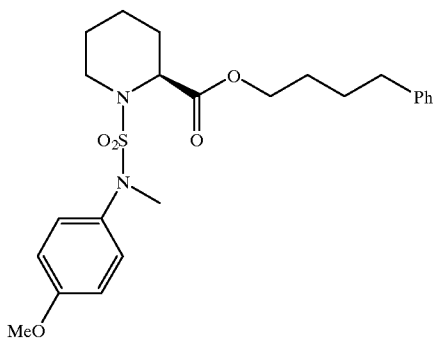

Compound 43 was prepared from compound 12 by a synthetic method analogous to the method II of compound 25 synthesis. A 95% yield was obtained.

Spectral analysis of the product was consistent with compound 43: $^1$H NMR (CDCl$_3$): δ7.4–7.1 (7H, m), 6.86 (2H, d, J=9 Hz), 4.46 (1H, m), 4.16 (2H, m), 3.79 (3H, s), 3.56 (1H, br d), 3.30 (1H, td, J=12.8, 3 Hz), 3.16 (3H, s), 2.64 (2H, m), 2.08 (1H, br d). HRMS (MALDI): calculated for C$_{24}$H$_{32}$N$_2$O$_5$SNa (M+Na$^+$) 483.1924; found 483.1913.

Example 30

Synthesis of 1-(Methyl-phenyl-sulfamoyl)-piperidine-2S-carboxylic acid 4-phenyl-butyl ester (Compound 44)

Step 1: Synthesis of 1-chlorosulfonyl-piperidine-2S-carboxylic acid 4-phenyl-butyl ester (compound 12):

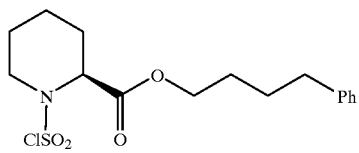

Compound 12 was prepared analogous to Example 1—Step 5.

Step 2: Synthesis of 1-(Methyl-phenyl-sulfamoyl)-piperidine-2S-carboxylic acid 4-phenyl-butyl ester (compound 44):

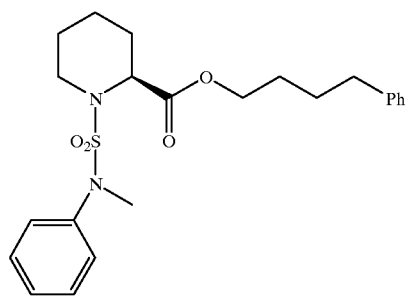

Compound 44 was prepared from compound 12 by a synthetic method analogous to the method II of compound 25 synthesis. A 49% yield was obtained.

Spectral analysis of the product was consistent with compound 44: $^1$H NMR (CDCl$_3$): δ7.4–7.1 (10H, m), 4.47 (1H, d, J=4.8 Hz), 4.16 (2H, m), 3.56 (1H, br d), 3.33 (1H, dd, J=12, 3 Hz), 3.24 (1H, dd), 3.21 (3H, s), 2.64 (2H, m), 2.07 (1H, m). HRMS (MALDI): calculated for C$_{23}$H$_{30}$N$_2$O$_4$SNa (M+Na$^+$) 453.1818; found 453.1803.

Example 31

Synthesis of 1-(2-Oxo-2,3-dihydro-1H-benzoimidazol-5-ylsulfamoyl)-piperidine-2-carboxylic acid 4-phenyl-butyl ester (Compound 45)

Step 1: Synthesis of 1-chlorosulfonyl-piperidine-2S-carboxylic acid 4-phenyl-butyl ester (compound 12):

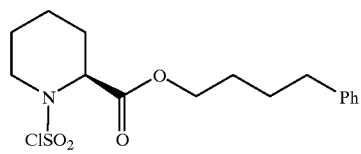

Compound 12 was prepared analogous to Example 1—Step 5.

Step 2: Synthesis of 1-(2-Oxo-2,3-dihydro-1H-benzoimidazol-5-ylsulfamoyl)-piperidine-2-carboxylic acid 4-phenyl-butyl ester (compound 45):

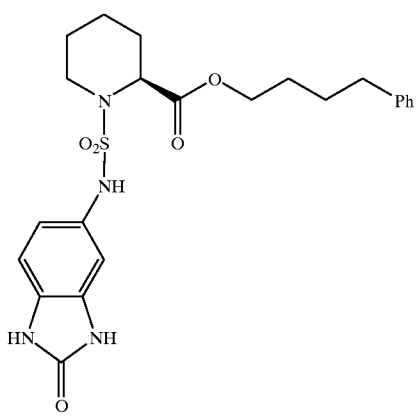

Compound 45 was prepared from compound 12 by a synthetic method analogous to the method II of compound 25 synthesis. A 70% yield was obtained.

Spectral analysis of the product was consistent with compound 45: $^1$H NMR (CDCl$_3$): δ7.35–6.8 (8H, m), 4.75 (1H, m), 4.22 (2H, m), 3.66 (1H, m), 3.08 (1H, br t), 2.66 (2H, m), 2.24 (1H, br d). HRMS (MALDI): calculated for C$_{23}$H$_{28}$N$_4$O$_5$S (M$^+$) 472.1775; found 472.1784.

Example 32

Synthesis of 1-(6-Methoxy-benzothiazol-2-ylsulfamoyl)-piperidine-2S-carboxylic acid 4-phenyl-butyl ester (Compound 46)

Step 1: Synthesis of 1-chlorosulfonyl-piperidine-2S-carboxylic acid 4-phenyl-butyl ester (compound 12):

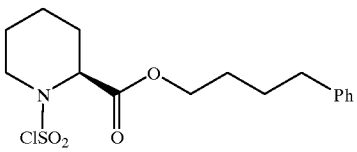

Compound 12 was prepared analogous to Example 1—Step 5.

Step 2: Synthesis of 1-(6-Methoxy-benzothiazol-2-ylsulfamoyl)-piperidine-2S-carboxylic acid 4-phenyl-butyl ester (compound 46):

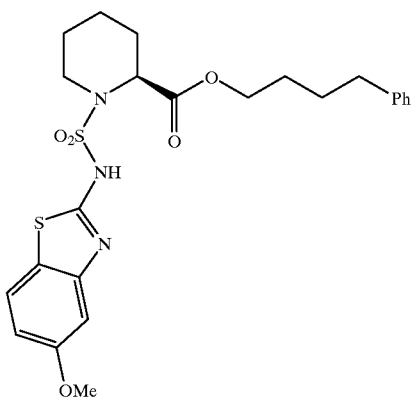

Compound 46 was prepared from compound 12 by a synthetic method analogous to the method II of compound 25 synthesis. A 2% yield was obtained.

Spectral analysis of the product was consistent with compound 46: $^1$H NMR (CDCl$_3$): δ7.55 (1H, br s), 7.35–7.1 (6H, m), 6.78 (1H, m), 6.71 (1H, dd, J=9.5, 3 Hz), 4.68 (1H, br s), 4.08 (2H, m), 3.78 (3H, s), 3.73 (1H, m), 3.39 (1H, td, J=12.8, 2.6 Hz), 2.63 (2H, m), 2.13 ($_1$H, d, J=14 Hz). HRMS (MALDI): calculated for C$_{24}$H$_{30}$N$_3$O$_5$S$_2$ (M+H$^+$) 504.1621; found 501.1623.

Example 33

Synthesis of 1-(Pyrrol-1-ylsulfamoyl)-piperidine-2S-carboxylic acid 4-phenylbutyl ester (Compound 47)

Step 1: Synthesis of 1-chlorosulfonyl-piperidine-2S-carboxylic acid 4-phenyl-butyl ester (compound 12):

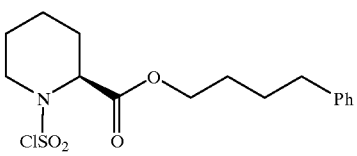

Compound 12 was prepared analogous to Example 1—Step 5.

Step 2: Synthesis of 1-(Pyrrol-1-ylsulfamoyl)-piperidine-2S-carboxylic acid 4-phenylbutyl ester (compound 47):

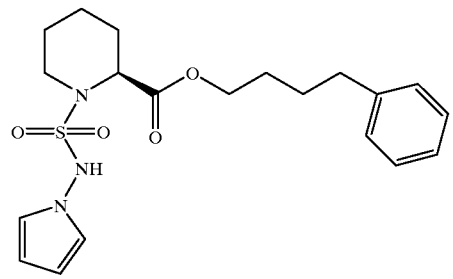

Compound 47 was prepared from compound 12 by a synthetic method analogous to the method II of compound 25 synthesis. A 90% yield was obtained.

Spectral analysis of the product was consistent with compound 47: $^1$H NMR (CDCl$_3$): δ7.60 (1H, s), 7.35–7.1 (6H, m), 6.85 (2H, t, J=2.5 Hz), 6.12 (2H, t, J=2.5 Hz), 4.59 (1H, m), 4.21 (2H, m), 3.69 (1H, br d), 3.19 (1H, td, J=12.7, 3 Hz), 2.65 (2H, m), 2.22 (1H, br d). HRMS (MALDI): calculated for C$_{20}$H$_{27}$N$_3$O$_4$SNa (M+Na$^+$) 428.1614; found 428.1632.

Example 34

Synthesis of 1-(3,5-Dimethoxy-phenylsulfamoyl)-piperidine-2S-carboxylic acid 4-phenyl-butyl ester (Compound 48)

Step 1: Synthesis of 1-chlorosulfonyl-piperidine-2S-carboxylic acid 4-phenyl-butyl ester (compound 12):

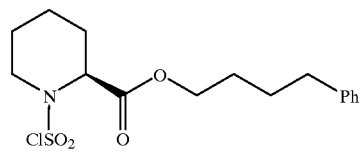

Compound 12 was prepared analogous to Example 1—Step 5.

Step 2: Synthesis of 1-(3,5-Dimethoxy-phenylsulfamoyl)-piperidine-2S-carboxylic acid 4-phenyl-butyl ester (compound 48):

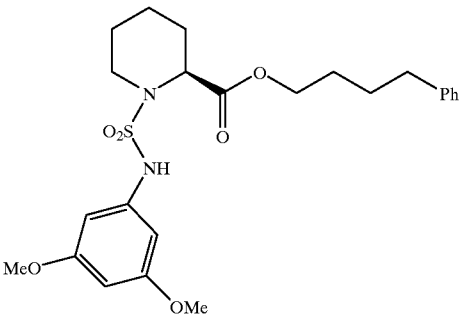

Compound 48 was prepared from compound 12 by a synthetic method analogous to the method II of compound 25 synthesis. A 95% yield was obtained.

Spectral analysis of the product was consistent with compound 48: $^1$H NMR (CDCl$_3$): δ7.3–7.1 (5H, m), 6.40 (2H, d, J=2.3 Hz), 6.21 (1H, t, J=2.3 Hz), 5.29 (1H, br s), 4.75 (1H, m), 4.19 (2H, m), 3.77 (6H, s), 3.68 (1H, br d), 3.10 (1H, td, J=12.8, 3 Hz), 2.65 (2H, m), 2.24 (1H, br d). HRMS (MALDI): calculated for $C_{24}H_{33}N_2O_6S$ (M+H$^+$) 477.2054; found 477.2070.

Example 35

Synthesis of 1-(6-methoxy-pyridin-3-ylsulfamoyl)-piperidine-2S-carboxylic acid 4-phenyl-butyl ester (Compound 49)

Step 1: Synthesis of 1-chlorosulfonyl-piperidine-2S-carboxylic acid 4-phenyl-butyl ester (compound 12):

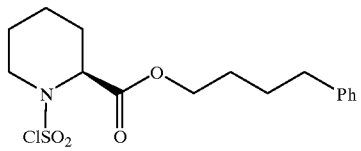

Compound 12 was prepared analogous to Example 1—Step 5.
Step 2: Synthesis of 1-(6-Methoxy-pyridin-3-ylsulfamoyl)-piperidine-2S-carboxylic acid 4-phenyl-butyl ester (compound 49):

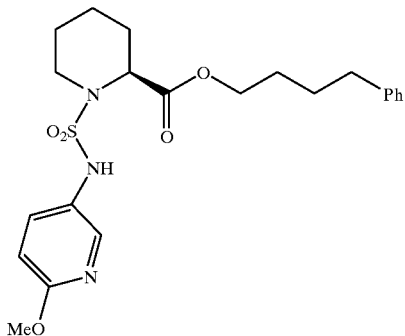

Compound 49 was prepared from compound 12 by a synthetic method analogous to the method II of compound 25 synthesis. A 96% yield was obtained.

Spectral analysis of the product was consistent with compound 49: $^1$H NMR (CDCl$_3$): δ8.07 (1H, d, J=2.7 Hz), 7.60 (1H, dd, J=8.7, 2.7 Hz), 7.3–7.15 (5H, m), 7.02 (1H, br s), 6.71 (1H, d, J=9.3 Hz), 4.72 (1H, m), 4.21 (2H, m), 3.91 (3H, s), 3.63 (1H, br d), 3.07 (1H, td, J=12.6, 3.6 Hz), 2.66 (2H, m), 2.25 (1H, br d). HRMS (MALDI): calculated for $C_{22}H_{29}N_3O_5SNa$ (M+Na$^+$) 470.1720; found 470.1742.

Example 36

Synthesis of 1-(Piperidin-1-ylsulfamoyl)-piperidine-2S-carboxylic acid 4-phenyl-butyl ester (Compound 50)

Step 1: Synthesis of 1-chlorosulfonyl-piperidine-2S-carboxylic acid 4-phenyl-butyl ester (compound 12):

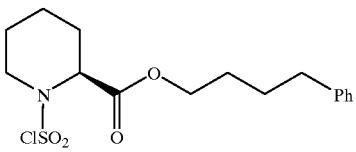

Compound 12 was prepared analogous to Example 1—Step 5.
Step 2: Synthesis of 1-(Piperidin-1-ylsulfamoyl)-piperidine-2S-carboxylic acid 4-phenyl-butyl ester (compound 50):

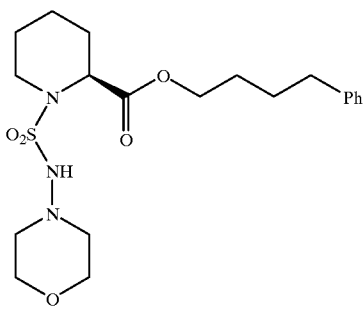

Compound 50 was prepared from compound 12 by a synthetic method analogous to the method II of compound 25 synthesis. A 15% yield was obtained.

Spectral analysis of the product was consistent with compound 50: $^1$H NMR (CDCl$_3$): δ7.35–7.1 (5H, m), 4.54 (1H, d, J=4.8 Hz), 4.19 (2H, m), 3.64 (5H, m), 3.32 (1H, td, J=12.9, 3 Hz), 3.17 (4H, m), 2.65 (2H, m), 2.17 (1H, br d).

Example 37

Synthesis of 1-(3-Carbamoyl-piperidine-1-sulfonyl)-piperidine-2S-carboxylic acid 4-phenyl-butyl ester (Compound 51)

Step 1: Synthesis of 1-chlorosulfonyl-piperidine-2S-carboxylic acid 4-phenyl-butyl ester (compound 12):

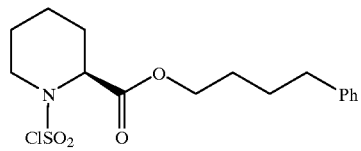

Compound 12 was prepared analogous to Example 1—Step 5.
Step 2: Synthesis of 1-(3-Carbamoyl-piperidine-1-sulfonyl)-piperidine-2S-carboxylic acid 4-phenyl-butyl ester (compound 51):

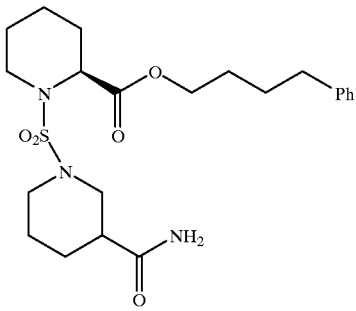

Compound 51 was prepared from compound 12 by a synthetic method analogous to the method II of compound 25 synthesis. A 75% yield was obtained.

Spectral analysis of the product was consistent with compound 51: $^1$H NMR (CDCl$_3$): (two diastereomers) δ7.35–7.1 (5H, m), 6.06 and 5.94 (1H, br s), 5.60 (1H, br s), 4.53 (1H, m), 4.18 (2H, m), 3.7–3.2 (4H, m), 3.1–2.8 (2H, m), 2.65 (2H, m), 2.45 (1H, m), 2.16 (1H, d, J=13.2 Hz). HRMS (MALDI): calculated for C$_{22}$H$_{33}$N$_3$O$_5$SNa (M+Na$^+$) 474.2033; found 474.2046.

Example 38

Synthesis of (S)-1-(6-Chloro-pyridin-3-ylsulfamoyl)-piperidine-2-carboxylic acid 4-phenyl-butyl ester (Compound 52)

Step 1: Synthesis of 1-chlorosulfonyl-piperidine-2S-carboxylic acid 4-phenyl-butyl ester (compound 12):

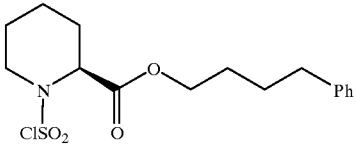

Compound 12 was prepared analogous to Example 1—Step 5.

Step 2: Synthesis of (S)-1-(6-Chloro-pyridin-3-ylsulfamoyl)-piperidine-2-carboxylic acid 4-phenyl-butyl ester (compound 52):

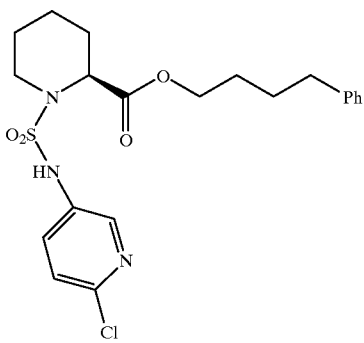

Compound 52 was prepared from compound 12 by a synthetic method analogous to the method II of compound 25 synthesis. A 96% yield was obtained.

Spectral analysis of the product was consistent with compound 52: $^1$H NMR (CDCl$_3$): δ8.22 (1H, d, J=3 Hz), 7.7–7.65 (2H, m), 7.3–7.15 (6H, m), 4.77 (1H, br s), 4.23 (2H, m), 3.63 (1H, br s), 3.10 (1H, td, J=12.6, 3 Hz), 2.66 (2H, m), 2.29 (1H, br d). HRMS (MALDI): calculated for C$_{21}$H$_{26}$N$_3$ClO$_4$SNa (M+Na$^+$) 474.1225; found 474.1208.

Example 39

Synthesis of 1-(3-Dimethoxymethyl-pyrazole-1-sulfonyl)-peperidine-2-carboxyic acid 4-phenyl-butyl ester (Compound 53)

Step 1: Synthesis of 1-chlorosulfonyl-piperidine-2S-carboxylic acid 4-phenyl-butyl ester (compound 12):

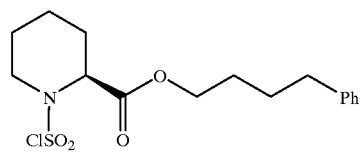

Compound 12 was prepared analogous to Example 1—Step 5.

Step 2: Synthesis of 1-(3-Dimethoxymethyl-pyrazole-1-sulfonyl)-peperidine-2-carboxyic acid 4-phenyl-butyl ester (compound 53):

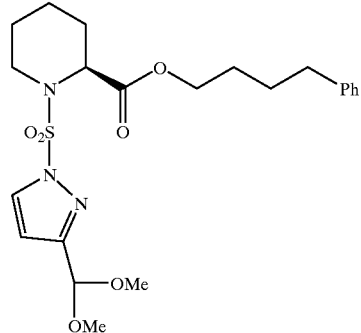

Compound 53 was prepared from compound 12 by a synthetic method analogous to the method II of compound 25 synthesis. A 94% yield was obtained (with 10% regioisomer).

Spectral analysis of the product was consistent with compound 53: $^1$H NMR (CDCl$_3$): δ7.81 (1H, d, J=2.7 Hz), 7.3–7.0 (5H, m), 6.37 (1H, d, J=2.7 Hz), 5.35 (1H, br s), 4.73 (1H, d, J=5.4 Hz), 4.03 (2H, m), 3.84 (1H, br s), 3.32 (6H, s), 2.57 (1H, br t), 204 (1H, br d). HRMS (MALDI): calculated for C$_{22}$H$_{31}$N$_3$O$_6$SNa (M+Na$^+$) 488.1826; found 488.1826.

Example 40

Synthesis of (S)-1-[(4-Methoxy-3-nitro-phenyl)-methyl-sulfamoyl]-piperidine-2-carboxylic acid 4-phenyl-butyl ester (Compound 54)

Step 1: Synthesis of 1-chlorosulfonyl-piperidine-2S-carboxylic acid 4-phenyl-butyl ester (compound 12):

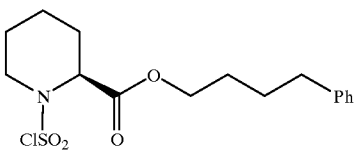

Compound 12 was prepared analogous to Example 1—Step 5.

Step 2: Synthesis of (S)-1-[(4-Methoxy-3-nitro-phenyl)-methyl-sulfamoyl]-piperidine-2-carboxylic acid 4-phenyl-butyl ester (compound 54):

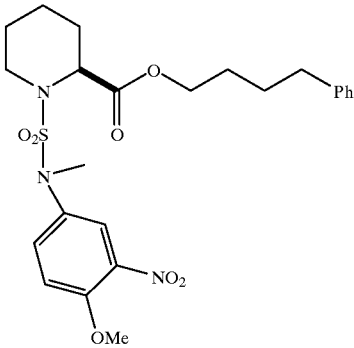

Compound 54 was prepared from compound 12 by a synthetic method analogous to the method 11 of compound 25 synthesis. A 68% yield was obtained.

Spectral analysis of the product was consistent with compound 54: $^1$H NMR (CDCl$_3$): δ7.65 (1H, dd, J=9, 2.7 Hz), 7.30–7.15 (6H, m), 7.07 (1H, d, J=9 Hz), 4.50 (1H, d, J=5 Hz), 4.20 (2H, m), 3.98 (3H, s), 3.59 (1H, br d), 3.35 (1H, td, J=13.2, 2.7 Hz), 3.22 (3H, s), 2.66 (2H, m), 2.15 (1H, br d). HRMS (MALDI): calculated for C$_{24}$H$_{31}$N$_3$O$_7$SNa (M+Na$^+$) 528.1775; found 528.1794.

Example 41

Synthesis of (S)-1-[(3-Amino-4-methoxy-phenyl)-methyl-sulfamoyl]-piperidine-2-carboxylic acid 4-phenyl-butyl ester (Compound 55)

Step 1: Synthesis of (S)-1-[(4-methoxy-3-nitro-phenyl)-methyl-sulfamoyl]-piperidine-2-carboxylic acid 4-phenyl-butyl ester (compound 54):

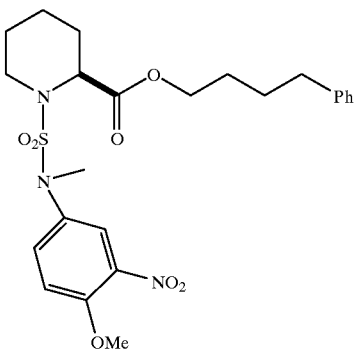

Compound 54 was prepared analogous to Example 40—Step 2.

Step 2: Synthesis of (S)-1-[(3-Amino-4-methoxy-phenyl)-methyl-sulfamoyl]-piperidine-2-carboxylic acid 4-phenyl-butyl ester (compound 55):

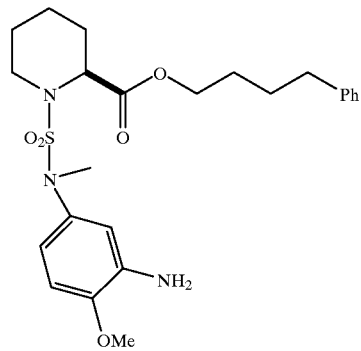

A mixture of compound 54 (55 mg) and 10% Pd on carbon (12 mg) in ethanol (2 mL) was kept under hydrogen atmosphere (1 atm) for 2 hours. The catalyst was filtered off and the filtrate was concentrated. The residue was purified by column chromatography (30% EtOAc) in hexanes) to give a clear syrup (40 mg, 77% yield).

Spectral analysis of the product was consistent with compound 55: $^1$H NMR (CDCl$_3$): δ7.5–7.25 (5H, m), 6.97–6.8 (3H, m), 4.66 (1H, d, J=4.8 Hz), 4.34 (2H, m), 4.00 (3H, s), 3.76 (1H, m), 3.48 (1H, td, J=13, 3 Hz), 3.30 (3H, s), 2.81 (2H, m), 2.25 (2H, br d). HRMS (MALDI): calculated for C$_{24}$H$_{33}$N$_3$O$_5$SNa (M+Na$^+$) 498.2033; found 498.2010.

Example 42

Synthesis of (S)-1-(3H-Benzoimidazol-5-ylsulfamoyl)-piperidine-2-carboxylic acid 4-phenyl-butyl ester (Compound 56)

Step 1: Synthesis of 1-chlorosulfonyl-piperidine-2S-carboxylic acid 4-phenyl-butyl ester (compound 12):

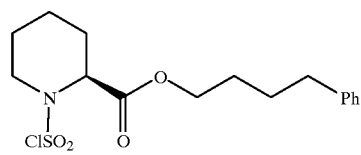

Compound 12 was prepared analogous to Example 1—Step 5.

Step 2: Synthesis of (S)-1-(3H-Benzoimidazol-5-ylsulfamoyl)-piperidine-2-carboxylic acid 4-phenyl-butyl ester (compound 56):

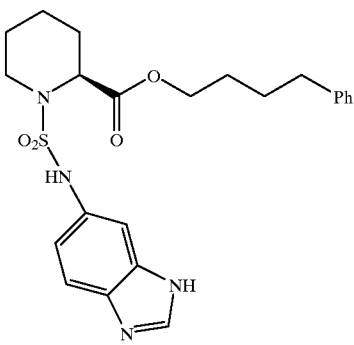

Compound 56 was prepared from compound 12 by a synthetic method analogous to the method II of compound 25 synthesis. A 14% yield was obtained.

Spectral analysis of the product was consistent with compound 56: $^1$H NMR (CDCl$_3$): δ8.09 (1H, s), 7.51 (1H, d, J=8.4 Hz), 7.35–7 (5H, m), 6.75 (1H, dd, J=9.3, 2.1 Hz), 4.78 (1H, d, J=4.7 Hz), 4–3.6 (5H, m), 3.33 (1H, td, J=13.2, 3.3 Hz), 2.60 (2H, t, J=7.2 Hz), 2.17 (1H, br d). HRMS (MALDI): calculated for C$_{23}$H$_{29}$N$_4$O$_4$S (M+H$^+$) 457.1904; found 457.1920.

Example 43

Synthesis of (S)-1-(6-Morpholin-4-yl-pyridin-3-ylsulfamoyl)-piperidine-2-carboxylic acid 4-phenyl-butyl ester (Compound 94)

Step 1: Synthesis of 1-chlorosulfonyl-piperidine-2S-carboxylic acid 4-phenyl-butyl ester (compound 12):

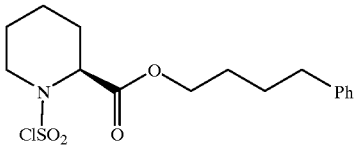

Compound 12 was prepared analogous to Example 1—Step 5.

Step 2: Synthesis of (S)-1-(6-Morpholin-4-yl-pyridin-3-ylsulfamoyl)-piperidine-2-carboxylic acid 4-phenyl-butyl ester (compound 94):

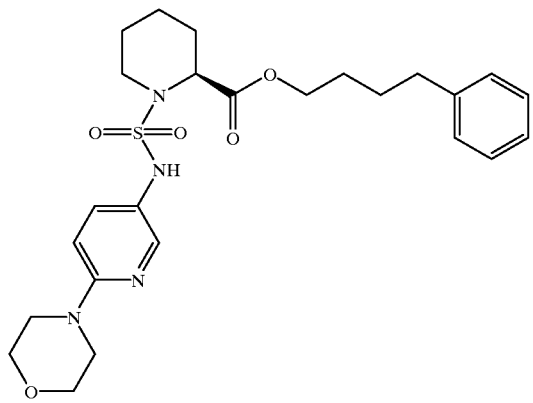

Compound 94 was prepared from the sulfamoyl chloride (compound 12) and 6-morpholin-4-yl-pyridin-3-ylamine by a synthetic method analogous to the method II of compound 25 synthesis. During the work-up of the reaction, concentrated cupric sulfate solution instead of HCl solution was used to wash off 3,5-lutidine. A 99% yield was obtained for the title compound.

Spectral analysis of the product was consistent with compound 94: $^1$H NMR (CDCl$_3$): δ8.12 (1H, d, J=2.7 Hz), 7.54 (1H, dd, J=9, 3 Hz), 7.32–7.24 (2H, m), 7.23–7.14 (3H, m), 6.50 (1H, s), 6.59 (1H, d, J=9.3 Hz), 4.70 (1H, m), 4.21 (2H, m), 3.81 (4H, t, J=5.1 Hz), 3.61 (1H, br d), 3.46 (1H, t, J=5.1 Hz), 3.09 (1H, td, J=12.6, 3.3 Hz), 2.65 (2H, m), 2.23 (1H, m). HRMS (MALDI) calculated for C$_{25}$H$_{35}$N$_4$O$_5$S (M+H$^+$) 503.2323; found 503.2313.

Example 44

Synthesis of (S)-1-(3,4,5-Trifluoro-phenylsulfamoyl)-piperidine-2-carboxylic acid 4-phenyl-butyl ester (Compound 95)

Step 1: Synthesis of 1-chlorosulfonyl-piperidine-2S-carboxylic acid 4-phenyl-butyl ester (compound 12):

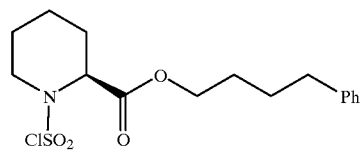

Compound 12 was prepared analogous to Example 1—Step 5.

Step 2: Synthesis of (S)-1-(3,4,5-Trifluoro-phenylsulfamoyl)-piperidine-2-carboxylic acid 4-phenyl-butyl ester (compound 95):

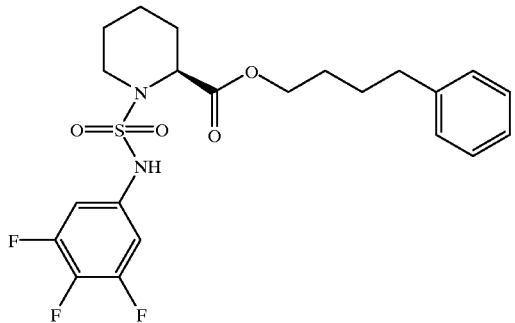

Compound 95 was prepared from the sulfamoyl chloride (compound 12) and 3,4,5-trifluoro-phenylamine by a synthetic method analogous to the method II of compound 25 synthesis. A 46% yield was obtained for the title compound.

Spectral analysis of the product was consistent with compound 95: $^1$H NMR (CDCl$_3$): δ7.61 (1H, s), 7.33–7.13 (5H, m), 6.96–6.83 (2H, m), 4.76 (1H, br d), 4.23 (2H, m), 3.64 (1H, br d), 3.00 (1H, td, J=12.6, 3.3 Hz), 2.66 (2H, m), 2.29 (1H, m). HRMS (MALDI) calculated for C$_{22}$H$_{25}$N$_2$O$_4$SNa (M+Na$^+$) 493.1379; found 493.1393.

Example 45

Synthesis of (S)-1-(6-Trifluoromethyl-pyridin-3-ylsulfamoyl)-piperidine-2-carboxylic acid 4-phenyl-butyl ester (Compound 96)

Step 1: Synthesis of 1-chlorosulfonyl-piperidine-2S-carboxylic acid 4-phenyl-butyl ester (compound 12):

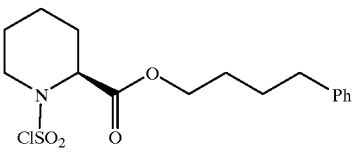

Compound 12 was prepared analogous to Example 1—Step 5.

Step 2: Synthesis of (S)-1-(6-Trifluoromethyl-pyridin-3-ylsulfamoyl)-piperidine-2-carboxylic acid 4-phenyl-butyl ester (compound 96):

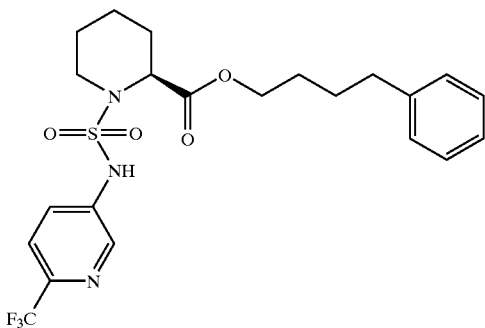

Compound 96 was prepared from the sulfamoyl chloride (compound 12) and 6-trifluoromethyl-pyridin-3-ylamine by a synthetic method analogous to the method II of compound 25 synthesis. During the work-up of the reaction, concentrated cupric sulfate solution instead of HCl solution was used to wash off 3,5-lutidine. An 11% yield was obtained for the title compound.

Spectral analysis of the product was consistent with compound 96: $^1$H NMR (CDCl$_3$): δ8.47 (1H, d, J=2.7 Hz), 8.04 (1H, br s), 7.82 (1H, dd, J=8.7, 2.7 Hz), 7.61 (1H, d, J=8.4 Hz), 7.33–7.14 (5H, m), 4.80 (1H, br d), 4.25 (2H, m), 3.67 (1H, br d), 3.00 (1H, td, J=12.3, 3.3 Hz), 2.67 (2H, m), 2.32 (1H, m). HRMS (MALDI) calculated for C$_{22}$H$_{27}$F$_3$N$_3$O$_4$S (M+H$^+$) 486.1669; found 486.1667.

Example 46

Synthesis of (S)-1-(Pyridin-3-ylsulfamoyl)-piperidine-2-carboxylic acid 4-phenylbutyl ester (Compound 97)

Step 1: Synthesis of 1-chlorosulfonyl-piperidine-2S-carboxylic acid 4-phenyl-butyl ester (compound 12):

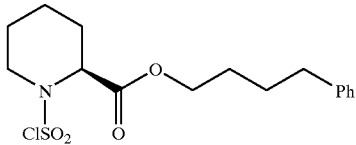

Compound 12 was prepared analogous to Example 1—Step 5.

Step 2: Synthesis of (S)-1-(Pyridin-3-ylsulfamoyl)-piperidine-2-carboxylic acid 4-phenyl-butyl ester (compound 97):

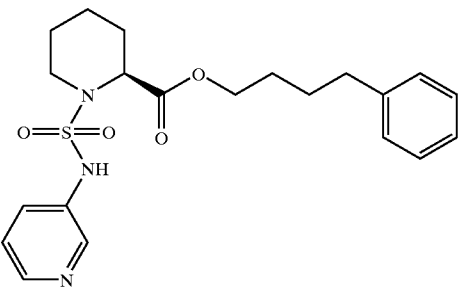

Compound 97 was prepared from the sulfamoyl chloride (compound 12) and 3-amino-pyridine by a synthetic method analogous to the method II of compound 25 synthesis. During the work-up of the reaction, concentrated cupric sulfate solution instead of HCl solution was used to wash off 3,5-lutidine. A 69% yield was obtained for the title compound.

Spectral analysis of the product was consistent with compound 97: $^1$H NMR (CDCl$_3$): δ8.45 (1H, d, J=2.7 Hz), 8.35 (1H, dd, J=4.8, 1.5 Hz), 7.75–7.66 (2H, m), 7.33–7.14 (6H, m), 4.77 (1H, br d), 4.23 (2H, m), 3.64 (1H, br d), 3.05 (1H, td, J=12.9, 3.3 Hz), 2.66 (2H, m), 2.27 (1H, m). HRMS (MALDI) calculated for C$_{21}$H$_{27}$N$_3$O$_4$SNa (M+Na$^+$) 440.1614; found 440.1597.

Example 47

Synthesis of (S)-1-(4-Carboxy-3-methoxy-phenylsulfamoyl)-piperidine-2-carboxylic acid 4-phenyl-butyl ester (Compound 98)

Step 1: Synthesis of 1-chlorosulfonyl-piperidine-2S-carboxylic acid 4-phenyl-butyl ester (compound 12):

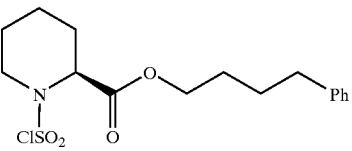

Compound 12 was prepared analogous to Example 1—Step 5.

Step 2: Synthesis of (S)-1-(4-Carboxy-3-methoxy-phenylsulfamoyl)-piperidine-2-carboxylic acid 4-phenyl-butyl ester (compound 98):

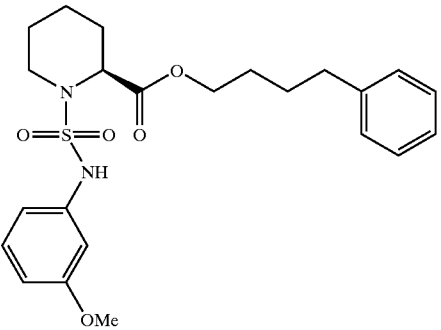

Compound 98 was prepared from the sulfamoyl chloride (compound 12) and 4-amino-2-methoxy-benzoic acid by a synthetic method analogous to the method 11 of compound 25 synthesis. The carboxylate was lost as carbon dioxide during the reaction. Therefore, a 74% yield was obtained for the title compound.

Spectral analysis of the product was consistent with compound 98: $^1$H NMR (CDCl$_3$): δ7.34–7.11 (7H, m), 6.83–6.72 (2H, m), 6.64 (1H, br ddd), 4.74 (1H, br d), 4.20 (2H, m), 3.79 (3H, s), 3.66 (1H, br d), 3.10 (1H, td, J=12.9, 3.3 Hz), 2.65 (2H, m), 2.22 (1H, m). LCMS 445 (M–H). HRMS (MALDI) calculated for C$_{23}$H$_{31}$N$_2$O$_5$S (M+H$^+$) 447.1954; found 447.1938.

Example 48

Synthesis of (S)-1-(Hydroxy-phenyl-sulfamoyl)-piperidine-2-carboxylic acid 4-phenyl-butyl ester (Compound 99)

Step 1: Synthesis of 1-chlorosulfonyl-piperidine-2S-carboxylic acid 4-phenyl-butyl ester (compound 12):

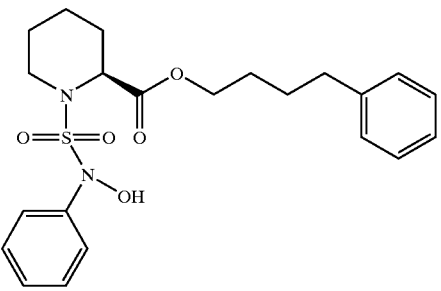

Compound 99 was prepared from the sulfamoyl chloride (compound 12) and N-phenyl-hydroxylamine by a synthetic method analogous to the method II of compound 25 synthesis. A 55% yield was obtained for the title compound.

Spectral analysis of the product was consistent with compound 99: $^1$H NMR (CDCl$_3$): δ8.13 (1H, s), 7.43 (2H, d, J=8.1 Hz), 7.33–7.04 (7H, m), 4.72 (1H, br d), 4.18 (2H, m), 3.96 (1H, br d), 3.35 (1H, td, J=12.6, 3.3 Hz), 2.58 (2H, m), 2.17 (1H, m). LCMS 431 (M–H), 433 (M+H$^+$).

The bis-benzyl ether compounds of the present invention may be prepared in the manner depicted in Scheme 5 below:

Scheme 5

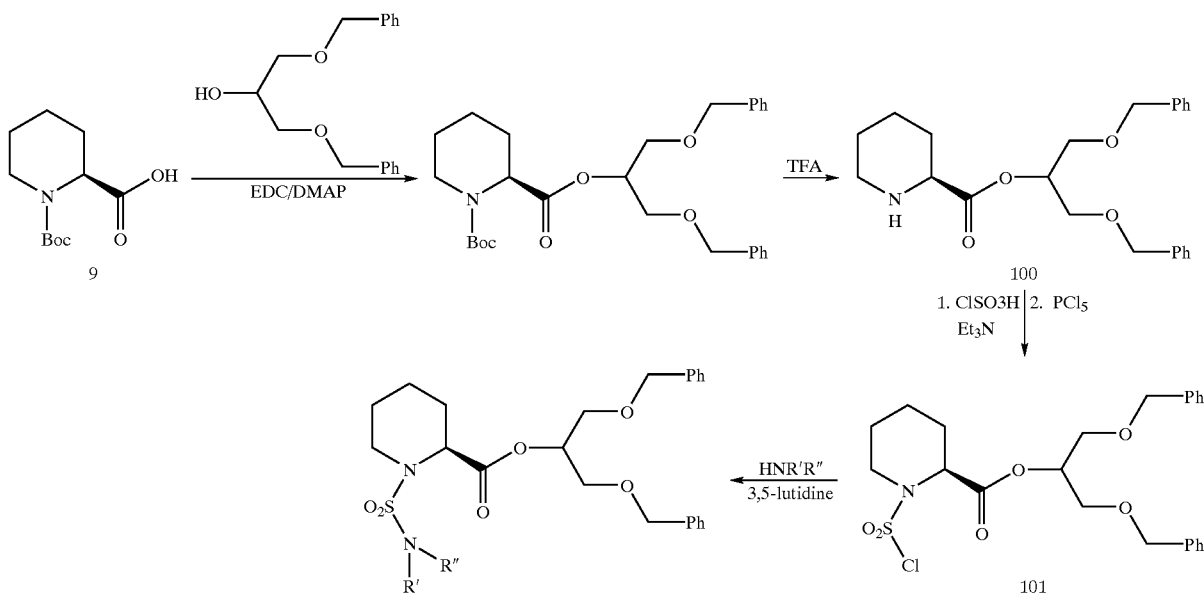

where, R' is H;

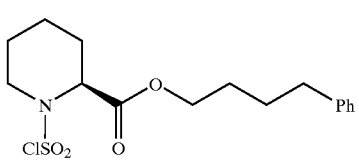

Compound 12 was prepared analogous to Example 1—Step 5.

Step 2: Synthesis of (S)-1-(Hydroxy-phenyl-sulfamoyl)-piperidine-2-carboxylic acid 4-phenyl-butyl ester (compound 99):

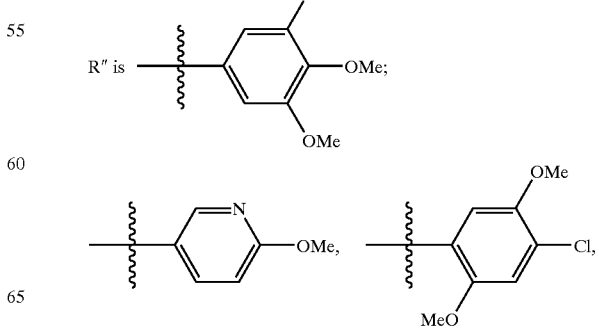

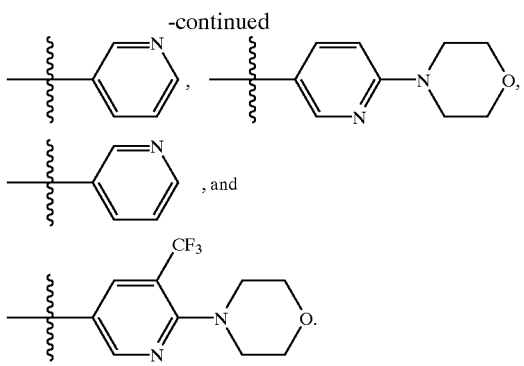

The following examples were prepared according to Scheme 5 depicted above:

Example 49

Synthesis of Compound 100

Step 1: Synthesis of piperidine-1,2S-dicarboxylic acid 1-tert-butyl ester (compound 9):

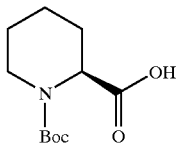

Compound 9 was prepared analogous to Example 1—Step 2.

Step 2: Synthesis of compound 100:

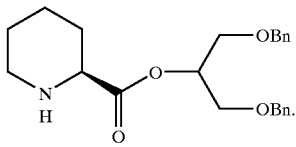

Compound 100 was prepared from the carboxylic acid (compound 9) and 1,3-bis-benzyloxy-propan-2-ol by a method analogous to the synthesis of compound 20. A 40% yield was obtained for the title compound (2 steps).

Spectral analysis of the product was consistent with compound 100: $^1$H NMR (CDCl$_3$): δ7.39–7.23 (10H, m), 5.26 (1H, p, J=5.4 Hz), 4.59–4.46 (4H, m), 3.66 (2H, s), 3.63 (2H, s), 3.39 (1H, dd, J=9, 2.7 Hz), 3.06 (1H, dt, J=12.6, 2.7 Hz), 2.65 (1H, m), 1.96 (1H, m).

Example 50

Synthesis of Compound 101

Step 1: Synthesis of compound 100:

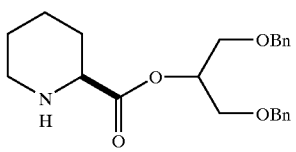

Compound 100 was prepared analogous to Example 49—Step 2.

Step 2: Synthesis of compound 101:

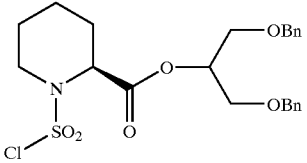

Compound 101 was prepared from the amine (compound 100) by a method analogous to the synthesis of compound 21. A 60% yield was obtained for the title compound.

Spectral analysis of the product was consistent with compound 101: $^1$H NMR (CDCl$_3$): δ7.40–7.23 (10H, m), 5.36 (1H, p, J=5.4 Hz), 4.85 (1H, br d), 4.59–4.45 (4H, m), 3.92 (1H, br d), 3.71–3.63 (4H, m), 3.56 (1H, td, J=13.2, 3.6 Hz), 2.19 (1H, br d), 1.91 (1H, m).

Example 51

Synthesis of (S)-1-(3,4,5-Trimethoxy-phenylsulfamoyl)-piperidine-2-carboxylic acid 2-benzyloxy-1-benzyloxymethyl-ethyl ester (Compound 102)

Step 1: Synthesis of compound 101:

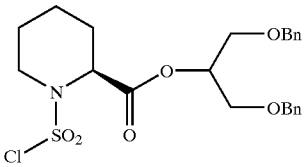

Compound 101 was prepared analogous to Example 50—Step 2.

Step 2: Synthesis of (S)-1-(3,4,5-Trimethoxy-phenylsulfamoyl)-piperidine-2-carboxylic acid 2-benzyloxy-1-benzyloxymethyl-ethyl ester (compound 102):

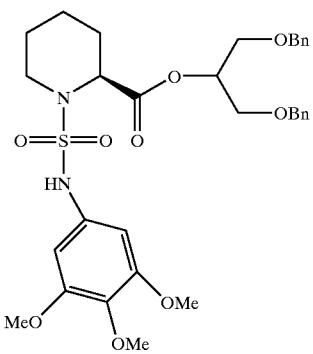

Compound 102 was prepared from the sulfamoyl chloride (compound 101) and 3,4,5-trimethoxy-phenylamine by a synthetic method analogous to the method II of compound 25 synthesis. An 81% yield was obtained for the title compound Spectral analysis of the product was consistent with compound 102: $^1$H NMR (CDCl$_3$): δ7.36–7.23 (10H, m), 7.20 (1H, br s), 6.48 (2H, s), 5.39 (1H, p, J=5.1 Hz), 4.79 (1H, br d), 4.58–4.45 (4H, m), 3.80 (3H, s), 3.80 (6 H, s), 372–3.55 (5H, m), 3.05 (1H, td, J=12.3, 4.2 Hz), 2.26 (1H, m). MS (ESP) 651 (M+Na$^+$), 627 (M–H).

Example 52

Synthesis of (S)-1-(6-Methoxy-pyidin-3-ylsulfamoyl)-piperidine-2-carboxylic acid 2-benzyloxy-1-benzyloxymethyl-ethyl ester (Compound 103)

Step 1: Synthesis of compound 101:

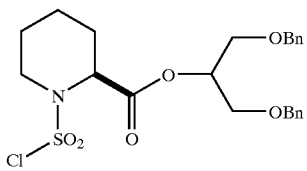

Compound 101 was prepared analogous to Example 50—Step 2.

Step 2: Synthesis of (S)-1-(6-Methoxy-pyridin-3-ylsulfamoyl)-piperidine-2-carboxylic acid 2-benzyloxy-1-benzyloxymethyl-ethyl ester (compound 103):

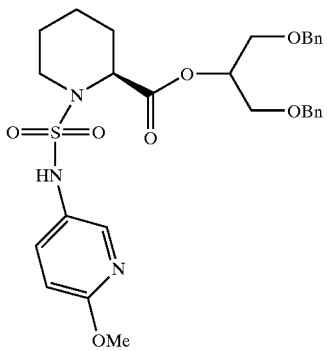

Compound 103 was prepared from the sulfamoyl chloride (compound 101) and 6-methoxy-pyridin-3-ylamine by a synthetic method analogous to the method II of compound 25 synthesis. During the work-up of the reaction, concentrated cupric sulfate solution instead of HCl solution was used to wash off 3,5-lutidine. An 85% yield was obtained for the title compound.

Spectral analysis of the product was consistent with compound 103: $^1$H NMR (CDCl$_3$): δ8.01 (1H, d, J=2.4 Hz), 7.51 (1H, dd, J=9, 2.7 Hz), 7.36–7.21 (10H, m), 7.13 (1H, s), 6.64 (1H, d, J=8.7 Hz), 5.38 (1H, p, J=5.4 Hz), 4.75 (1H, br d), 4.57–4.43 (4H, m), 3.91 (3H, s), 3.75–3.63 (4H, m), 3.52 (1H, br d), 3.00 (1H, td, J=12.3, 4.2 Hz), 2.25 (1H, m). HRMS (MALDI) calculated for $C_{29}H_{36}N_3O_7S$ (M+H$^+$) 570.2268; found 570.2289.

Example 53

Synthesis of (S)-1-(4-Chloro-2,5-dimethoxy-phenylsulfamoyl)-piperidine-2-carboxylic acid 2-benzyloxy-1-benzyloxymethyl-ethyl ester (Compound 104)

Step 1: Synthesis of compound 101:

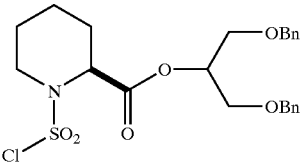

Compound 101 was prepared analogous to Example 50—Step 2.

Step 2: Synthesis of (S)-1-(4-Chloro-2,5-dimethoxy-phenylsulfamoyl)-piperidine-2-carboxylic acid 2-benzyloxy-1-benzyloxymethyl-ethyl ester (compound 104):

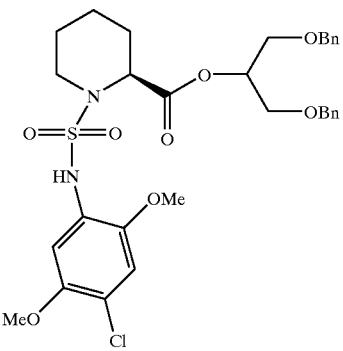

Compound 104 was prepared from the sulfamoyl chloride (compound 101) and 4-chloro-2,5-dimethoxy-phenylamine by a synthetic method analogous to the method II of compound 25 synthesis. A 99% yield was obtained for the title compound.

Spectral analysis of the product was consistent with compound 104: $^1$H NMR (CDCl$_3$): δ7.40 (1H, s), 7.36–7.22 (10H, m), 7.18 (1H, s), 6.86 (1H, s), 5.32 (1H, p, J=5.4 Hz), 4.71 (1H, br d), 4.58–4.44 (4H, m), 3.84 (3H, s), 3.75 (3H, s), 3.68–3.58 (5H, m), 3.19 (1H, td, J=12.9, 3.0Hz), 2.22 (1H, m). HRMS (MALDI) calculated for $C_{31}H_{37}ClN_2O_8SNa$ (M+Na$^+$) 655.1851; found 655.1850.

Example 54

Synthesis of (S)-1-(Pyridin-3-ylsulfamoyl)-piperidine-2-carboxylic acid 2-benzyloxy-1-benzyloxymethyl-ethyl ester (Compound 105)

Step 1: Synthesis of compound 101:

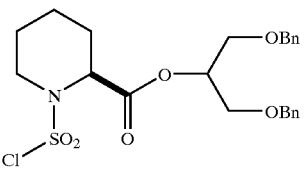

Compound 101 was prepared analogous to Example 50—Step 2.

Step 2: Synthesis of (S)-1-(Pyridin-3-ylsulfamoyl)-piperidine-2-carboxylic acid 2-benzyloxy-1-benzyloxymethyl-ethyl ester (compound 105):

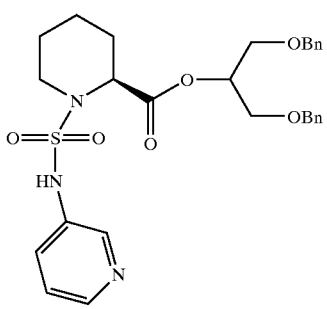

Compound 105 was prepared from the sulfamoyl chloride (compound 101) and 3-aminopyridine by a synthetic method analogous to the method II of compound 25 synthesis. During the work-up of the reaction, concentrated cupric sulfate solution instead of HCl solution was used to wash off 3,5-lutidine. A 75% yield was obtained for the title compound.

Spectral analysis of the product was consistent with compound 105: $^1$H NMR (CDCl$_3$): δ8.39 (1H, s), 8.33 (1H, s), 7.62 (1H, d, J=8.7 Hz), 7.56 (1H, s), 7.39–7.12 (11H, m), 5.40 (1H, p, J=5.4 Hz), 4.79 (1H, br d), 4.59–4.44 (4H, m), 3.76–3.62 (4H, m), 3.54 (1H, br d), 2.96 (11H, td, J=12.3, 4.5 Hz), 2.28 (1H, d). HRMS (MALDI) calculated for $C_{28}H_{34}N_3O_6S$ (M+H$^+$) 540.2163; found 540.2186.

Example 55

Synthesis of (S)-1-(6-Morpholin-4-yl-pyridin-3-ylsulfamoyl)-piperidine-2-carboxylic acid 2-benzyloxy-1-benzyloxymethyl-ethyl ester (Compound 106)

Step 1: Synthesis of compound 101:

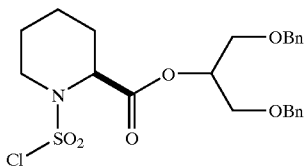

Compound 101 was prepared analogous to Example 50—Step 2.

Step 2: Synthesis of (S)-1-(6-Morpholin-4-yl-pyridin-3-ylsulfamoyl)-piperidine-2-carboxylic acid 2-benzyloxy-1-benzyloxymethyl-ethyl ester (compound 106):

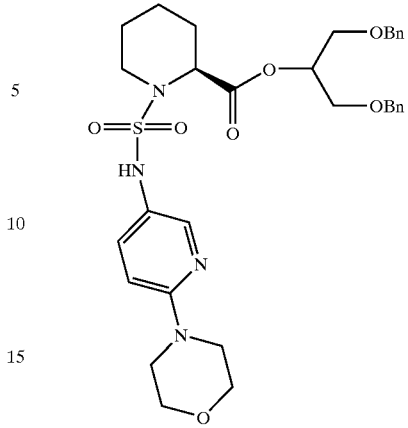

Compound 106 was prepared from the sulfamoyl chloride (compound 101) and 6-morpholin-4-yl-pyridin-3-ylamine by a synthetic method analogous to the method II of compound 25 synthesis. During the work-up of the reaction, concentrated cupric sulfate solution instead of HCl solution was used to wash off 3,5-lutidine. A 26% yield was obtained for the title compound.

Spectral analysis of the product was consistent with compound 106: $^1$H NMR (CDCl$_3$): δ8.08 (1H, d, J=2.4 Hz), 7.47 (1H, dd, J=9, 3 Hz), 7.37–7.22 (10H, m), 7.00 (1H, s), 6.54 (1H, d, J=9 Hz), 5.38 (1H, p, J=5.1 Hz), 4.75 (1H, br d), 4.57–4.44 (4H, m), 3.81 (4H, t, J=4.8 Hz), 3.75–3.63 (4H, m), 3.54 (1H, br d), 3.46 (4H, t, J=4.8 Hz), 3.02 (1H, td, J=12.3, 4.2 Hz), 2.25 (1H, br d). HRMS (MALDI) calculated for $C_{32}H_{40}N_4O_7SNa$ (M+Na$^+$) 647.2510; found 647.2495.

Example 56

Synthesis of (S)-1-(6-Methyl-pyridin-3-ylsulfamoyl)-piperidine-2-carboxylic acid 2-benzyloxy-1-benzyloxymethyl-ethyl ester (Compound 107)

Step 1: Synthesis of compound 101:

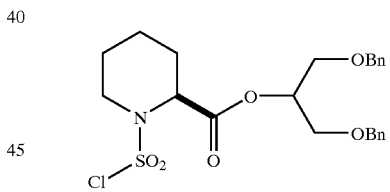

Compound 101 was prepared analogous to Example 50—Step 2.

Step 2: Synthesis of (S)-1-(6-Methyl-pyridin-3-ylsulfamoyl)-piperidine-2-carboxylic acid 2-benzyloxy-1-benzyloxymethyl-ethyl ester (compound 107):

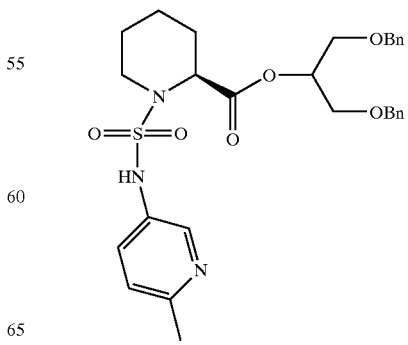

Compound 107 was prepared from the sulfamoyl chloride (compound 101) and 6-methyl-pyridin-3-ylamine by a synthetic method analogous to the method II of compound 25 synthesis. During the work-up of the reaction, concentrated cupric sulfate solution instead of HCl solution was used to wash off 3,5-lutidine. A 78% yield was obtained for the title compound.

Spectral analysis of the product was consistent with compound 107: $^1$H NMR (CDCl$_3$): δ7.52 (1H, dd, J=8.4, 2.7 Hz), 7.48 (1H, br s), 7.36–7.21 (10H, m), 7.04 (1H, d, J=8.7 Hz), 5.39 (1H, p, J=5.4 Hz), 4.76 (1H, br d), 4.57–4.43 (4H, m), 3.75–3.62 (4H, m), 3.53 (1H, br d), 2.99 (1H, dd, J=12, 3.6 Hz), 2.50 (3H, s), 2.25 (1H, br d). HRMS (MALDI) calculated for $C_{29}H_{36}N_3O_6S$ (M+H$^+$) 554.2319; found 554.2298.

Example 57

Synthesis of (S)-1-(Morpholin-4-yl-trifluoromethyl-pyridin-3-ylsulfamoyl)-piperidine-2-carboxylic acid 2-benzyloxy-1-benzyloxymethyl-ethyl ester (Compound 108)

Step 1: Synthesis of compound 101:

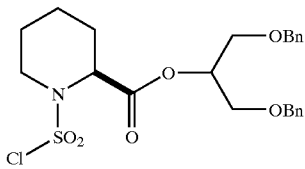

Compound 101 was prepared analogous to Example 50—Step 2.

Step 2: Synthesis of (S)-1-(Morpholin-4-yl-trifluoromethyl-pyridin-3-ylsulfamoyl)-piperidine-2-carboxylic acid 2-benzyloxy-1-benzyloxymethyl-ethyl ester (compound 108):

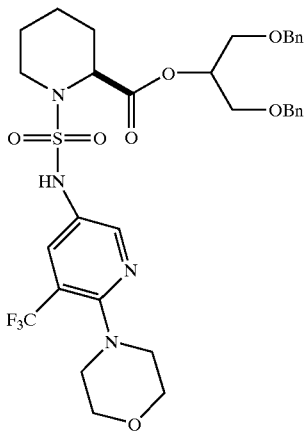

Compound 108 was prepared from the sulfamoyl chloride (compound 101) and 6-morpholin-4-yl-5-trifluoromethyl-pyridin-3-ylamine by a synthetic method analogous to the method II of compound 25 synthesis. During the work-up of the reaction, concentrated cupric sulfate solution instead of HCl solution was used to wash off 3,5-lutidine. A 70% yield was obtained for the title compound.

Spectral analysis of the product was consistent with compound 108: $^1$H NMR (CDCl$_3$): δ8.24 (1H, d, J=2.4 Hz), 7.74 (1H, d, J=2.7 Hz), 7.50 (1H, br s), 7.35–7.19 (10H, m), 5.41 (1H, p, J=6 Hz), 4.78 (1H, br d), 4.58–4.43 (4H, m), 3.82 (4H, t, J=4.5 Hz), 3.77–3.65 (4H, m), 3.52 (1H, br d), 3.20 (4H, t, J=4.8 Hz), 2.95 (1H, td, J=12.6, 4.5 Hz), 2.28 (1H, br d). HRMS (MALDI) calculated for $C_{33}H_{39}F_3N_4O_7SNa$ (M+Na$^+$) 715.2384; found 715.2375.

Compound 59 was prepared in the manner depicted in Scheme 6 below (using two methods):

Scheme 6

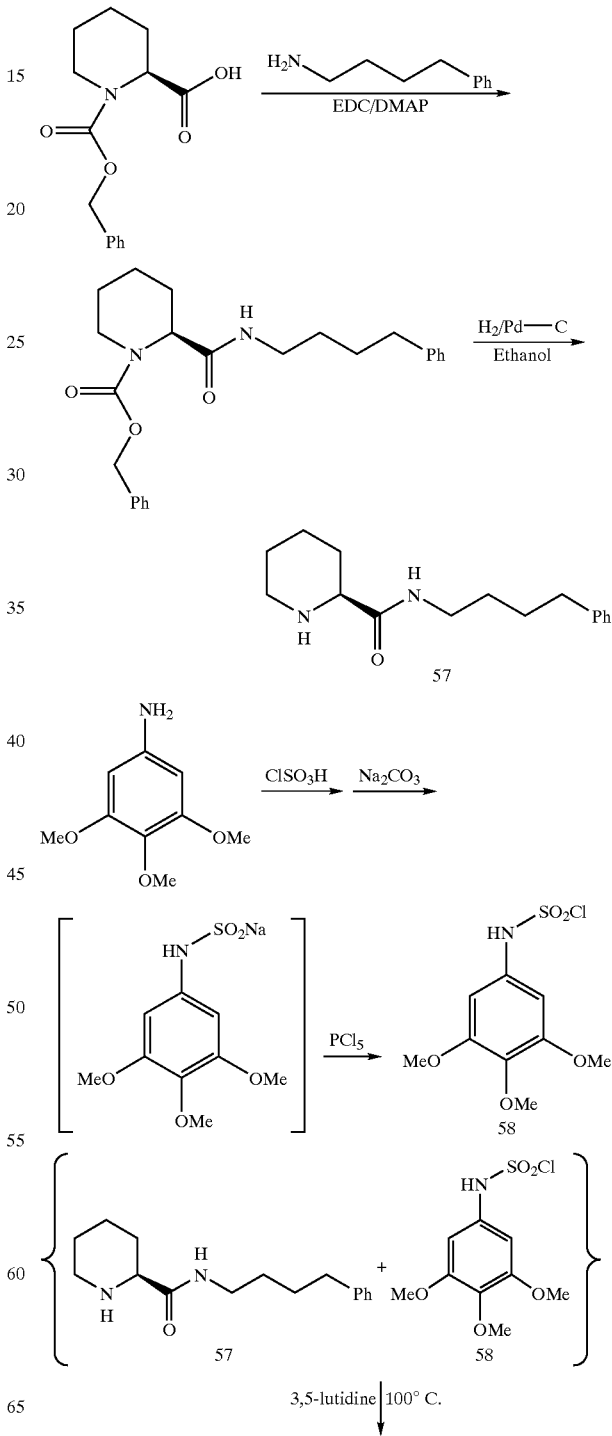

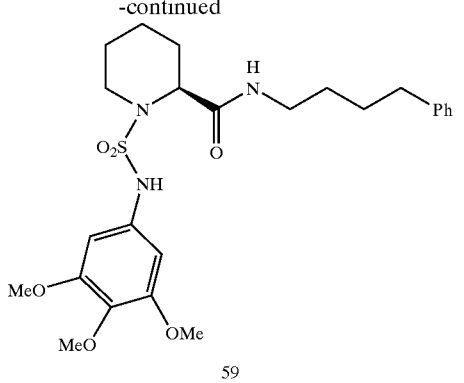

59

Method II

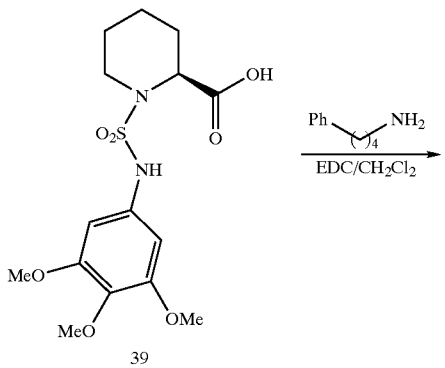

39

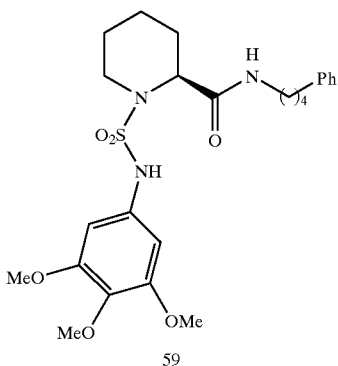

59

Example 58

Synthesis of (S)-1-(3,4,5-Trimethoxy-phenylsulfamoyl)-piperidine-2-carboxylic acid (4-phenyl-butyl)-amide (Compound 59)

Step 1: Synthesis of (S)-piperidine-2-carboxylic acid (4-phenyl-butyl)-amide (compound 57):

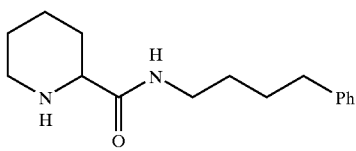

The title compound was prepared from (S)-(1)-1-(carbobenzyloxy)-2-piperidincarboxylic acid in manner analogous to that used in preparation of compound 11 (Method II) where 1-phenyl-butyan-4-amine was used instead of 1-phenyl-butan-4-ol. Compound 57 was obtained in 83% yield.

Spectral analysis of the product was consistent with compound 57: $^1$H NMR (CDCl$_3$): δ7.35–7.1 (5H, m), 6.75 (1H, br s), 3.71 (1H, q, J=6.9 Hz), 3.26 (2H, q, J=6.9 Hz), 3.17 (1H, dd), 3.013 (1H, dt, J=12, 3.6 Hz), 2.68 (1H, m), 2.63 (2H, t, J=7.2 Hz), 1.98 (1H, m).

Step 2: Synthesis of N-(3,4,5-trimethoxyphenyl) sulfamoyl chloride (compound 58):

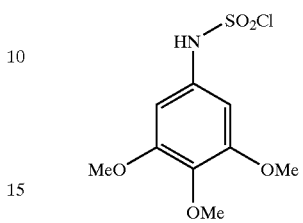

At −5° C., chlorosulfonic acid (0.22 mL, 3.33 mmol) was slowly added to a chloroform solution (10 mL) of 3,4,5-trimethoxyaniline (1.83 g, 10 mmol). After 1 hour at 25° C., the suspension was filtered, and the solid was washed with CH$_2$Cl$_2$. The residue was dissolved in Na$_2$CO$_3$ solution (0.5M, 20 mL), which was washed with ethyl ether (2×20 mL). The aqueous solution was concentrated to give a solid, which was extracted with boiling ethanol (20 mL). After evaporation of ethanol, the solid (200 mg) was treated with PCl$_5$ (200 mg) in refluxing benzene (15 mL). The precipitate was filtered off and the filtrate was concentrated. The residue was purified by column chromatography (50% EtOAc in hexanes), affording 56 mg (5% yield) of the sulfamoyl chloride as a off-white solid.

Spectral analysis of the product was consistent with compound 58: $^1$H NMR (CDCl$_3$): δ6.65 (1H, br s), 6.32 (2H, s), 3.80 (3H, s), 3.76 (6H, s).

Step 3: Synthesis of (S)-1-(3,4,5-Trimethoxy-phenylsulfamoyl)-piperidine-2-carboxylic acid (4-phenyl-butyl)-amide (compound 59):

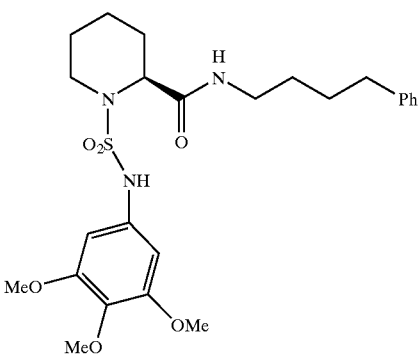

Method I: To a 3,5-lutidine solution (2 mL) of the sulfamoyl chloride (compound 58, 56 mg, 0.17 mmol) was added compound 57 (100 mg, 0.32 mmol). After 20 hours at 100° C., the mixture was diluted with EtOAc (20 mL) and washed with 5% HCl solution (ice-cold, 1×50 mL) and brine (1×50 mL). The solution was dried over MgSO$_4$ and concentrated. The residue was purified by column chromatography (30% EtOAc in hexanes) to provide 22 mg (25%) of compound 59 as a pale-yellow oil.

Spectral analysis of the product was consistent with compound 59: $^1$H NMR (CDCl$_3$): δ7.41 (1H, s), 7.3–7.1 (5H, m), 6.48 (2H, s), 6.10 (1H, t, J=5.7 Hz), 4.49 (1H, d, J=4.5 Hz), 3.84 (6H, s), 3.81 (3H, s), 3.77 (1H, br d), 3.20 (2H, m), 2.97 (1H, td), 2.61 (2H, t, J=7.2 Hz), 2.23 (11H, d, J=13.8 Hz). HRMS (MALDI): calculated for C$_{25}$H$_{35}$N$_3$O$_6$SNa (M+Na$^+$) 528.2139; found 528.2134.

Example 59

Synthesis of (S)-1-(3,4,5-Trimethoxy-phenylsulfamoyl)-piperidine-2-carboxylic acid (4-phenyl-butyl)-amide (Compound 59)

Step 1: Synthesis of 1-(3,4,5-Trimethoxy-phenylsulfamoyl)-piperidine-2S-carboxylic acid (compound 39):

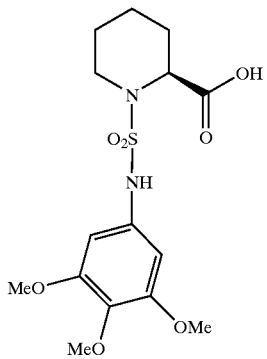

Compound 39 was prepared analogous to Example 22.

Step 2: Synthesis of (S)-1-(3,4,5-Trimethoxy-phenylsulfamoyl)-piperidine-2-carboxylic acid (4-phenyl-butyl)-amide (compound 59):

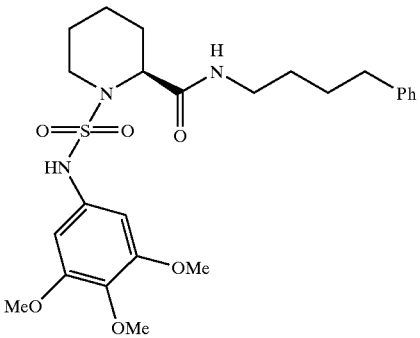

Method II: compound 59 was prepared from the carboxylic acid (compound 39) 4-phenyl-butylamine by a synthetic method analogous to the synthesis of compound 91. A 57% yield was obtained for the title compound.

Compounds 109–112 were prepared in the manner depicted in Scheme 7 below:

Scheme 7

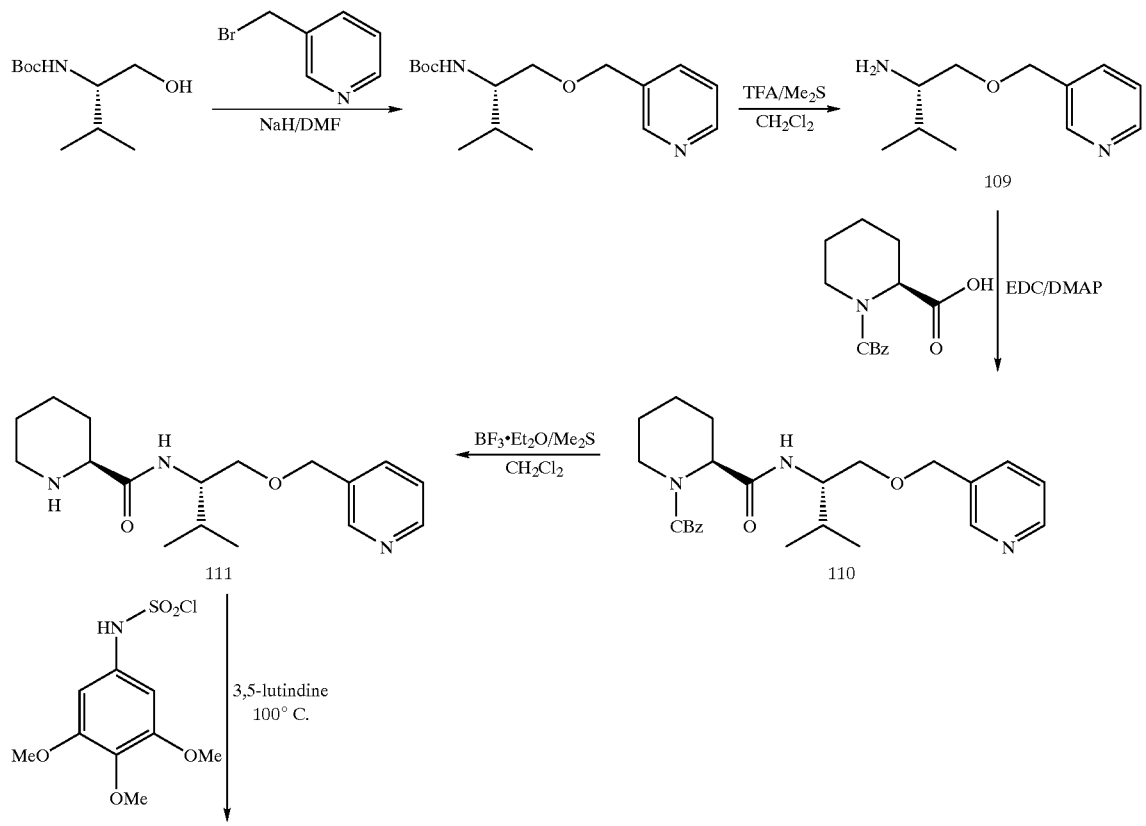

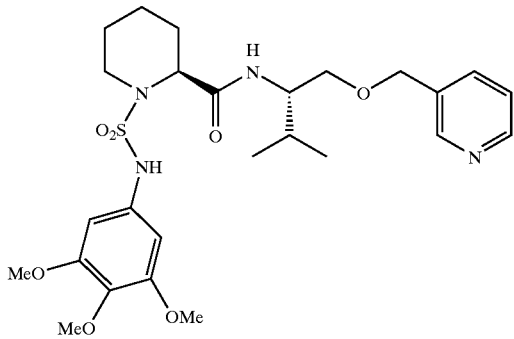

112

The following examples were prepared according to Scheme 7 depicted above:

Example 60

Synthesis of Compound 109

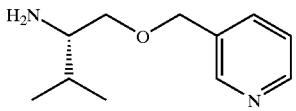

At 0° C., sodium hydride (331 mg, 13.8 mmol) was added to N-Boc-L-valinol solution (1 g, 4.92 mmol) in DMF (25 mL). After the hydrogen evolving subsided, 3-(bromomethyl)pyridine (1.87, 7.38 mmol) was introduced. At 25° C., the suspension was stirred for 48 hours and poured into ice-cold water (50 mL). The aqueous solution was extracted with $CH_2Cl_2$ (3×50 mL). Combined organic layers were washed with brine (2×50 mL), dried over $MgSO_4$ and concentrated. The residue (1.8 g) was dissolved in 2 mL of $CH_2Cl_2$. Trifluoroacetic acid (2 mL) was added slowly at 0° C. After 10 hours at 25° C., LCMS indicated no reaction occurred. Methyl sulfide (1 mL) was then introduced and the mixture was stirred for 72 hours. All the solvent was removed in vacuo and the residue was redissolved in 0.5% HCl solution (10 mL). The aqueous solution was washed with ether (20 mL) and EtOAc (20 mL). The pH of the solution was then adjusted to >12 by addition of ice-cold 5% NaOH solution (5 mL). The basic solution was extracted with $CH_2Cl_2$ (3×35 mL). Combined organic layers were dried over $Na_2SO_4$ and concentrated, affording 1.03 g (>90% yield by $^1H$ NMR) of the title compound as a pale yellow oil.

Spectral analysis of the product was consistent with compound 109: $^1H$ NMR (CDCl$_3$): δ8.62–8.48 (2H, m), 7.68 (1H, d, J=7.8 Hz), 7.28 (1H, dd), 4.62–4.50 (2H, m), 3.56 (1H, dd, J=9.6, 4.2 Hz), 3.36 (1H, t, J=9 Hz), 2.81 (1H, m), 1.96 (2H, br s), 1.70 (1H, o J=6.6 Hz), 0.93 (3H, d, J=6.8 Hz), 0.93 (3H, d, J=6.7 Hz). LCMS 195 (M+H$^+$).

Example 61

Synthesis of Compound 110

Step 1: Synthesis of compound 109:

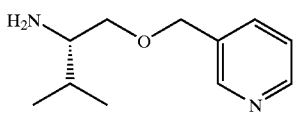

Compound 109 was prepared as in Example 60.

Step 2: Synthesis of compound 110:

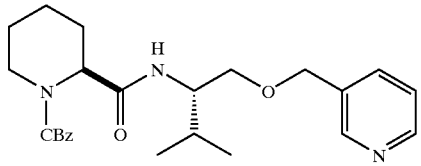

To a mixture of the (S)-(–)-1-Z-2-piperidine carboxylic acid (1 g, 3.80 mmol) and the amine (compound 109, 0.8 g, 4.12 mmol) in $CH_2Cl_2$ (5 mL) were added EDC (1.5 g, 8 mmol) and DMAP (0.15 g, 1.2 mmol) at 0° C. The solution was stirred at 25° C. for 48 hours, and was diluted with EtOAc (80 mL), washed with $H_2O$ (1×100 mL), dried and then concentrated to give 1.4 g (84% yield) of the title compound as a yellow oil.

Spectral analysis of the product was consistent with compound 110: $^1H$ NMR (CDCl$_3$) (mixture of amide rotamers): δ1.86 (1H, o, J=6.8 Hz), 0.90 (3H, d, J=6.8 Hz), 0.85 (3H, d, J=7.0 Hz). LCMS 440 (M+H$^+$), 462 (M+Na$^+$).

Example 62

Synthesis of Compound 111

Step 1: Synthesis of compound 110:

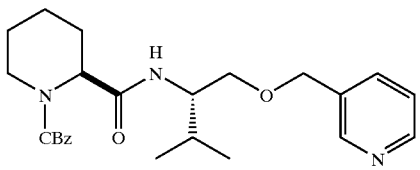

Compound 110 was prepared analogous to Example 61—Step 2.

Step 2: Synthesis of compound 111:

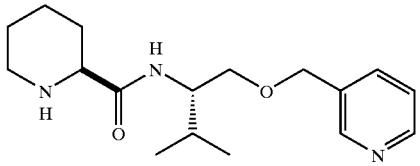

The crude oil of compound 110 (1.4 g, 3.2 mmol) was dissolved in 2 mL of $CH_2Cl_2$. Methyl sulfide (2 mL) and $BF_3$ etherate (0.5 mL) were added. The mixture was stirred at 25° C. for 20 hours and diluted with $CH_2Cl_2$ (50 mL). The solution was washed with ice-cold 10% NaOH solution (2×50 mL), dried over $MgSO_4$ and concentrated in vacuo, affording 0.62 g of the title compound (64% yield) as a light yellow oil.

Spectral analysis of the product was consistent with compound 111: $^1$H NMR ($CDCl_3$) (mixture of amide rotamers): δ two sets of signals 0.96 (3H, d, J=7 Hz) and 0.96 (3H, d, J=6.9 Hz), 0.91 (3H, d, J=7 Hz) and 0.91 (3H, d, J=7 Hz). LCMS 306 (M+H$^+$).

Example 63

Synthesis of (S)-1-(3,4,5-Trimethoxyphenylsulfamoyl)-piperidine-2-carboxylic acid [(S)-2-methyl-1-(pyridin-3-ylmethoxymethyl)-propyl]-amide (Compound 112)

Step 1: Synthesis of N-(3,4,5-trimethoxyphenyl) sulfamoyl chloride (compound 58):

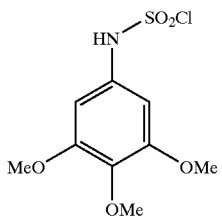

Compound 58 was prepared analogous to Example 58—Step 2.

Step 2: Synthesis of compound 111:

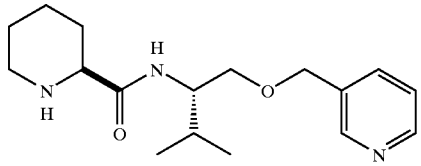

Compound 111 was prepared analogous to Example 62—Step 2.

Step 3: Synthesis of (S)-1-(3,4,5-Trimethoxyphenylsulfamoyl)-piperidine-2-carboxylic acid [(S)-2-methyl-1-(pyridin-3-ylmethoxymethyl)-propyl]-amide (compound 112):

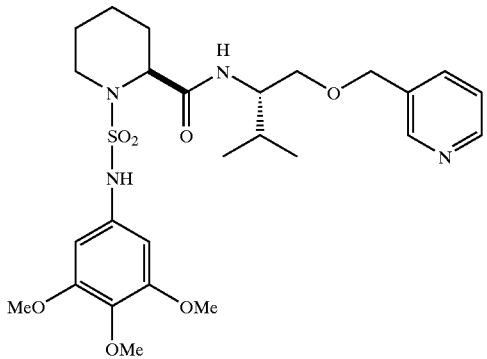

Compound 112 was prepared from the sulfamoyl chloride (compound 58) and the amine (compound 111) by a synthetic method analogous to the synthesis of compound 59. A 67% yield was obtained for the title compound.

Spectral analysis of the product was consistent with compound 112: $^1$H NMR ($CDCl_3$): δ8.77–8.31 (3H, m), 7.64 (1H, m), 7.36–7.27 (1H, m), 6.65 (1H, d J=9 Hz), 6.52 (2H, s), 4.53 (2H, AB), 4.46 (1H, br s), 3.97–3.83 (2H, m), 3.82 (6H, s), 3.81 (3H, s), 3.51–3.44 (2H, m), 3.04 (1H, br t), 2.22 (1H, br d), 0.94 (3H, d, J=6.6 Hz), 0.89 (3H, d, J=6.3 Hz). LCMS 551 (M+H$^+$), 549 (M−H).

Compounds 113–118 were prepared in the manner depicted in Scheme 8 below:

Scheme 8
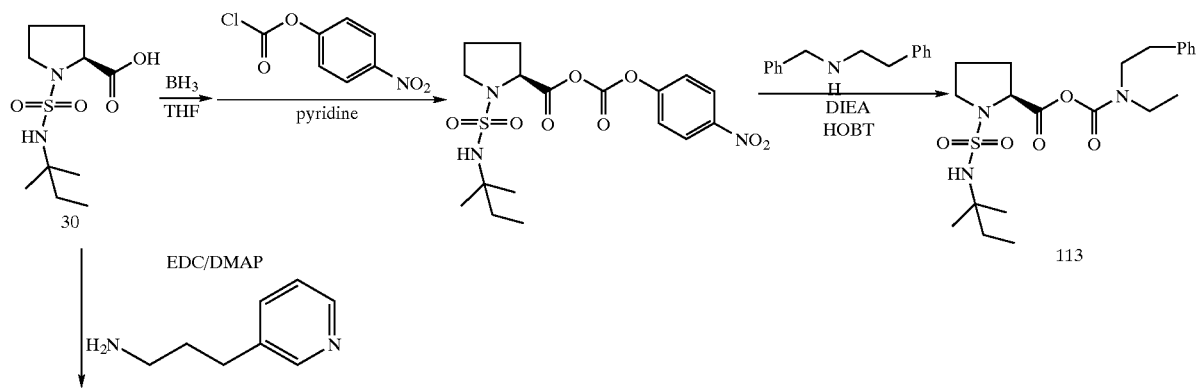
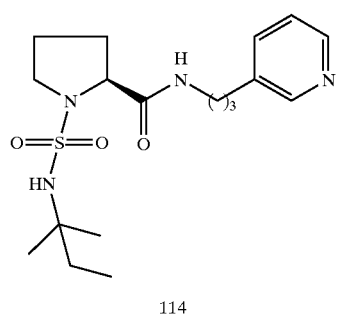
114
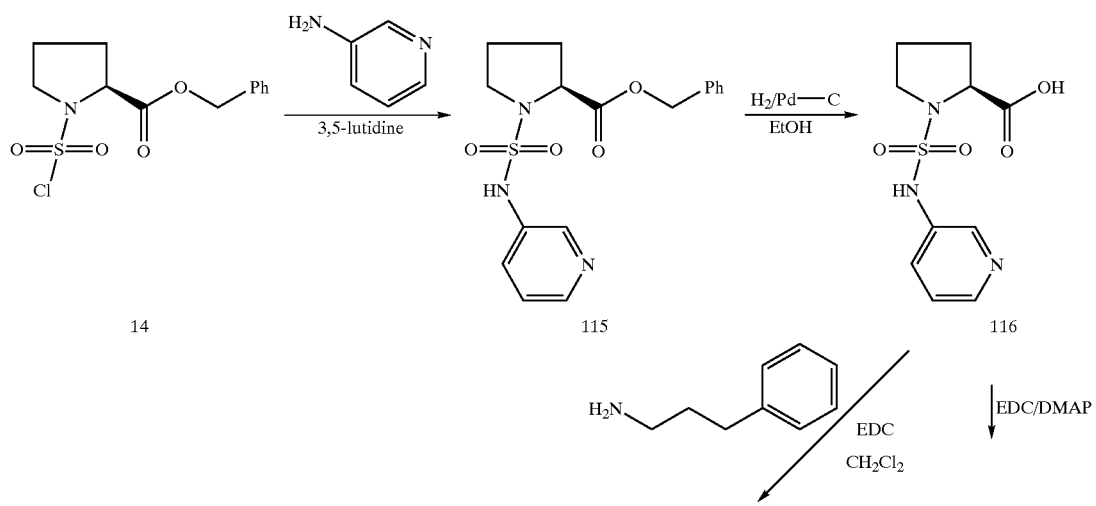

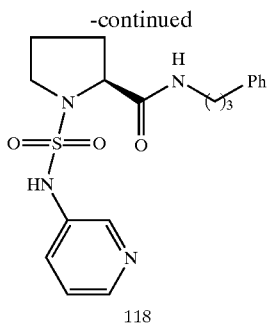

118

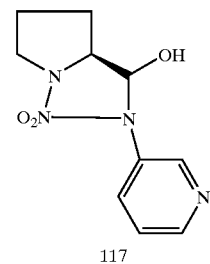

117

The following examples were prepared according to Scheme 8 depicted above:

Example 64

Synthesis of Benzyl-phenethyl-carbamic acid (S)-1-(dimethyl-propylsulfamoyl)-pyrrolidin-2-ylmethyl ester (Compound 113)

Step 1: Synthesis of 1-(1,1-Dimethyl-propylsulfamoyl)-pyrrolidine-2S-carboxylic acid (compound 30):

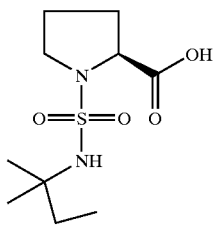

Compound 30 was prepared analogous to Example 11—Step 1.

Step 2: Synthesis of Benzyl-phenethyl-carbamic acid (S)-1-(dimethyl-propylsulfamoyl)-pyrrolidin-2-ylmethyl ester (compound 113):

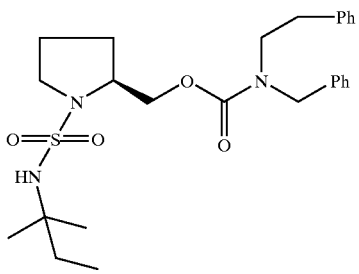

At 0° C., a borane solution in THF (1M, 0.34 mL, 0.34 mmol) was added to a THF solution (1 mL) of the carboxylic acid (compound 30, 90 mg, 0.34 mmol). The mixture was stirred at 25° C. for 16 hours. Methanol (0.5 mL) and $Na_2CO_3$ solution (saturated, 1 mL) were added to quench the reaction. The resulted suspension was stirred for 48 hours. Most of solvent was then removed in vacuo. The aqueous solution was extracted with $CH_2Cl_2$ (3×20 mL). Combined organic layers were washed with brine (25 mL), dried and concentrated. The clear oil was dissolved in $CH_2Cl_2$ (1 mL). At 0° C., pyridine (0.2 mL) and 4-nitrophenyl chloroformate (80 mg, 0.40 mmol) were introduced. The mixture was stirred at 25° C. for 15 hours, diluted with $CH_2Cl_2$ (20 mL), washed with ice-cold 3% HCl solution (20 mL), dried and concentrated. The residue was dissolved in $CH_2Cl_2$ (1 mL). Benzyl-phenylethylamine (90 mg, 0.43 mmol), 1-hydroxybenzotriazole hydrate (62 mg, 0.4 mmol) and DIEA (0.1 mL) were added at 0° C. After stirring at 25° C. for 20 hours, the mixture was diluted with EtOAc (25 mL), washed with ice-cold 2% NaOH solution (2×20 mL), 1% HCl solution (20 mL) and brine (1×20 mL), dried and concentrated. The residue was purified by column chromatography (20% EtOAc in hexanes) to give 45 mg (27% yield for three steps) of the title compound as a clear oil.

Spectral analysis of the product was consistent with compound 113: $^1H$ NMR ($CDCl_3$) (mixture of amide rotamers): δ7.36–7.04 (10H, m), 1.30 (3H, s), 1.28 (3H, s). LCMS 510 (M+Na$^+$), 489 (M–H).

Example 65

Synthesis of (S)-1-(1,1-Dimethyl-propylsulfamoyl)-pyrrolidine-2-carboxylic acid (3-pyridin-3-yl-propyl)-amide (Compound 114)

Step 1: Synthesis of 1-(1,1-Dimethyl-propylsulfamoyl)-pyrrolidine-2S-carboxylic acid (compound 30):

Compound 30 was prepared analogous to Example 11—Step 1.

Step 2: Synthesis of (S)-1-(1,1-Dimethyl-propylsulfamoyl)-pyrrolidine-2-carboxylic acid (3-pyridin-3-yl-propyl)-amide (compound 114):

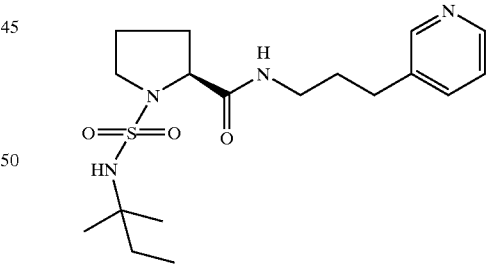

Compound 114 was prepared from the carboxylic acid (compound 30) and 3-pyridin-3-yl-propylamine by a synthetic method analogous to the Step 2 of compound 31 synthesis. A 70% yield was obtained for the title compound.

Spectral analysis of the product was consistent with compound 114: $^1H$ NMR ($CDCl_3$): δ8.48–8.40 (2H, m), 7.52 (1H, dt, J=7.8, 2.1 Hz), 7.21 (1H, dd, J=7.5, 5.1 Hz), 6.87 (1H, br t, J=5.4 Hz), 4.66 (1H, s), 4.22 (1H, dd, J=8.4, 4.5 Hz), 3.47–3.17 (3H, m), 2.66 (2H, t, J=7.5 Hz), 1.32 (3H, s), 1.31 (3H, s), 0.93 (3H, t, J=7.5 Hz). HRMS (MALDI) calculated for $C_{18}H_{30}N_4O_3SNa$ (M+Na$^+$) 405.1931; found 405.1949.

Example 66

Synthesis of (S)-1-(Pyridin-3-ylsulfamoyl)-pyrrolidine-2-carboxylic acid benzyl ester (Compound 115)

Step 1: Synthesis of 1-chlorosulfonyl-pyrrolidine-2S-carboxylic acid benzyl ester (compound 14):

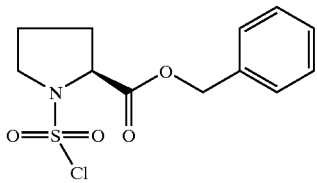

Compound 14 was prepared analogous to Example 2—Step 1.

Step 2: Synthesis of (S)-1-(Pyridin-3-ylsulfamoyl)-pyrrolidine-2-carboxylic acid benzyl ester (compound 115):

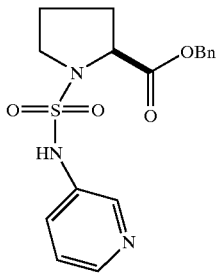

Compound 115 was prepared from the sulfamoyl chloride (compound 14) and 3-amino-pyridine by a synthetic method analogous to the method II of compound 25 synthesis. During the work-up of the reaction, concentrated cupric sulfate solution instead of HCl solution was used to wash off 3,5-lutidine. A 99% yield was obtained for the title compound.

Spectral analysis of the product was consistent with compound 115: $^1$H NMR (CDCl$_3$): δ8.44 (1H, d, J=2.7 Hz), 8.38 (1H, d, J=4.5 Hz), 7.8–7.7 (2H, m), δ 7.4–7.3 (5H, m), 7.23 (1H, dd, J=9, 5.7 Hz), 5.17 (2H, AB), 4.53 (1H, dd, 119=9, 4.5 Hz), 3.55–3.30 (2H, m), 2.34–2.2 (1H, m), 2.1–1.98 (1H, m), 1.97–1.85 (2H, m). HRMS (MALDI) calculated for C$_{17}$H$_{20}$N$_3$O$_4$S (M+H$^+$) 362.1175; found 362.1175.

Example 67

Synthesis of (S)-1-(Pyridin-3-ylsulfamoyl)-pyrrolidine-2-carboxylic acid (Compound 116)

Step 1: Synthesis of (S)-1-(Pyridin-3-ylsulfamoyl)-pyrrolidine-2-carboxylic acid benzyl ester (compound 115):

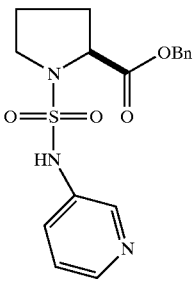

Compound 115 was prepared analogous to Example 66—Step 2.

Step 2: Synthesis of (S)-1-(Pyridin-3-ylsulfamoyl)-pyrrolidine-2-carboxylic acid (compound 116):

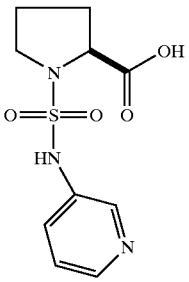

Compound 116 was prepared from the benzyl ester (compound 115) by a synthetic method analogous to compound 30 synthesis. An 89% yield was obtained for the title compound.

Spectral analysis of the product was consistent with compound 116: $^1$H NMR (CDCl$_3$): δ8.87 (1H, d, J=2.4 Hz), 8.19 (1H, br d), 8.14 (1H, br d), 7.48 (1H, dd, J=8.4, 5.1 Hz), 4.69 (1H, dd, J=8.4, 3.6 Hz), 3.68 (2H, m), 2.49–2.26 (2H, m), 2.13–2.02 (2H, m). HRMS (MALDI) calculated for C$_{10}$H$_{14}$N$_{14}$O$_4$S (M+H$^+$) 272.0705; found 272.0710.

Example 68

Synthesis of (S)-1,1-Dioxo-2-pyridin-3-yl-hexahydro-1l6-thia-2,6a-diaza-pentalen-3-one (Compound 117)

Step 1: Synthesis of (S)-1-(Pyridin-3-ylsulfamoyl)-pyrrolidine-2-carboxylic acid (compound 116):

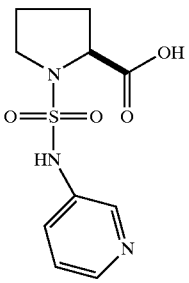

Compound 116 was prepared analogous to Example 67—Step 2.

Step 2: Synthesis of (S)-1,1-Dioxo-2-pyridin-3-yl-hexahydro-1l6-thia-2,6a-diaza-pentalen-3-one (Compound 117):

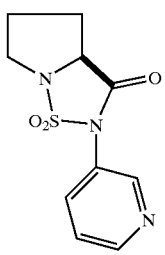

Compound 117 was prepared from compound 116 upon treatment of EDC and DMAP in $CH_2Cl_2$. An 86% yield was obtained for the title compound.

Spectral analysis of the product was consistent with compound 117: $^1$H NMR ($CDCl_3$): δ8.70 (2H, m), 7.79 (1H, m), 7.45 (1H, dd, J=8.4, 4.8 Hz), 6.53 (1H, br s), 4.66 (1H, dd, J=8.4, 3.6 Hz), 4.01–3.90 (1H, m), 3.6–3.49 (1H, m), 2.58–2.34 (2H, m), 2.13–1.91 (2H, m). HRMS (MALDI) calculated for $C_{10}H_{12}N_3O_3S$ (M+H$^+$) 254.0599; found 254.0609.

Example 69

Synthesis of (S)-1-(Pyridin-3-ylsulfamoyl)-pyrrolidine-2-carboxylic acid (3-phenyl-propyl)-amide (compound 118)

Step 1: Synthesis of (S)-1-(Pyridin-3-ylsulfamoyl)-pyrrolidine-2-carboxylic acid (Compound 116):

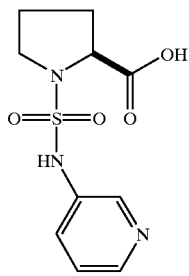

Compound 116 was prepared analogous to Example 67—Step 2.

Step 2: Synthesis of (S)-1-(Pyridin-3-ylsulfamoyl)-pyrrolidine-2-carboxylic acid (3-phenyl-propyl)-amide (Compound 118):

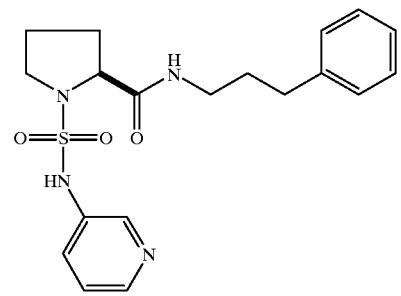

Compound 118 was prepared from the carboxylic acid (compound 116) and 3-phenyl-propylamine by a synthetic method analogous to the step 2 of compound 31 synthesis. A 21% yield was obtained for the title compound.

Spectral analysis of the product was consistent with compound 118: $^1$H NMR ($CDCl_3$): δ8.56 (1H, d, J=2.1 Hz), 8.35 (1H, br d), 7.76 (1H, m), 7.3–7.1 (6H, m), 6.47 (1H, t, J=6 Hz), 4.30 (1H, t, J=6.3 Hz), 3.47–3.37 (1H, m), 3.20 (2H, m), 2.59 (2H, t, J=8.1 Hz), 2.16–2.06 (1H, m), 1.87–1.68 (5H, m). HRMS (MALDI) calculated for $C_{19}H_{25}N_4O_3S$ (M+H$^+$) 389.1647; found 389.1638.

The thiomorpholine derivatives of the present invention may be prepared in the manner depicted in Scheme 9 below:

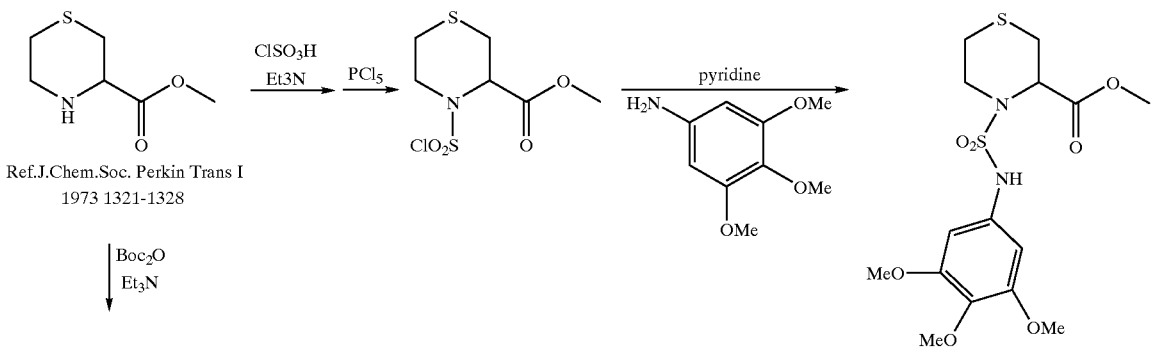

Scheme 9

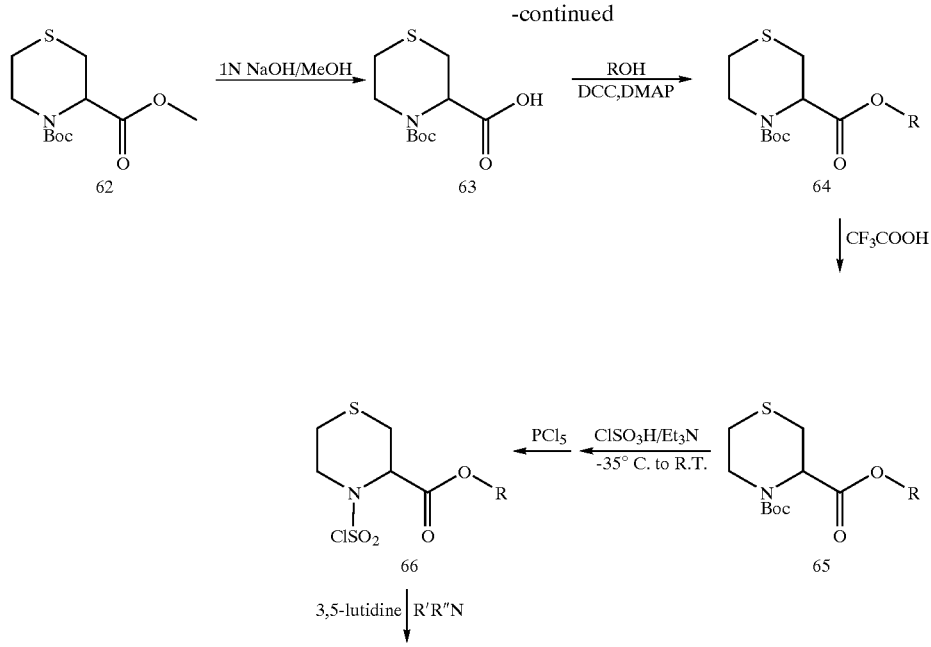

wherein R is

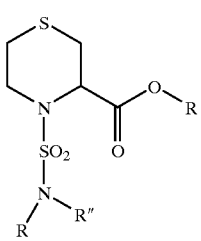

R" is hydrogen, 3,4,5-trimethoxyphenyl, Ph and

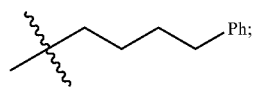

and

R' is hydrogen.

The following compounds were prepared according to Scheme 9 depicted above:

Example 70

Synthesis of 4-(3,4,5-Trimethoxy-phenylsulfamoyl)-thiomorpholine-3-carboxylic acid methyl ester (Compound 61)

Step 1: Synthesis of 4-Chlorosulfonyl-thiomorpholine-3-carboxylic acid methyl ester (Compound 60):

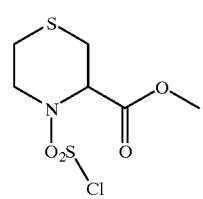

Compound 60 was prepared from methyl thiomorpholine-3-carboxylate with 83% yield by a synthetic method analogous to Example 3—Step 5.

Spectral analysis was consistent with compound 60: $^1$H NMR (CDCl$_3$): δ5.12 (1H, br s), 4.28 (1H, br d, J=14.1 Hz), 3.85 (3H, s), 3.83 (1H, m), 3.25–2.95 (3H, m), 2.50 (1H, d, J=13.5 Hz).

Step 2: Synthesis of 4-(3,4,5-Trimethoxy-phenylsulfamoyl)-thiomorpholine-3-carboxylic acid methyl ester (compound 61):

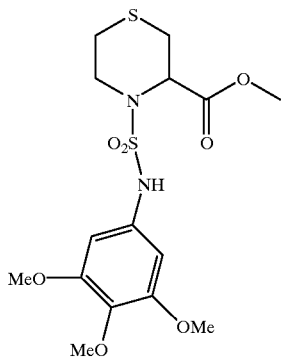

Compound 61 was prepared from compound 60 (83% yield) by a synthetic method analogous to Example 3—Step 6.

Spectral analysis was consistent with compound 61: $^1$H NMR (CDCl$_3$): δ7.17 (1H, br s), 6.52 (2H, s), 5.04 (1H, br t), 3.95 (1H, dt, J=13, 3 Hz), 3.85 (6H, s), 3.82 (3H, s), 3.37 (1H, td, J=12.7, 2.6 Hz), 3.12 (1H, dt, J=13.6, 2.8 Hz), 3.00 (1H, dd, J=13.8, 3.8 Hz), 2.82 (1H, td, J=13.5, 3 Hz), 2.46 (1H, dd, J=13.2, 2.9 Hz). MS (LCMS) 407 (M+H$^+$).

Example 71

Synthesis of 4-sulfamoyl-thiomorpholine-3-carboxylic acid 4-phenyl-butyl ester (Compound 67) and 4-(3,4,5-trimethoxy-phenylsulfamoyl)-thiomorpholine-3-carboxylic acid 4-phenyl-butyl ester (Compound 68)

Step 1: Synthesis of Thiomorpholine-3,4-dicarboxylic acid 4-tert-butyl ester 3-methyl ester (compound 62):

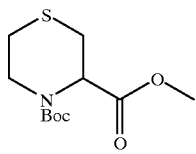

At 0° C., triethylamine (8 mL) and tert-butylcarboxylic anhydride (6.7 g, 30.7 mmol) were added to a 1,4-dioxane solution (35 mL) of methyl thiomorpholine-3-carboxylate (3.8 g, 23.6 mmol) which was prepared by the method reported by Gardon Lowe (*J. Chemn. Soc. Perkin Trans I* 1973 1321–1328). The mixture was allowed to warm to 25° C. After 20 hours, the solution was diluted with EtOAc (100 mL), washed with saturated NaHCO$_3$ solution (1×60 mL) and brine (1×60 mL), dried over MgSO$_4$ and concentrated in vacuo. The residue was filtered through a pad of silica gel (100 mL) using 5% EtOAc in hexanes as the eluent. Evaporation afforded 6 g (97% yield) of compound 62 as a pale-yellow oil.

Spectral analysis of the product was consistent with compound 62: $^1$H NMR (CDCl$_3$): (two rotamers) δ5.27 and 5.02 (1H, s), 5.36 and (4.24 (1H, d, J=11 Hz), 3.79 (3H, s), 3.35–2.35 (5H, m).

Step 2: Synthesis of Thiomorpholine-3,4-dicarboxylic acid 4-tert-butyl ester (compound 63):

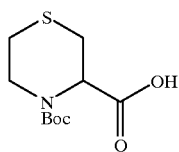

At 25° C., an aqueous NaOH solution (1N, 15 mL) was added to the methyl ester solution in MeOH (30 mL). After 4 hours, the mixture was concentrated in vacuo and adjusted to pH~2 using ice-cold 10% HCl solution. The residue was extracted with Et$_2$O (3×30 mL). Combined organic layers were dried over Na$_2$SO$_4$ and concentrated. The crude oil was purified by passing through a pad of silica gel (60 mL) using 20% EtOAc in hexanes. After evaporation, the gummy solid was triturated with 50 mL of warm hexanes, affording 5 g (96% yield) of white solid.

Spectral analysis of the product was consistent with compound 63: $^1$H NMR (CDCl$_3$): (two rotamers) δ5.32 and 5.10 (1H, s), 4.37 and 4.24 (1H, d, J=12 Hz), 3.4–2.3 (5H, m), 1.42 (9H, s).

Step 3: Synthesis of Thiomorpholine-3,4-dicarboxylic acid 4-tert-butyl ester 3-(4-phenyl-butyl) ester (compound 64):

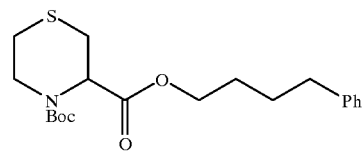

Compound 64 was prepared from compound 63 (70% yield) by a synthetic method analogous to Example 3—Step 3.

Spectral analysis of the product was consistent with compound 64: $^1$H NMR (CDCl$_3$): (two rotamers) δ7.4–7.1 (5H, m), 4.3–4.1 (3H, m), 3.78 (1H, m), 3.39 (1H, m), 3.2–3.0 (3H, m), 2.78 (1H, d, J=13 Hz), 2.60 (2H, m), 1.62 (9H, s).

Step 4: Synthesis of Thiomorpholine-3-carboxylic acid 4-phenyl-butyl ester (compound 65):

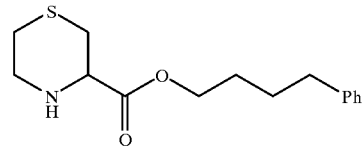

Compound 65 was prepared from compound 64 (80% yield) by a synthetic method analogous to Example 3—Step 4.

Spectral analysis of the product was consistent with compound 65: $^1$H NMR (CDCl$_3$): δ7.35–7.1 (5H, m), 4.25–4.1 (3H, m), 3.63 (1H, dd, J=13, 3 Hz), 3.38 (1H, dt, J=13, 3.2 Hz), 3.01 (1H, dt, J=12.3, 2 Hz), 2.9–2.6 (4H, m), 1.70 (4H, m).

Step 5: Synthesis of 4-chlorosulfonyl-thiomorpholine-3-carboxylic acid 4-phenyl-butyl ester (compound 66):

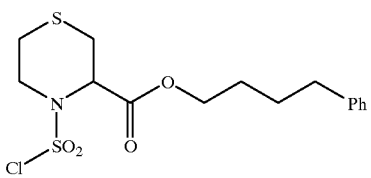

Compound 66 was prepared from compound 65 (50% yield) by a synthetic method analogous to Example 3—Step 5.

Spectral analysis of the product was consistent with compound 66: $^1$H NMR (CDCl$_3$): δ7.35–7.1 (5H, m), 5.11 (1H, m), 4.27 (3H, m), 3.82 (1H, dt, J=13, 3Hz), 3.2–3.0 (3H, m), 2.67 (2H, m), 2.49 (1H, d, J=13 Hz), 1.8–1.65 (4H, m).

Step 6: Synthesis of 4-sulfamoyl-thiomorpholine-3-carboxylic acid 4-phenyl-butyl ester (compound 67) and 4-(3,4,5-trimethoxy-phenylsulfamoyl)-thiomorpholine-3-carboxylic acid 4-phenyl-butyl ester (compound 68):

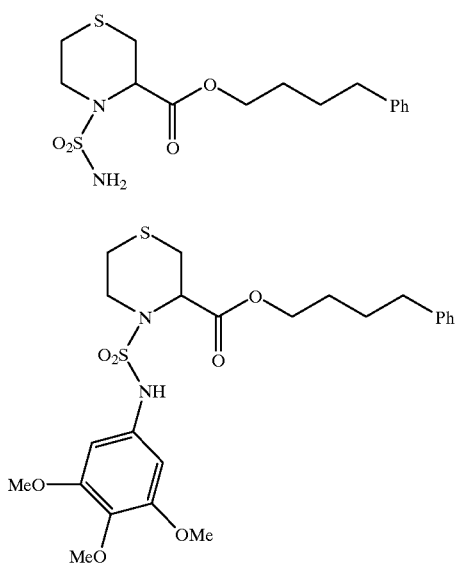

Compound 67 and compound 68 were prepared from compound 66 by a synthetic method analogous to Example 3—Step 6. Compound 67 was obtained in 35% yield. Compound 68 was also isolated from the reaction in 10% yield.

Spectral analysis of the product was consistent with compound 67: $^1$H NMR (CDCl$_3$): δ7.35–7.2 (5H, m), 5.07 (2H, br s), 4.98 (1H, m), 4.35–4.1 (2H, m), 3.90 (1H, dt, J=13.0, 3 Hz), 3.28 (1H, td, J=13, 3 Hz), 3.15–2.97 (2H, m), 2.88 (1H, td, J=13.2, 3.3 Hz), 2.65 (2H, m), 2.52 (1H, d, J=13 Hz), 1.8–1.6 (4H, m).

Spectral analysis of the product was consistent with compound 68: $^1$H NMR (CDCl$_3$): δ7.35–7.1 (5H, m), 6.50 (2H, s), 5.02 (1H, m), 4.35–4.15 (2H, m), 3.94 (1H, dt, J=13.2, 3.2 Hz), 3.84 (6H, s), 3.80 (3H, s), 3.36 (1H, td, J=12.8, 2,8 Hz), 3.10 (1H, dt, J=13.8, 2.8 Hz), 2.99 (1H, dd, J=13.8, 3.9 Hz), 2.80 (1H, td, J=13.6, 3.0 Hz), 2.66 (2H, m), 2.44 (1H, dd, J=13.2, 3 Hz), 1.69 (4H, m). MS (MALDI): 524 (M$^+$), 547 (M+Na$^+$). HRMS: calculated for C$_{24}$H$_{32}$N$_2$O$_7$S$_2$ (M$^+$) 524.1651; found 524.1650.

Example 72

Synthesis of 4-Phenylsulfamoyl-thiomorpholine-3-carboxylic acid 4-phenyl-butyl ester (Compound 69)

Step 1: Synthesis of 4-chlorosulfonyl-thiomorpholine-3-carboxylic acid 4-phenyl-butyl ester (compound 66):

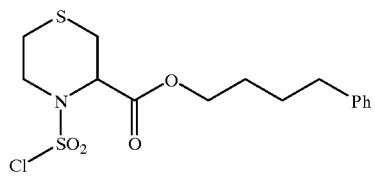

Compound 66 was prepared analogous to Example 71—Step 5.

Step 2: Synthesis of 4-Phenylsulfamoyl-thiomorpholine-3-carboxylic acid 4-phenyl-butyl ester (compound 69):

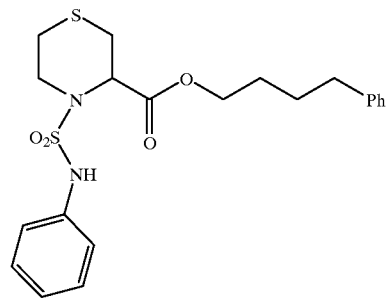

Compound 69 was prepared from compound 66 by a synthetic method analogous to the method II of compound 25 synthesis. An 18% yield was obtained.

Spectral analysis of the product was consistent with compound 69: $^1$H NMR (CDCl$_3$): δ7.3–6.95 (10H, m), 4.95 (1H, t, J=3.6 Hz), 4.19 (2H, m), 3.84 (1H, dt, J=13.2, 3 Hz), 3.29 (1H, td, J=12.6, 2.4 Hz), 3.01 (1H, dt, J=14.1, 2.7 Hz), 2.87 (1H, dd, J=14.1, 3.6 Hz). HRMS (MALDI): calculated for C$_{21}$H$_{26}$N$_2$O$_4$S$_2$Na (M+Na$^+$) 457.1226; found 457.1245.

Example 73

Synthesis of 4-(2-Oxo-2,3-dihydro-1H-benzoimidazol-5-ylsulfamoyl)-thiomorpholine-3-carboxylic acid 4-phenyl-butyl ester (Compound 70)

Step 1: Synthesis of 4-chlorosulfonyl-thiomorpholine-3-carboxylic acid 4-phenyl-butyl ester (compound 66):

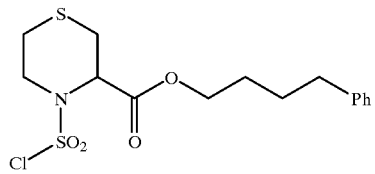

Compound 66 was prepared analogous to Example 71—Step 5.

Step 2: Synthesis of 4-(2-Oxo-2,3-dihydo-1H-benzoimidazol-5-ylsulfamoyl)-thiomorpholine-3-carboxylic acid 4-phenyl-butyl ester (compound 70):

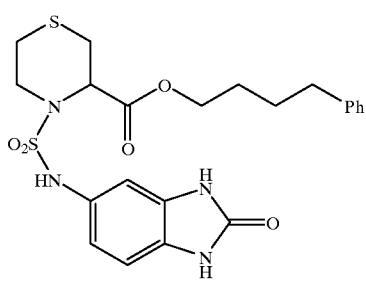

Compound 70 was prepared from compound 66 by a synthetic method analogous to the method II of compound 25 synthesis. A 34% yield was obtained.

Spectral analysis of the product was consistent with compound 70: $^1$H NMR (CD$_3$OD): δ7.2–7.0 (5H, m), 6.93–6.86 (2H, m), 6.78 (1H, dd, J=8.7, 2.1 Hz), 4.06 (2H, m), 3.77 (1H, J=14.1, 3 Hz), 3.33 (1H, m), 2.81 (1H, br dt), 2.6–2.45 (3H, m), 2.35 (1H, td, J=12.3, 3.6 Hz), 2.23 (1H, m). HRMS (MALDI): calculated for $C_{22}H_{27}N_4O_5S_2$ (M+H$^+$) 491.1417; found 491.1402.

The heterocyclic series of the present invention may be prepared in the manner depicted in Scheme 10 below:

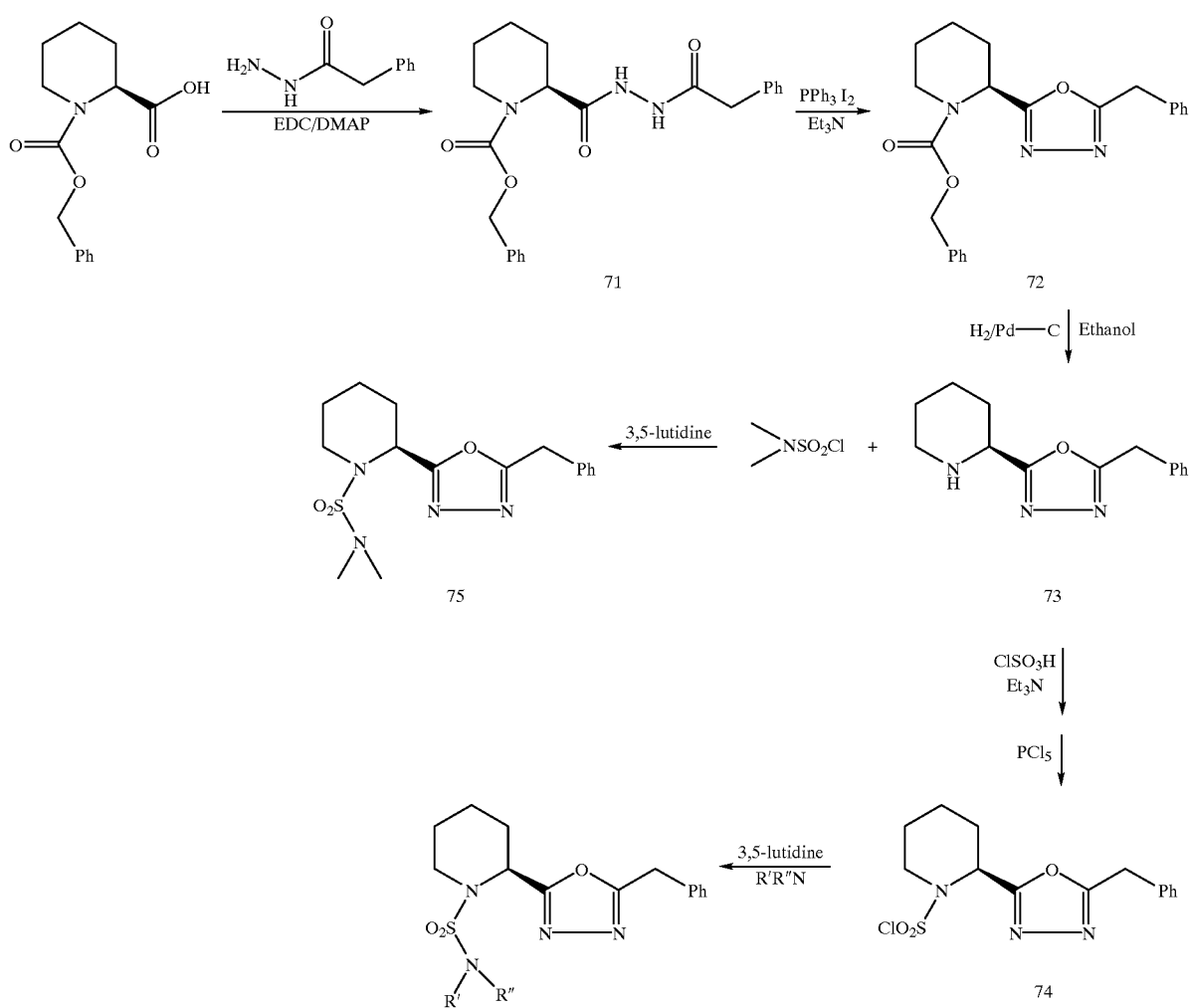

wherein R' is hydrogen and methyl; and

R" is 4-methoxyphenyl, phenyl and 3,4,5-trimethoxyphenyl.

The following compounds were prepared according to Scheme 7 depicted above:

Example 74

Synthesis of 2S-(5-Benzyl-[1,3,4]oxadiazol-2-yl)-piperidine-1-sulfonic acid dimethylamide (Compound 75)

Step 1: Synthesis of (S)-2-[N'-(2-Phenyl-ethanoyl)-hydrazinocarbonyl]-piperidine-1-carboxylic acid benzyl ester (compound 71):

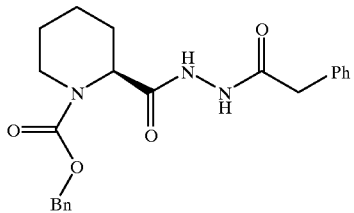

To a $CH_2Cl_2$ solution (50 mL) of (S)-(1)-1-(carbobenzyloxy)-2-piperidincarboxylic acid (1.75 g, 6.66 mmol) and phenyl acetic hydrazide (1 g, 6.66 mmol) were added EDC (1.91 g, 9.99 mmol) and DMAP (0.5 g, 4 mmol). After 20 hours, the mixture was diluted with $CH_2Cl_2$ (100 mL), washed with ice-cold 5% HCl solution (50 mL), over $Na_2SO_4$ and concentrated. 3 g of solid was obtained.

Spectral analysis of the product was consistent with compound 71: $^1H$ NMR ($CDCl_3$): δ8.37 (1H, br s), 7.88 (1H, d, J=4.8 Hz), 7.4–7.2 (10H, m), 5.15 (2H, AB), 4.88 (1H, br s), 4.1 (1H, m), 3.63 (2H, br s), 2.23 (1H, m).

Step 2: Synthesis of (S)-2-(5-Benzyl-[1,3,4]-oxadiazol-2-yl)-piperidine-1-carboxylic acid benzyl ester (compound 72):

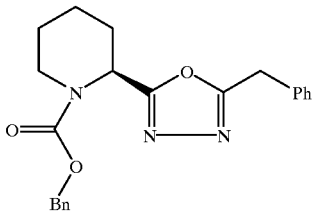

At 25° C., iodine (3.21, 12.64 mmol) was added to the $PPh_3$ solution in $CH_2Cl_2$ (40 mL). After 10 minutes, triethylamine (1.5 mL) was added, followed by compound 71 (2.5 g, 6.32 mmol). After 20 hours, the solution was concentrated and passed through a pad of silica gel (100 mL). The crude oil was purified by column chromatography (25–30% EtOAc in hexanes), affording 600 mg (25%) of the desired product as a solid. 1.6 g of compound 71 was recovered.

Spectral analysis of the product was consistent with compound 72: $^1H$ NMR ($CDCl_3$): δ7.4–7.2 (10H, m), 5.58 (1H, br s), 5.13 (2H, br s), 4.12 (2H, br s), 4.10 (1H, m), 2.92 (1H, br s), 2.23 (1H, d, J=13.5 Hz).

Step 3: Synthesis of (S)-2-(5-benzyl-[1,3,4]oxadiazol-2-yl)-piperidine (compound 73):

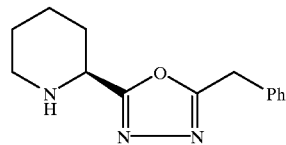

To an ethanol solution (10 mL) of compound 72 was added 10% Pd on carbon (10 mg) and kept under hydrogen atmosphere (1 atm) for 30 hours. The catalyst was filtered off. After removal of solvent in vacuo, a white solid was obtained (75 mg).

Spectral analysis of the product was consistent with compound 73: $^1H$ NMR ($CDCl_3$): δ7.4–7.2 (5H, m), 4.17 (2H, br s), 4.12 (2H, br s), 4.06 (1H, dd, J=9.9, 3.6 Hz), 3.16 (1H, dt, J=11.7, 5 Hz), 2.79(1H, m).

Step 4: Synthesis of 2S-(5-Benzyl-[1,3,4]oxadiazol-2-yl)-piperidine-1-sulfonic acid dimethylamide (compound 75):

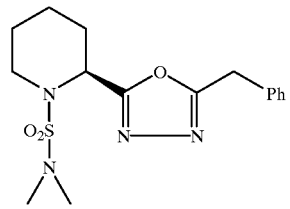

Compound 75 was prepared from compound 73 and N,N-dimethylsulfamoyl chloride by a synthetic method analogous to the method II of compound 25 synthesis. A 45% yield was obtained.

Spectral analysis of the product was consistent with compound 75: $^1H$ NMR ($CDCl_3$): δ7.4–7.2 (5H, m), 5.19 (1H, d, J=4.9 Hz), 4.20 (2H, AB), 3.67 (1H, br d), 3.15 (1H, m), 2.68 (6H, s), 2.17 (1H, br d), 1.99 (1H, m). HRMS (MALDI): calculated for $C_{16}H_{23}N_4O_3S$ (M+H$^+$) 351.1485; found 351.1499.

Example 75

Synthesis of 2-(5-Benzyl-[1,3,4]oxadiazol-2-yl)-piperidine-1-sulfonic acid (3,4,5-trimethoxy-phenyl)-amide (Compound 78)

Step 1: Synthesis of (S)-2-(5-benzyl-[1,3,4]pxadiazol-2-yl)-piperidine-1-sulfonyl chloride (compound 74):

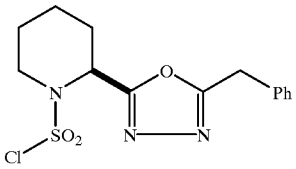

Compound 74 was prepared from compound 73 by a synthetic method analogous to that of Example 3—Step 5. A 65% yield was obtained.

Spectral analysis was consistent with compound 74: $^1H$ NMR ($CDCl_3$): 67.4–7.2 (5H, m), 5.22 (1H, br t, J=4.5 Hz), 4.22 (2H, br s), 3.91 (1H, br d), 3.39 (1H, m), 2.15 (2H, m).

Step 2: Synthesis of 2-(5-Benzyl-[1,3,4]oxadiazol-2-yl)-piperidine-1-sulfonic acid (3,4,5-trimethoxy-phenyl)-amide (compound 78):

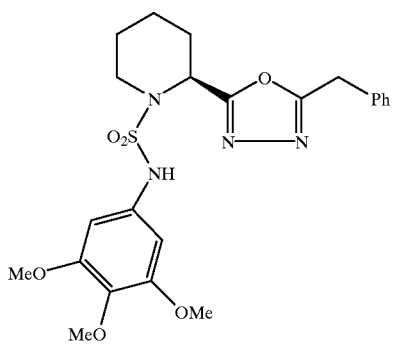

Compound 78 was prepared from compound 74 by a synthetic method analogous to the method II of compound 25 synthesis. An 87% yield was obtained.

Spectral analysis of the product was consistent with compound 78: $^1$H NMR (CDCl$_3$): δ7.93 (1H, s), 7.4–7.2 (5H, m), 6.52 (2H, s), 5.39 (1H, m), 4.18 (2H, AB), 3.83 (6H, s), 3.80 (3H, s), 3.74 (1H, br d), 3.14 (1H, td, J=13.4, 3.2 Hz), 2.21 (1H, d, br d), 1.95 (1H, m). HRMS (MALDI): calculated for C$_{23}$H$_{28}$N$_4$O$_6$SNa (M+Na$^+$) 511.1622; found 511.1622.

Example 76

Synthesis of 2S-(5-Benzyl- [1,3,4]oxadiazol-2-yl)-piperidine-1-sulfonic acid phenylamide (Compound 76)

Step 1: Synthesis of (S)-2-(5-benzyl-[1,3,4]pxadiazol-2-yl)-piperidine-1-sulfonyl chloride (compound 74):

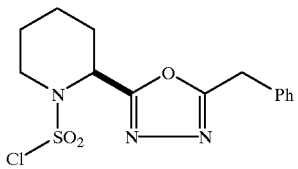

Compound 74 was prepared analogous to Example 75—Step 1.

Step 2: Synthesis of 2S-(5-Benzyl-[1,3,4]oxadiazol-2-yl)-piperidine-1-sulfonic acid phenylamide (compound 76):

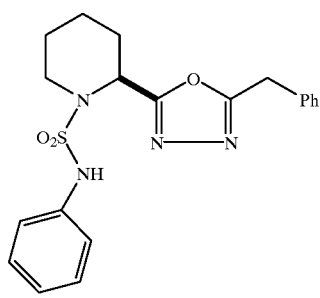

Compound 76 was prepared from compound 74 by a synthetic method analogous to the method II of compound 25 synthesis. A 92% yield was obtained.

Spectral analysis of the product was consistent with compound 76: $^1$H NMR (CDCl$_3$): δ7.94 (1H, s), 7.4–7.2 (9H, m), 7.09 (1H, m), 5.38 (1H, br d), 4.18 (2H, AB), 3.69 (1H, br d, J=12.6 Hz), 3.10 (1H, td, J=12.3, 3.3 Hz), 2.23 (1H, br d), 1.93 (1H, m). HRMS (MALDI): calculated for C$_{20}$H$_{22}$N$_4$O$_3$SNa (M+Na$^+$) 421.1305; found 5 421.1318.

Example 77

Synthesis of 2-(5-Benzyl-[1,3,4]oxadiazol-2-yl)-piperidine-1-sulfonic acid (4-methoxy-phenyl)-methyl-amide (Compound 77)

Step 1: Synthesis of (S)-2-(5-benzyl-[1,3,4]pxadiazol-2-yl)-piperidine-1-sulfonyl chloride (compound 74)

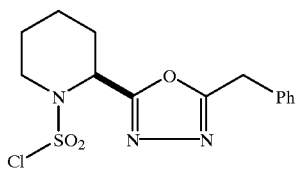

Compound 74 was prepared analogous to Example 75—Step 1.

Step 2: Synthesis of 2-(5-Benzyl-[1,3,4]oxadiazol-2-yl)-piperidine-1-sulfonic acid (4-methoxy-phenyl)-methyl-amide (compound 77):

Compound 77 was prepared from compound 74 by a synthetic method analogous to the method II of compound 25 synthesis. An 88% yield was obtained.

Spectral analysis of the product was consistent with compound 77: $^1$H NMR (CDCl$_3$): δ7.4–7.15 (7H, m), 6.80 (2H, m), 5.18 (1H, d, J=4.8 Hz), 4.19 (2H, br s), 3.78 (3H, s), 3.61 (1H, br d), 3.16 (1H, m), 3.09 (3H, s), 2.08 (1H, br d), 1.85 (1H, m). HRMS (MALDI): calculated for C$_{22}$H$_{26}$N$_4$O$_4$SNa (M+Na$^+$) 465.1567; found 465.1559.

The bicyclic derivatives of the present invention may be prepared in the manner depicted in Scheme 11 below:

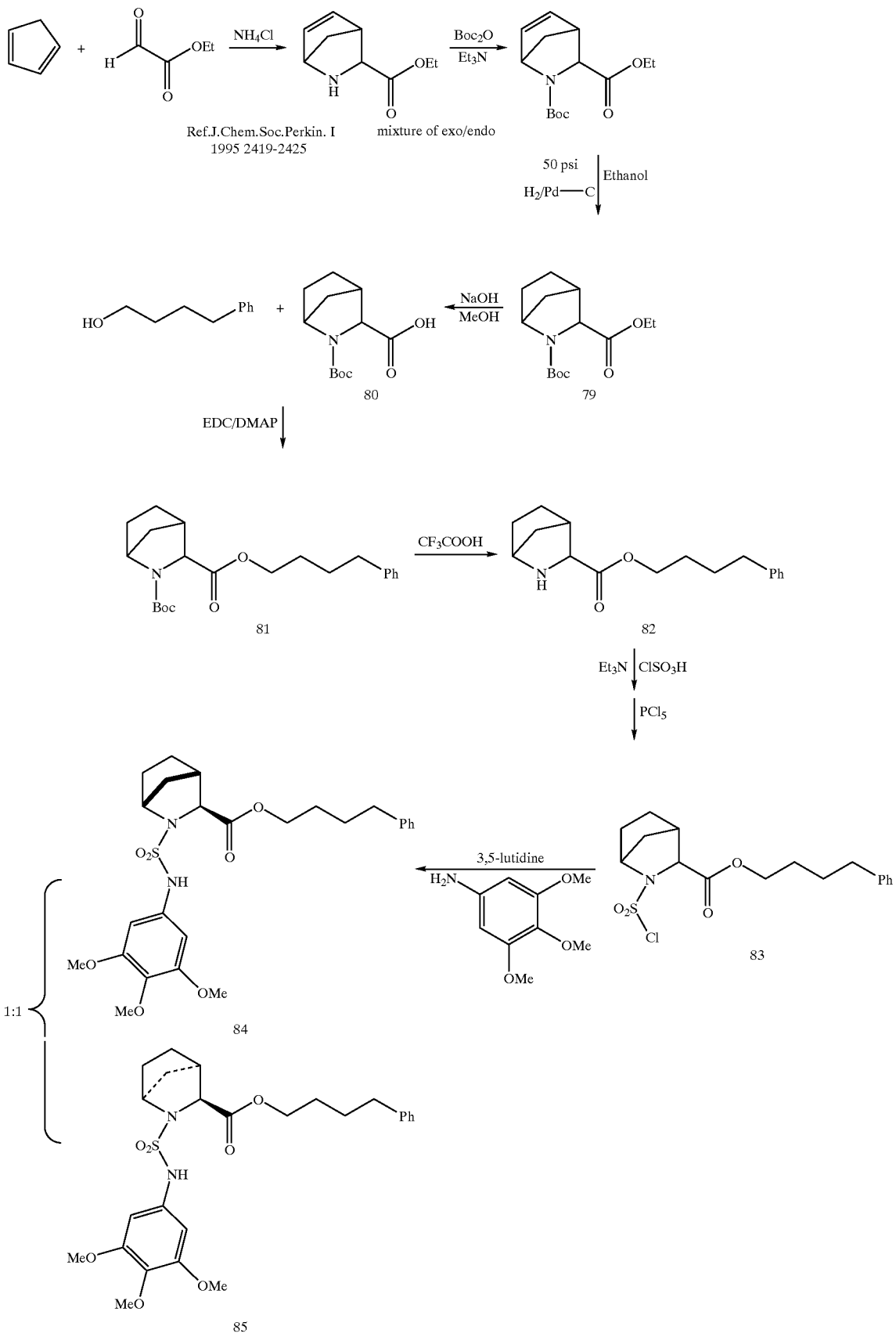
Scheme 11

The following compounds were prepared according to Scheme 11 depicted above:

Example 78

Synthesis of 2-(3,4,5-Trimethoxy-phenylsulfamoyl)-2-aza-bicyclo[2.2.1]heptane-exo-3-carboxylic acid 4-phenyl-butyl ester (Compound 84) and 2-(3,4,5-Trimethoxy-phenylsulfamoyl)-2-aza-bicyclo[2.2.1]heptane-endo-3-carboxylic acid 4-phenyl-butyl ester (Compound 85)

Step 1: Synthesis of 2-aza-bicyclo[2.2.1]heptane-2,3-dicarboxylic acid 2-tert-butyl ester 3-ether ester (compound 79):

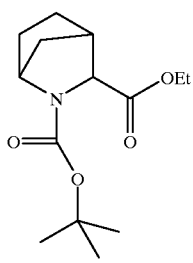

Following Hursthouse's procedure (*J. Chem. Soc. Perkin Tran. I*, 1995, 2419–2425), 1-aza-bicyclo[2.2.1]hept-5-ene-3-carboxylic acid ester was prepared as an exo- and endo-mixture. At 0° C., triethylamine (15 mL) and tert-butylcarboxylic anhydride (19 g, 87.5 mmol) were added to a 1,4-dioxane solution (50 mL) of the above exo/endo mixture (13.2 g, 72.9 mmol). The mixture was allowed to warm to 25° C. After 20 hours, the solution was diluted with EtOAc (100 1L), washed with saturated NaHCO$_3$ solution (1×60 mL) and brine (1×60 mL), dried over MgSO$_4$ and concentrated in vacuo. The residue was filtered through a pad of silica gel (100 mL) using 5% EtOAc in hexanes as the eluent. Evaporation afforded 20 g of pale-yellow oil, a portion of which (4.5 g) was dissolved in 50 mL of ethanol. Pd on carbon (0.5 g) was added to the solution, and the suspension was kept under hydrogen atmosphere (50 psi) for 20 hours. The catalyst was filtered off. After removal of the solvent, 4.3 g of colorless oil was obtained.

Spectral analysis of the product was consistent with compound 79: $^1$H NMR (CDCl$_3$): (two rotamers of endo/exo mixture) δ4.45–4.1 and 3.85–3.66 (4H, m), 2.77 and 2.66 (1H, br s).

Step 2: Synthesis of 2-aza-bicyclo[2.2.1]heptane-2,3-dicarboxylic acid 2-tert-butyl ester (compound 80):

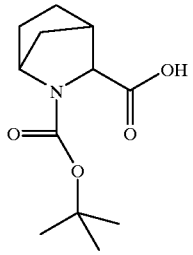

Compound 80 was prepared from compound 79 by a synthetic method analogous to that of Example 3—Step 2. A 45% yield was obtained Step 3: Synthesis of 2-aza-bicyclo[2.2.1]heptane-2,3-dicarboxylic acid 2-tert-butyl ester 3-(4-phenyl-butyl) ester (compound 81):

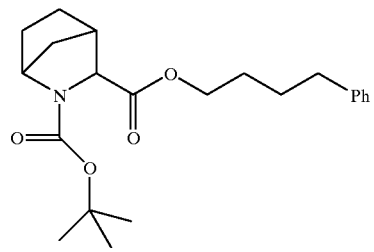

Compound 81 was prepared from compound 80 by a synthetic method analogous to that of Example 3—Step 3. A 72% yield was obtained.

Spectral analysis of the product was consistent with compound 81: $^1$H NMR (CDCl$_3$): (two rotamers of endo/exo mixture) δ7.35–7.1 (5H, m), 4.45–4.05 and 3.82–3.71 (5H, m), 2.77 and 2.64 (3H, br s).

Step 4: Synthesis Preparation of 2-aza-bicyclo[2.2.1]heptane-3-carboxylic acid 4-phenyl-butyl ester (compound 82):

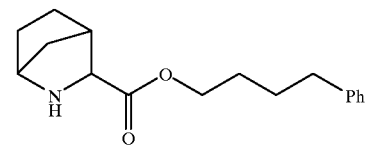

Compound 82 was prepared from compound 81 by a synthetic method analogous to that of Example 3—Step 4. An 80% yield was obtained.

Spectral analysis of the product was consistent with compound 82: $^1$H NMR (CDCl$_3$): (endo/exo mixture) δ7.35–7.1 (5H, m), 4.25–4.05 (2H, m), 3.82 and 3.52 (1H, m), 3.48 and 3.30 (1H, br s), 2.69–2.57 (3H, m).

Step 5: Synthesis of 2-chlorosulfonyl-2-aza-bicyclo[2.2.1]heptane-3-carboxylic acid 4-phenyl-butyl ester (compound 83):

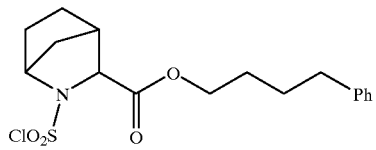

Compound 83 was prepared from compound 82 by a synthetic method analogous to that of Example 3—Step 5. A 70% yield was obtained.

Spectral analysis of the product was consistent with compound 83: $^1$H NMR (CDCl$_3$): (endo/exo mixture) δ7.35–7.1 (5H, m), 4.54 and 4.47 (1H, br s), 4.3–4.1 (3H, m), 2.97 and 3.90 (1H, br s), 2.82 and 2,53 (1H, m), 2.65 (2H, m), 2.15 (2H, m).

Step 6: Synthesis of 2-(3,4,5-Trimethoxy-phenylsulfamoyl)-2-aza-bicyclo[2.2.1]heptane-exo-3-carboxylic acid 4-phenyl-butyl ester (compound 84) and 2-(3,4,5-Trimethoxy-phenylsulfamoyl)-2-aza-bicyclo[2.2.1]heptane-endo-3-carboxylic acid 4-phenyl-butyl ester (compound 85):

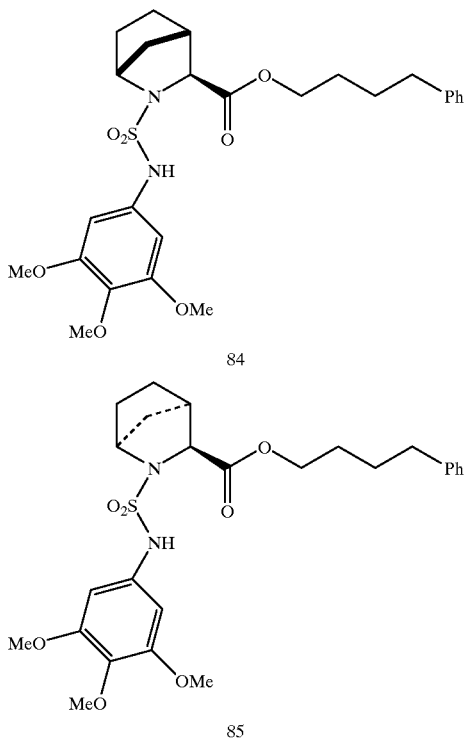

Compound 84 and compound 85 were prepared from compound 83 (~1:1 exo/endo mixture) by a synthetic method analogous to the method II of compound 25 synthesis. Compound 84 was obtained in 40% yield as the first fraction, while compound 85 was isolated in 35% yield as the second fraction.

Spectral analysis of the product was consistent with compound 84: $^1$H NMR (CDCl$_3$): δ7.35–7.1 (5H, m), 6.76 (1H, s), 6.59 (2H, s), 4.15 (2H, m), 4.02 (1H, s), 3.98 (1H, br s), 3.84 (6H, s), 3.82 (3H, s), 2.76 (1H, br d), 2.64 (2H, m), 2.04 (1H, m). HRMS (MALDI): calculated for C$_{26}$H$_{34}$N$_2$O$_7$SNa (M+Na$^+$) 541.1979; found 541.1996.

Spectral analysis of the product was consistent with compound 85: $^1$H NMR (CDCl$_3$): δ7.35–7.1 (5H, m), 6.77 (1H, br s), 6.60 (2H, s), 4.45 (1H, d, J=4.8 Hz), 4.2–4.15 (3H, m), 3.85 (6H, s), 3.81 (3H, s), 2.88 (1H, br d), 2.65 (2H, m). HRMS (MALDI): calculated for C$_{26}$H$_{34}$N$_2$O$_7$S (M$^+$) 518.2081; found 518.2092.

A variety of assays and techniques may be employed to determine the activities of the compounds of the present invention. The activity of a compound of the invention for stimulation of neurite outgrowth through the FKBP pathway is directly related to its binding affinity for FKBP12 and its ability to inhibit FKBP12 rotamase activity. In order to quantify these latter properties, assays known in the art for measuring ligand binding and enzyme activity may be employed. Assays for stimulation of neurite outgrowth are described below.

For example, compounds may be tested to determine their neurotrophic activity using the method described by Lyons et al., *Proc. Natl. Acad. Sci.*, 91:3191–3195 (1994). In this rat pheochromocytoma assay for neurite outgrowth, PC12 rat pheochromocytoma cells are maintained at 37° C. and 5% CO$_2$ in Dulbecco's modified Eagle's medium (DMEM) supplemented with 10% heat-inactivated horse serum and 5% heat-inactivated fetal bovine serum. Cells are then plated, coated at 10$^5$ per 35 mm culture well with rat tail collagen at 5 mg/cm$^2$, and allowed to attach. Medium is then replaced with DMEM supplemented with 2% horse serum, 1% fetal bovine serum, nerve growth factor (NGF), and/or varying concentrations of test compounds. The control cultures are administered NGF without any of the test compounds.

Another exemplary method that may be used for measuring potency for stimulation of neurite outgrowth is the rat dorsal root ganglia assay. In this assay, dorsal root ganglia are dissected from 16-day-old Sprague-Dawley rat embryos. The sensory ganglia are then cultured in collagen-coated 35 mm Falcon dishes with N-2 medium (DMEMIHam's F$_{12}$, 1:1) at 37° C. in a 15% CO$_2$ environment. The medium is supplemented with selenium, progesterone, insulin, putrescine, glucose, penicillin and streptomycin. The ganglia are then treated with various concentrations of NGF (0–100 ng/ml) and test compound. The sensory ganglia are observed every two to three days under a phase contrast microscope, and the axon lengths are measured. See Lyons et al., *PNAS*, 91:3191–3195 (1994).

Other suitable assays may be used to measure the activity of the compounds of the present invention. For example, immunosuppressant activity can be estimated through measurements of the inhibition of calcineurin phosphatase activity by complexes of compounds of the invention bound to FKBP (Babine et al., *Bioorg. Med. Chem. Lett.*, 6, 385–390, 1996). The phosphopeptide phosphatase activity of calcineurin is assayed at 30° C. using a continuous coupled spectrophotometric assay (Etzkorn et al., *Biochemistry*, 32, 2380, 1994) and the phosphorylated 19-mer peptide substrate derived from the regulatory subunit (R$_{II}$) of cAMP-dependent protein kinase. The assay mixture contains 50 mM MOPS (pH 7.5), 0.1 M NaCl, 6 mM MgCl$_2$, 0.5 mg/ml bovine serum albumin, 0.5 mM dithiothreitol, 1 mM CaCl$_2$, 1 mM MnCl$_2$, 20 µM phosphorylated R$_{II}$ peptide, 20 nM human recombinant calcineurin, 40 nM calmodulin, 10 µg/mL purine ribonucleoside phosphorylase, and 200 µM 15 methylthioguanosine as described by Etzkorn et al., plus 1% dimethylsulfoxide (DMSO) as co-solvent and 100 µM FKBP. Compounds are tested for FKBP-dependent inhibition of calcineurin at their maximum solubility. Under these conditions, the apparent inhibition constant for inhibition of human recombinant calcineurin by FKBP-FK506 is measured to be 43 nM.

Binding of compounds to FKBP may be measured directly using microcalorimetry. Calorimetric titrations are carried out using the MCS-ITC instrument (MicroCal Inc., Northhampton, Mass.). The titrations may be conducted as follows. Protein dialysate is degassed for 15 minutes using MicroCal equipment. Stock inhibitor solution is added to co-solvent (typically DMSO) and degassed dialysate, followed by brief sonication, to produce the final inhibitor solutions to be used in the titrations. Final inhibitor solutions are in the concentration range 10 to 80 µM. Dialyzed protein is added to co-solvent and degassed dialysate to produce FKBP12 solutions in the concentration range 200 to 1600 µM. As both solutions are prepared using degassed dialysate, no additional degassing of the solutions is performed. Co-solvent is added to the protein solutions to maintain a fixed co-solvent concentration throughout the course of the titration. Protein is titrated into inhibitor using a 125-µL injection syringe. The titrations are conducted with the ligand in the cell due to low solubility of inhibitors. Typically, a preliminary 2-µL injection is followed by fifteen 8-µL injections made at varying injection intervals. A full set of dilution controls is conducted for each titration. An appropriate volume of co-solvent is added to degassed dialysate to produce the buffered co-solvent solution used to obtain heats of dilution of the reactants. After correcting for the heats of dilution and deletion of the preliminary injection, the titration results are fitted using the "One Set of Sites Model" in the ORIGIN software package supplied with the instrument.

Binding to FKBP as directly measured by microcalorimetry has been found to correlate well with potency for inhibition of the rotamase reaction, which is readily assayed by methods known in the art (see, e.g., Fischer et al., *Biochim. Biophys. Acta* 791, 87 (1984); Fischer et al., *Biomed. Biochim. Acta* 43, 1101 (1984); Fischer et al., *Nature* 337, 476–478 (1989); Siekierka et al., *Nature,* 341, 755–57 (1989); U.S. Pat. No. 5,696,135; and Harding et al., *Nature,* 341, 758–60 (1989)).

In the rotamase inhibition assay, isomerization of an artificial substrate N-succinyl-Ala-Ala-Pro-Phe-p-nitroanilide is followed spectrophotometrically. The assay includes the cis form of the substrate, FKBP12, the compound being tested, and chymotrypsin. Chymotrypsin is able to cleave p-nitroaniline from the trans form of the substrate, but not from the cis form. Release of p-nitroaniline is measured spectrophotometrically. Using this assay, various amounts of the FKBP rotamase-inhibiting compounds of formula (I) were added to cis-N-succinyl-alanine-alanine-proline-phenylalanine-para-nitroaniline (BACHEM, 3132 Kashiwa Street, Torrance, Calif. 90505) in the presence of FKBP12 and chymotrypsin. Spectrophotometric measurements of p-nitroaniline concentrations allowed estimation of the apparent $K_i$ values, which are provided in Table 1 below.

TABLE 1

| Compound Number | Molecular Structure | Neurite-Outgrowth Activity (PC-12) | Microcalorimetry $K_d$ ($\mu$M) | Rotamase $K_{i(app)}$ ($\mu$M) |
| --- | --- | --- | --- | --- |
| 13 | 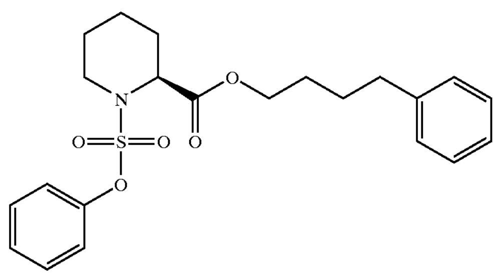 | NT | NT | NT |
| 15 | 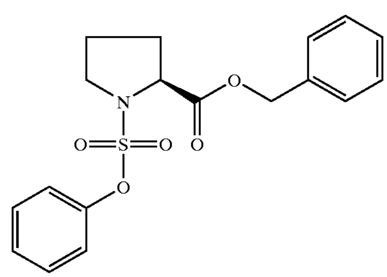 | NT | NT | NT |
| 22 | 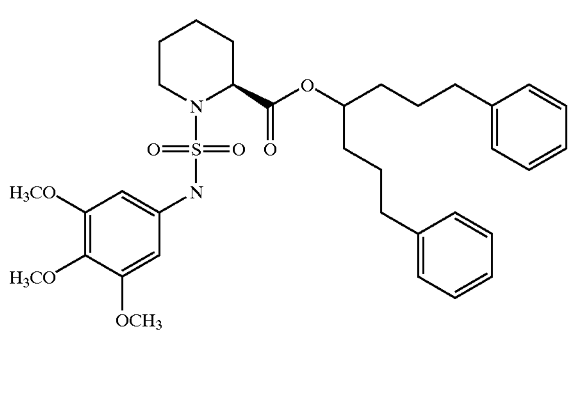 | NT | NT | 0.382 |

TABLE 1-continued

| Compound Number | Molecular Structure | Neurite-Outgrowth Activity (PC-12) | Microcalorimetry $K_d$ ($\mu$M) | Rotamase $K_{i(app)}$ ($\mu$M) |
| --- | --- | --- | --- | --- |
| 23 | 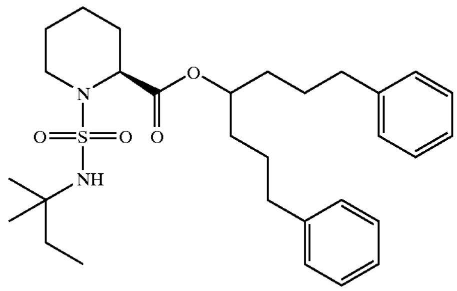 | NT | NT | 6.99 |
| 24 | 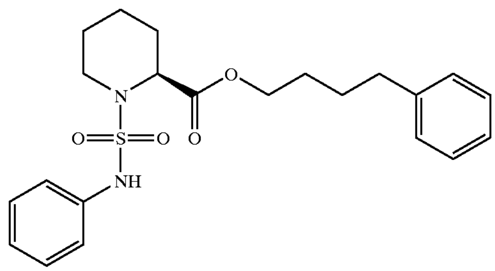 | NT | NT | 1.16 |
| 25 | 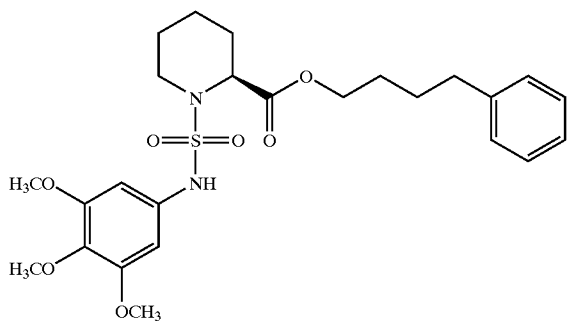 | 0.001–1 $\mu$M | 1.2 | 0.2 |
| 26 | 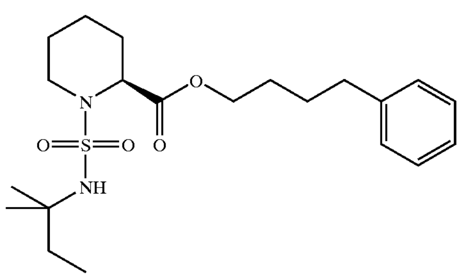 | NT | NT | 0.193 |
| 27 | 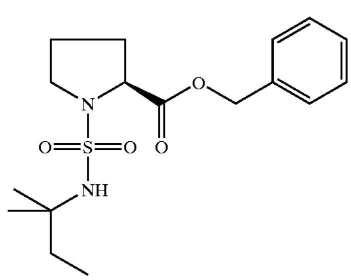 | NT | NT | NT |

TABLE 1-continued

| Compound Number | Molecular Structure | Neurite-Outgrowth Activity (PC-12) | Microcalorimetry $K_d$ ($\mu$M) | Rotamase $K_{i(app)}$ ($\mu$M) |
|---|---|---|---|---|
| 28 | 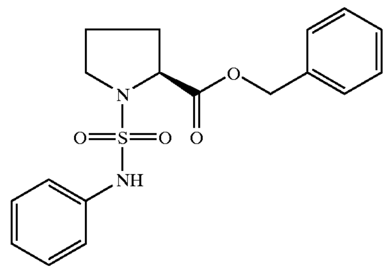 | NT | NT | NT |
| 29 | 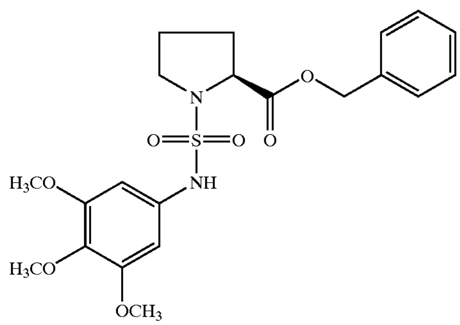 | NT | NT | NT |
| 31 | 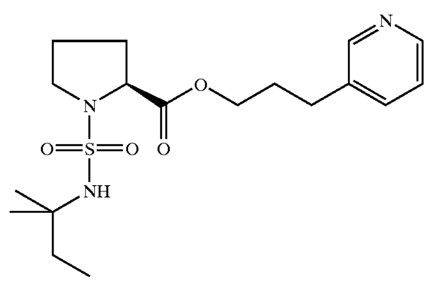 | 0.001–1 $\mu$M | 4.5 | 2.79 |
| 33 | 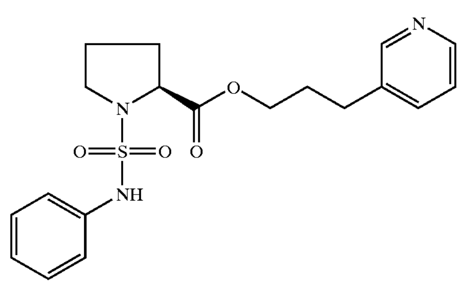 | 0.001–1 $\mu$M | 14 | NT |
| 34 | 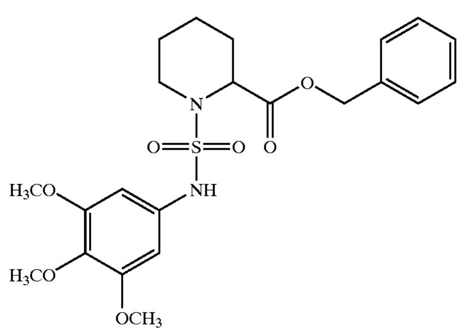 | NT | NT | NT |

TABLE 1-continued

| Compound Number | Molecular Structure | Neurite-Outgrowth Activity (PC-12) | Microcalorimetry $K_d$ ($\mu$M) | Rotamase $K_{i(app)}$ ($\mu$M) |
|---|---|---|---|---|
| 35 | 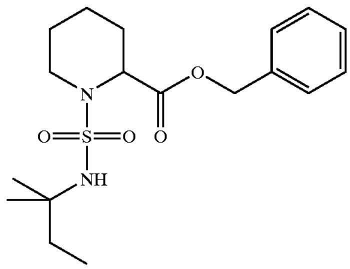 | NT | NT | NT |
| 36 | 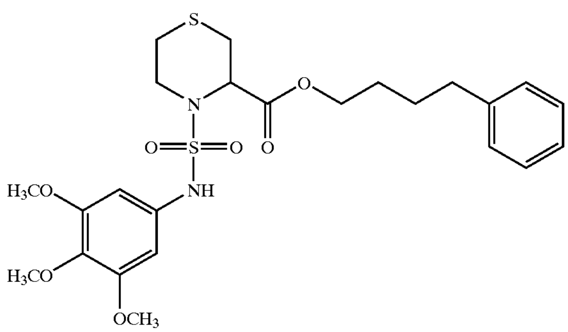 | NT | NT | NT |
| 37 | 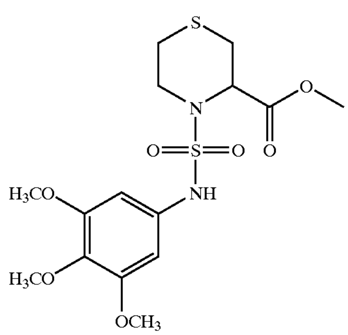 | NT | NT | NT |
| 38 | 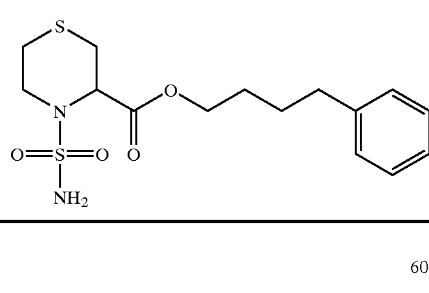 | NT | NT | NT |

NT = not tested

The affinity for FKBP-12 (Ki) for the compounds set forth in Table 2 were measured using the assay set forth below:

In a quartz cuvette, a final 1 mL buffer concentration was reached (50 mM Hepes, 100 mM NaCl, pH 8.0). Within this final reaction volume, 3.5 μL 20 mM FKBP-12 (in 50 mM Hepes, 100 mM NaCl, pH 8.0) and 10 μL test compound in DMSO were added. The reaction was initiated by adding 10 μL chymotrypsin (100 mg/mL in 1 mM HCl) followed by 5 μL (1–20 mM succinyl-Ala-Leu-Pro-Phe-pNA in 240 mM LiCl/TFE).

The absorbance at 390 nM versus time was monitored for up to 400 seconds. Rate constants were determined from the absorbance versus time plots generated.

TABLE 2

| Compound Number | Structure | FKBP12 Kiapps, μM | NAME |
|---|---|---|---|
| 27 | 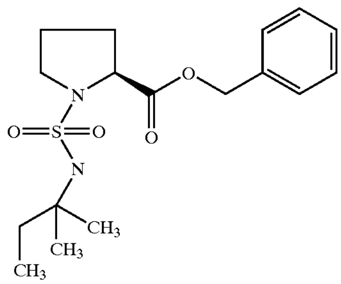 | 2.8 | 1-(1,1-Dimethyl-propylsulfamoyl)-pyrrolidine-2S-carboxylic acid benzyl ester |
| 28 | 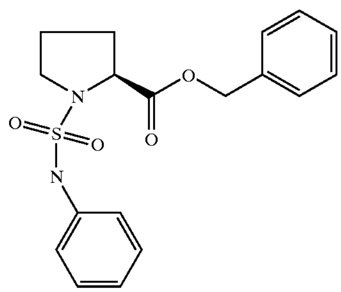 | 19.7 | 1-Phenylsulfamoyl-pyrrolidine-2S-carboxylic acid benzyl ester |
| 15 | 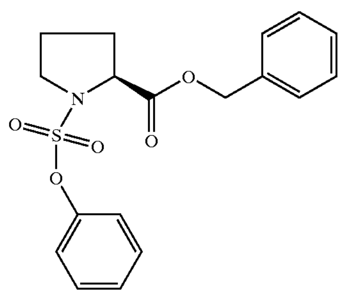 | 27.7 | 1-Phenoxysulfonyl-pyrrolidine-2S-carboxylic acid benzyl ester |
| 31 | 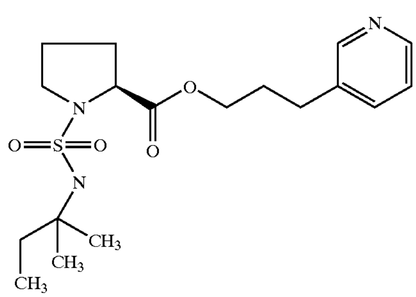 | 2.79<br>1.1 | 1-(1,1-Dimethyl-propylsulfamoyl)-pyrrolidine-2S-carboxylic acid 3-pyridin-3-yl-propyl ester |
| 29 | 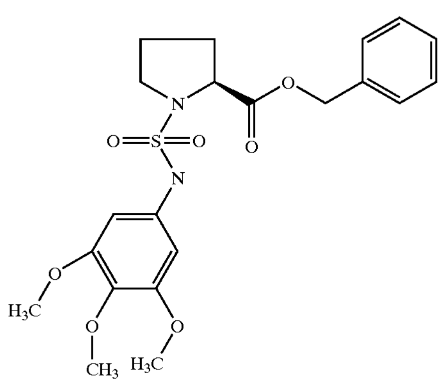 | 34.4 | 1-(3,4,5-Trimethoxy-phenylsulfamoyl)-pyrrolidine-2S-carboxylic acid benzyl ester |

TABLE 2-continued

| Compound Number | Structure | FKBP12 Kiapps, μM | NAME |
| --- | --- | --- | --- |
| 24 | 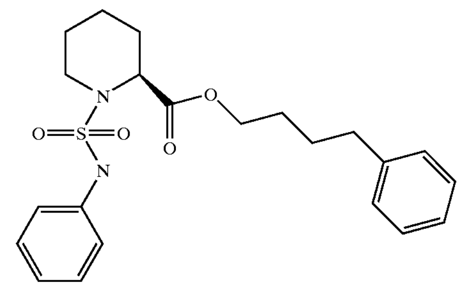 | 1.16<br>0.508 | 1-Phenylsulfamoyl-piperidine-2S-carboxylic acid 4-phenyl-butyl ester |
| 25 | 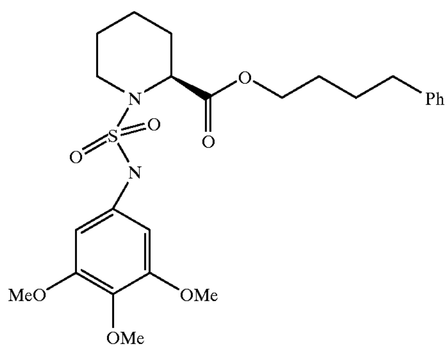 | 0.2<br>0.18 | 1-(3,4,5-Trimethoxy-phenylsulfamoyl)-piperidine-2S-carboxylic acid 4-phenyl-butyl ester |
| 13 | 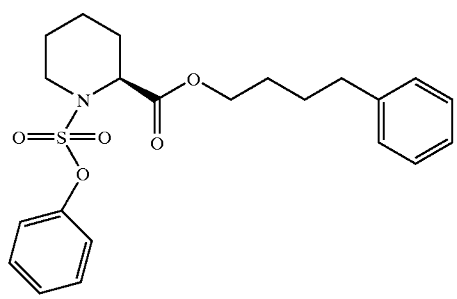 | 6.5 | 1-Phenoxysulfonyl-piperidine-2S-carboxylic acid 4-phenyl-butyl ester |
| 33 | 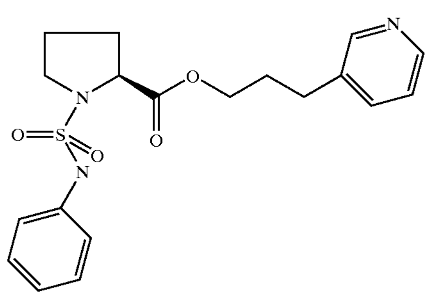 | 3.96 | 1-Phenylsulfamoyl-pyrrolidine-2S-carboxylic acid 3-pyridin-3-yl-propyl ester |
| 26 | 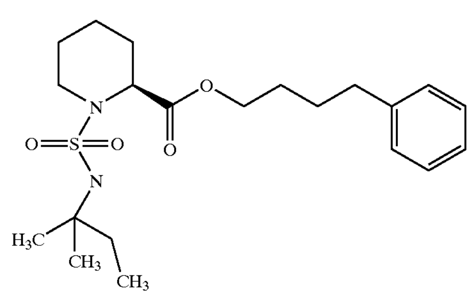 | 0.193<br>0.218 | 1-(1,1-Dimethyl-propylsulfamoyl)-piperidine-2S-carboxylic acid 4-phenyl-butyl ester |

TABLE 2-continued

| Compound Number | Structure | FKBP12 Kiapps, μM | NAME |
|---|---|---|---|
| 22 | 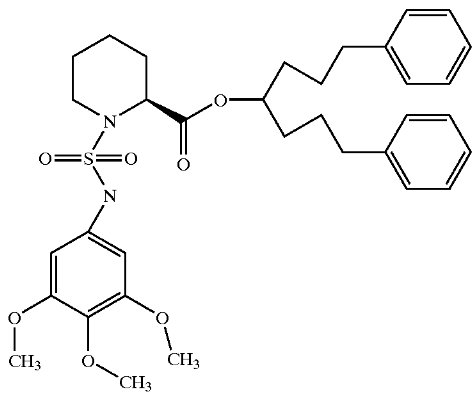 | 0.382<br>0.086 | 1-(3,4,5-Trimethoxy-phenylsulfamoyl)-piperidine-2S-carboxylic acid 4-phenyl-1-(3-phenyl-propyl)-butyl ester |
| 23 | 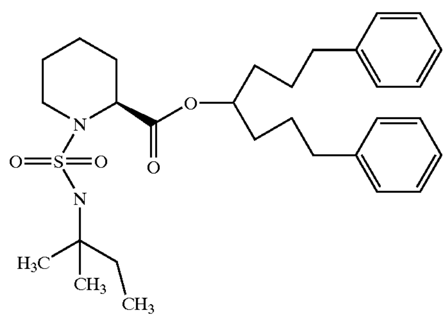 | 6.99<br>0.083 | 1-(1,1-Dimethyl-propylsulfamoyl)-piperidine-2S-carboxylic acid 4-phenyl-1-(3-phenyl-propyl)-butyl ester |
| 36 | 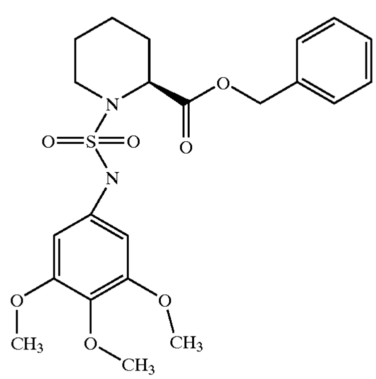 | 0.398 | 1-(3,4,5-Trimethoxy-phenylsulfamoyl)-piperidine-2S-carboxylic acid benzyl ester |
| 38 | 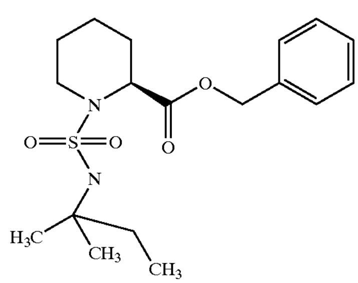 | 0.678 | 1-(1,1-Dimethyl-propylsulfamoyl)-piperidine-2S-carboxylic acid benzyl ester |

TABLE 2-continued

| Compound Number | Structure | FKBP12 Kiapps, μM | NAME |
|---|---|---|---|
| 68 | 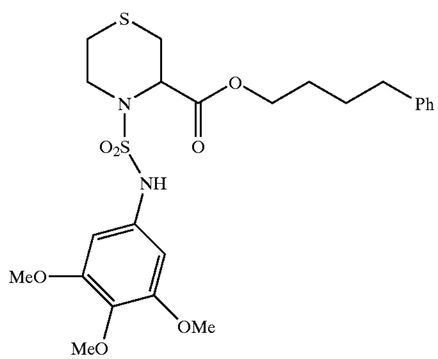 | 4.41<br>6.4 | 4-(3,4,5-Trimethoxy-phenylsulfamoyl)-thiomorpholine-3-carboxylic acid 4-phenyl-butyl ester |
| 67 | 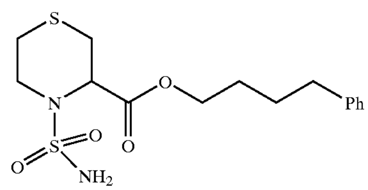 | 329<br>267 | 4-Sulfamoyl-thiomorpholine-3-carboxylic acid 4-phenyl-butyl ester |
| 61 | 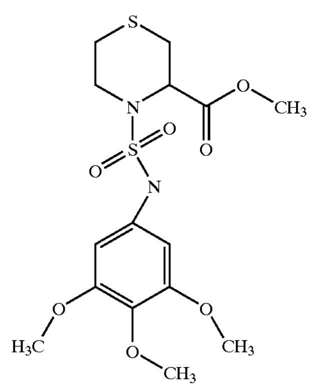 | NT | 4-(3,4,5-Trimethoxy-phenylsulfamoyl)-thiomorpholine-3-carboxylic acid methyl ester |
| 37 | 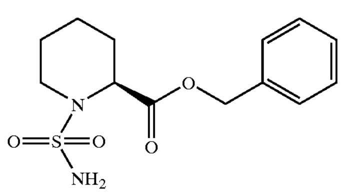 | 122 | 1-Sulfamoyl-piperidine-2S-carboxylic acid benzyl ester |
| 39 | 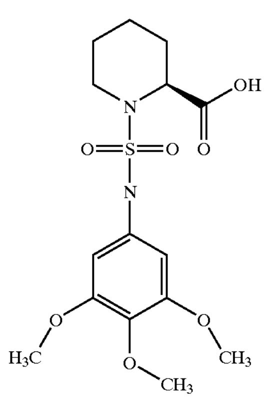 | >100 | 1-(3,4,5-Trimethoxy-phenylsulfamoyl)-piperidine-2S-carboxylic acid |

TABLE 2-continued

| Compound Number | Structure | FKBP12 Kiapps, μM | NAME |
|---|---|---|---|
| 41 | 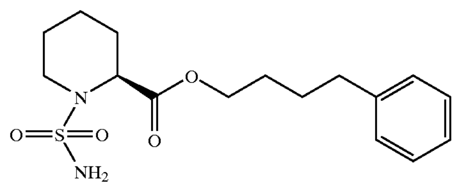 | 38 | 1-Sulfamoyl-piperidine-2S-carboxylic acid 4-phenyl-butyl ester |
| 40 | 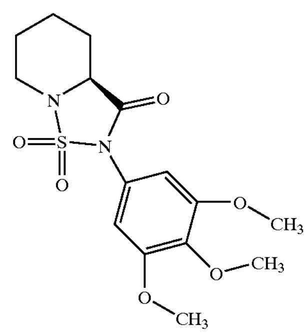 | 228 | 1,1-Dioxo-2-(3,4,5-trimethoxy-phenyl)-hexahydro-1-[1,2,5]thiadiazolo[2,3-a]pyridin-3-one |
| 42 | 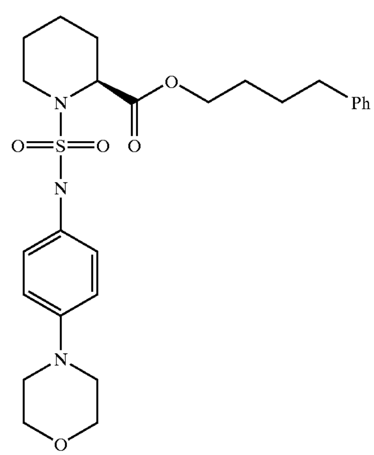 | 0.266 | 1-(4-Morpholin-4-yl-phenylsulfamoyl)-piperidine-2S-carboxylic acid 4-phenyl-butyl ester |
| 43 | 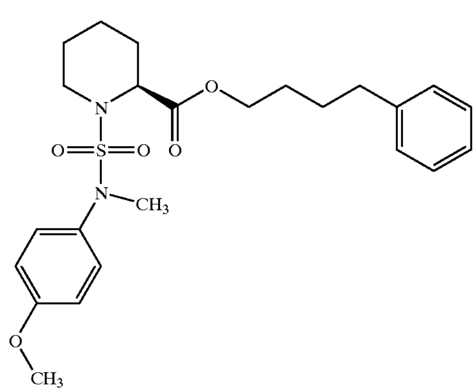 | 19.2 | 1-[(4-Methoxy-phenyl)-methyl-sulfamoyl]-piperidine-2S-carboxylic acid 4-phenyl-butyl ester |

TABLE 2-continued

| Compound Number | Structure | FKBP12 Kiapps, µM | NAME |
|---|---|---|---|
| 44 | 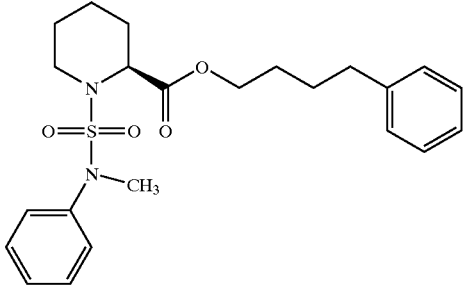 | 12 | 1-(Methyl-phenyl-sulfamoyl)-piperidine-2S-carboxylic acid 4-phenyl-butyl ester |
| 45 | 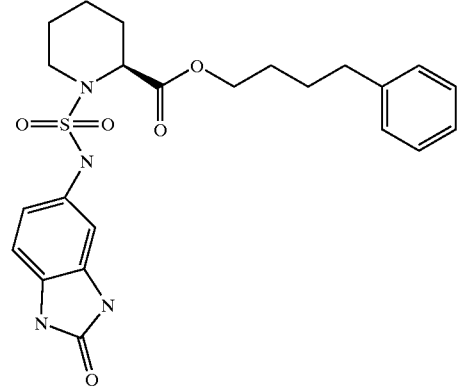 | 0.084 | 1-(2-Oxo-2,3-dihydro-1H-benzoimidazol-5-ylsulfamoyl)-piperidine-2-carboxylic acid 4-phenyl-butyl ester |
| 46 | 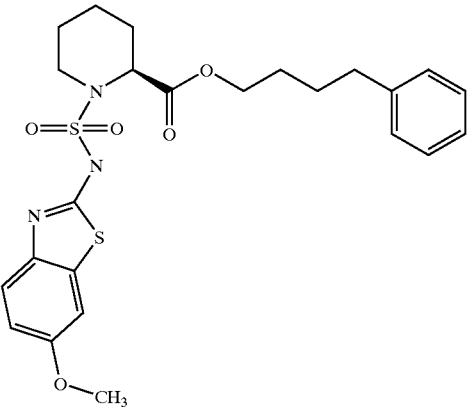 | 37 | 1-(6-Methoxy-benzothiazol-2-ylsulfamoyl)-piperidine-2S-carboxylic acid 4-phenyl-butyl ester |
| 47 | 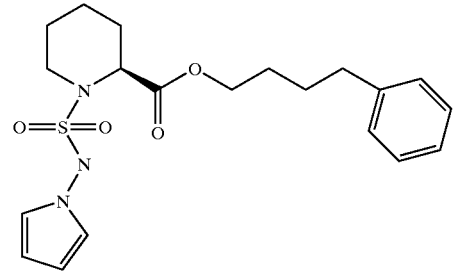 | 1.6 | 1-(Pyrrol-1-ylsulfamoyl)-piperidine-2S-carboxylic acid 4-phenylbutyl ester |

TABLE 2-continued

| Compound Number | Structure | FKBP12 Kiapps, μM | NAME |
|---|---|---|---|
| 75 | 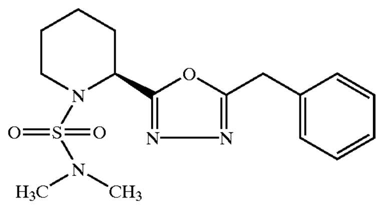 | 107 | 2S-(5-Benzyl-[1,3,4]oxadiazol-2-yl)-piperidine-1-sulfonic acid dimethylamide |
| 48 | 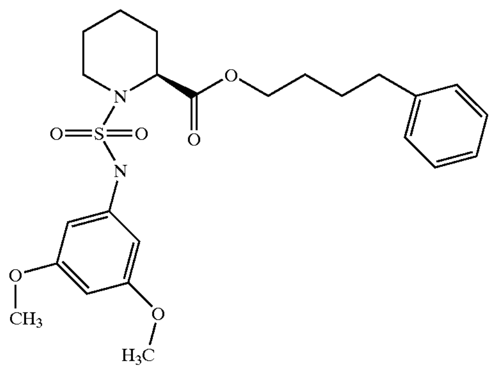 | 0.344 | 1-(3,5-Dimethoxy-phenylsulfamoyl)-piperidine-2S-carboxylic acid 4-phenyl-butyl ester |
| 78 | 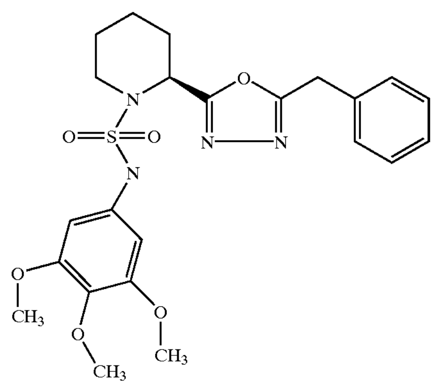 | 5.2 | 2-(5-Benzyl-[1,3,4]oxadiazol-2-yl)-piperidine-1-sulfonic acid (3,4,5-trimethoxy-phenyl)-amide |
| 76 | 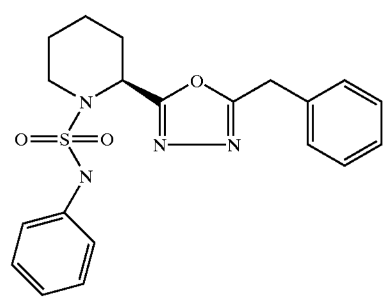 | 1.3 | 2S-(5-Benzyl-[1,3,4]oxadiazol-2-yl)-piperidine-1-sulfonic acid pheylamide |

TABLE 2-continued

| Compound Number | Structure | FKBP12 Kiapps, μM | NAME |
|---|---|---|---|
| 69 | 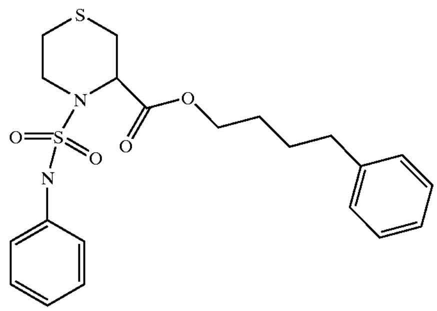 | 5.2 | 4-Phenylsulfamoyl-thiomorpholine-3-carboxylic acid 4-phenyl-butyl ester |
| 49 | 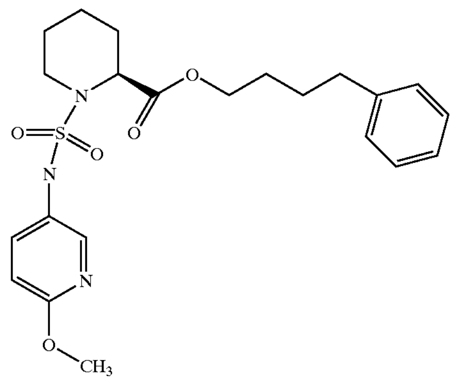 | 0.08 | 1-(6-Methyoxy-pyridin-3-ylsulfamoyl)-piperidine-2S-carboxylic acid 4-phenyl-butyl ester |
| 50 | 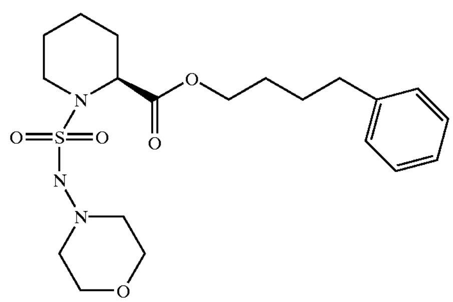 | 0.357 | 1-(Piperidin-1-ylsulfamoyl)-piperidine-2S-carboxylic acid 4-phenyl-butyl ester |
| 77 | 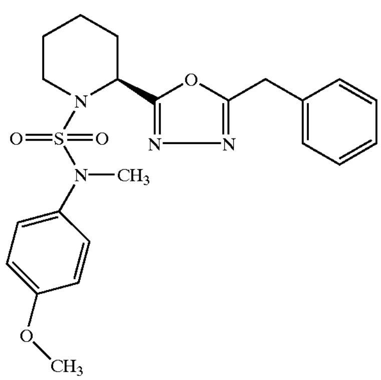 | 68 | 2-(5-Benzyl-[1,3,4]oxadiazol-2-yl)-piperidine-1-sulfonic acid (4-methoxy-phenyl)-methyl-amide |

TABLE 2-continued

| Compound Number | Structure | FKBP12 Kiapps, μM | NAME |
|---|---|---|---|
| 70 | 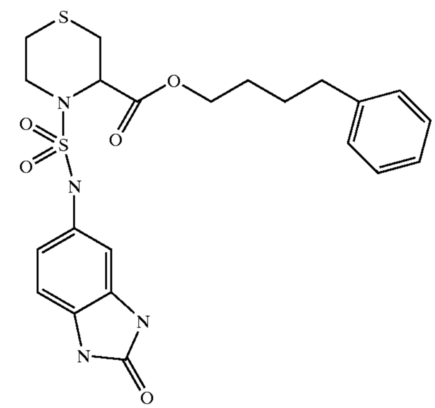 | 0.96 | 4-(2-Oxo-2,3-dihydro-1H-benzoimidazol-5-ylsulfamoyl)-thiomorpholine-3-carboxylic acid 4-phenyl-butyl ester |
| 51 | 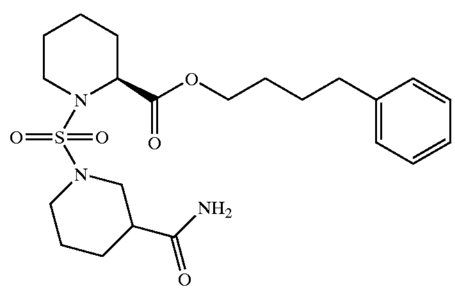 | 0.93 | 1-(3-Carbamoyl-piperidine-1-sulfonyl)-piperidine-2S-carboxylic acid 4-phenyl-butyl ester |
| 53 | 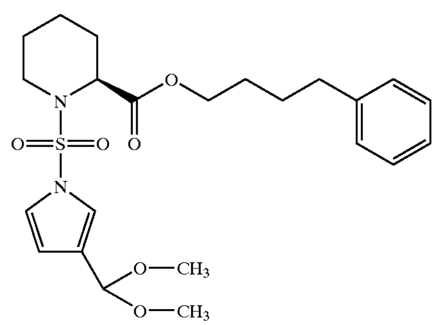 | 2.9 | 1-(3-Dimethoxymethyl-pyrazole-1-sulfonyl)-peperidine-2-carboxyic acid 4-phenyl-butyl ester |
| 54 | 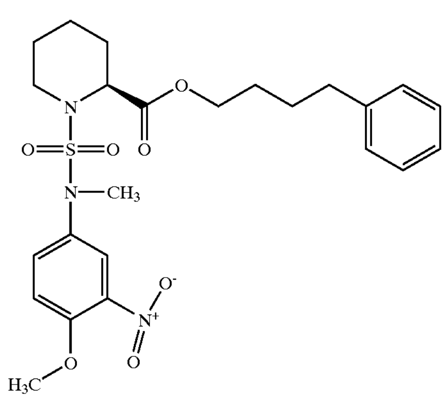 | 26 | (S)-1-[(4-Methoxy-3-nitro-phenyl)-methyl-sulfamoyl]-piperidine-2-carboxylic acid 4-phenyl-butyl ester |

TABLE 2-continued

| Compound Number | Structure | FKBP12 Kiapps, μM | NAME |
|---|---|---|---|
| 55 | 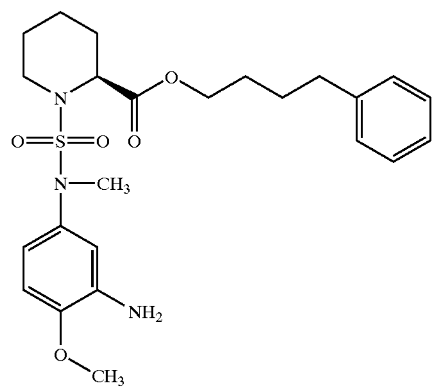 | 13.1 | (S)-1-[(3-Amino-4-methoxy-phenyl)-methyl-sulfamoyl]-piperidine-2-carboxylic acid 4-phenyl-butyl ester |
| 56 | 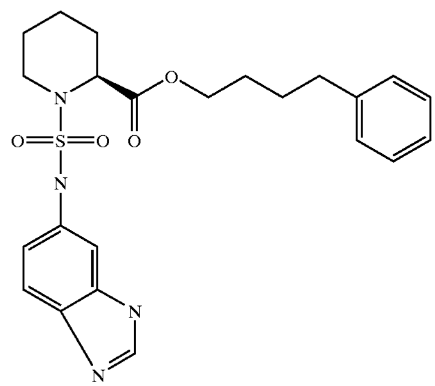 | 0.477 | (S)-1-(3H-Benzoimidazol-5-ylsulfamoyl)-piperidine-2-carboxylic acid 4-phenyl-butyl ester |
| 84 | 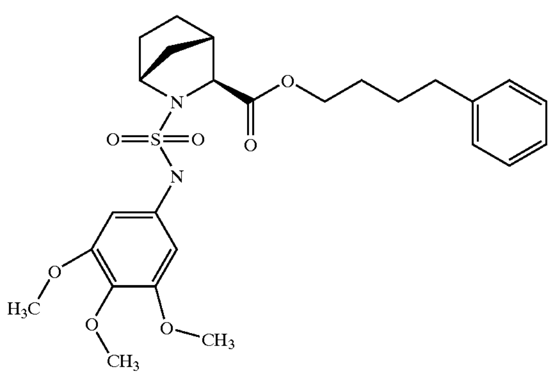 | NI at 1 μM Sol < 30 μM | 2-(3,4,5-Trimethoxy-phenylsulfamoyl)-2-aza-bicyclo[2.2.1]heptane-exo-3-carboxylic acid 4-phenyl-butyl ester |
| 85 | 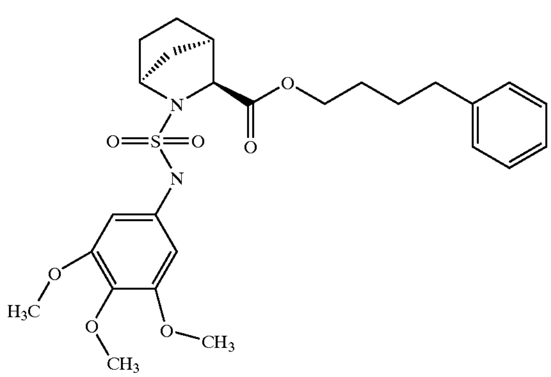 | 1.6 | 2-(3,4,5-Trimethoxy-phenylsulfamoyl)-2-aza-bicyclo[2.2.1]heptane-endo-3-carboxylic acid 4-phenyl-butyl ester |

TABLE 2-continued

| Compound Number | Structure | FKBP12 Kiapps, µM | NAME |
|---|---|---|---|
| 59 | 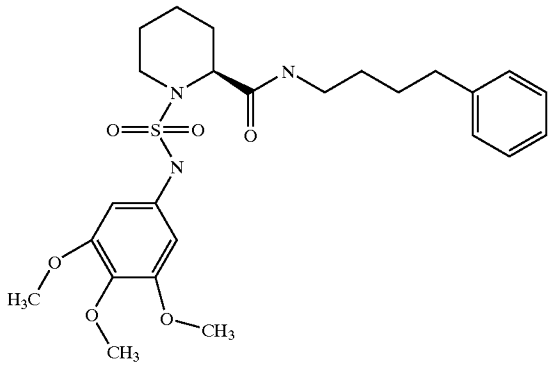 | 0.148 | (S)-1-(3,4,5-Trimethoxy-phenylsulfamoyl)-piperidine-2-carboxylic acid (4-phenyl-butyl)-amide |
| 52 | 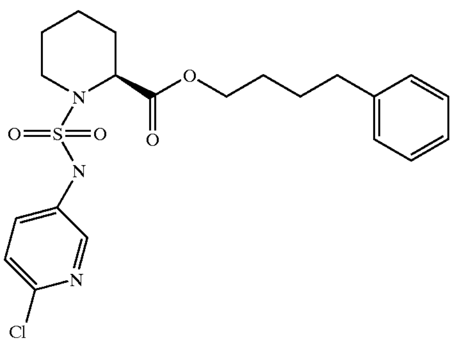 | 0.152 | (S)-1-(6-Chloro-pyridin-3-ylsulfamoyl)-piperidine-2-carboxylic acid 4-phenyl-butyl ester |
| 94 | 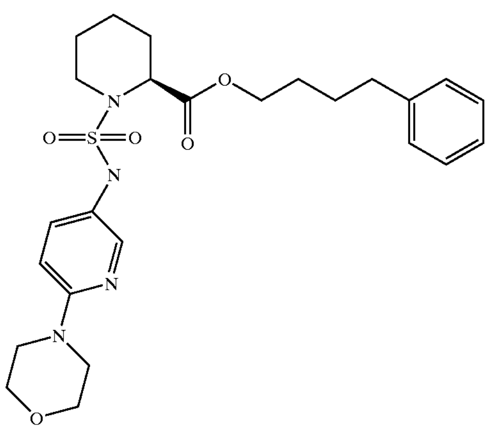 | 0.208 | (S)-1-(6-Morpholin-4-yl-pyridin-3-ylsulfamoyl)-piperidine-2-carboxylic acid 4-phenyl-butyl ester |
| 95 | 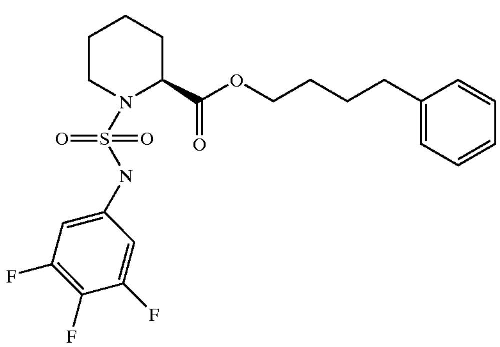 | 0.435 | (S)-1-(3,4,5-Trifluoro-phenylsulfamoyl)-piperidine-2-carboxylic acid 4-phenyl-butyl ester |

TABLE 2-continued

| Compound Number | Structure | FKBP12 Kiapps, μM | NAME |
|---|---|---|---|
| 86 | 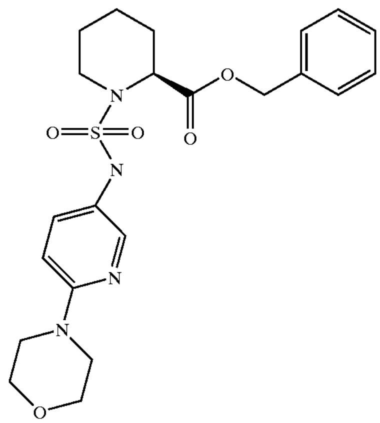 | 1.79 1.17 | (S)-1-(6-Morpholin-4-yl-pyridine-3-ylsulfamoyl)-piperidine-2-carboxylic acid benzyl ester |
| 87 | Chiral | 0.76 | 1-(6-Methyoxy-pyridin-3-ylsulfamoyl)-piperidine-2S-carboxylic acid benzyl ester |
| 96 | Chiral | 0.44 | (S)-1-(6-Trifluoromethyl-pyridin-3-ylsulfamoyl)-piperidine-2-carboxylic acid 4-phenyl-butyl ester |
| 88 | Chiral | 0.837 | (S)-1-(cis-2,6-Dimethyl-morpholine-4-sulfonyl)-piperidine-2-carboxylic acid benzyl ester |

TABLE 2-continued

| Compound Number | Structure | FKBP12 Kiapps, μM | NAME |
|---|---|---|---|
| 102 | 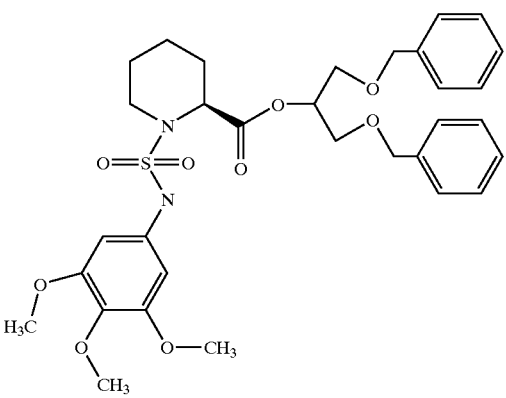 | Chiral 0.171 | (S)-1-(3,4,5-Trimethoxy-phenylsulfamoyl)-piperidine-2-carboxylic acid 2-benzyloxy-1-benzyloxymethyl-ethyl ester |
| 103 | 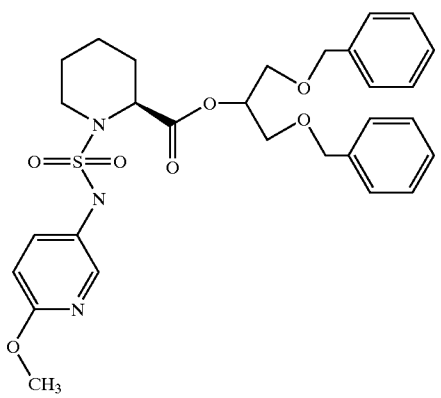 | Chiral 0.039 | (S)-1-(6-Methoxy-pyridin-3-ylsulfamoyl)-piperidine-2-carboxylic acid 2-benzyloxy-1-benzyloxymethyl-ethyl ester |
| 104 | 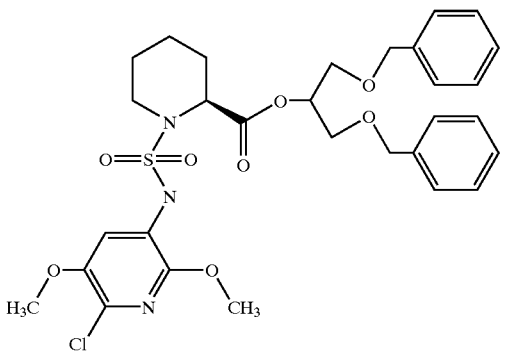 | Chiral 7.1 | (S)-1-(4-Chloro-2,5-dimethoxy-phenylsulfamoyl)-piperidine-2-carboxylic acid 2-benzyloxy-1-benzyloxymethyl-ethyl ester |

TABLE 2-continued

| Compound Number | Structure | FKBP12 Kiapps, μM | NAME |
|---|---|---|---|
| 105 | Chiral | 0.033 | (S)-1-(Pyridin-3-ylsulfamoyl)-piperidine-2-carboxylic acid 2-benzyloxy-1-benzyloxymethyl-ethyl ester |
| 106 | Chiral | 0.115 | (S)-1-(6-Morpholin-4-yl-pyridin-3-ylsulfamoyl)-piperidine-2-carboxylic acid 2-benzyloxy-1-benzyloxymethyl-ethyl ester |
| 107 | Chiral | 0.088 | (S)-1-(6-Methyl-pyridin-3-ylsulfamoyl)-piperidine-2-carboxylic acid 2-benzyloxy-1-benzyloxymethyl-ethyl ester |

TABLE 2-continued

| Compound Number | Structure | FKBP12 Kiapps, μM | NAME |
| --- | --- | --- | --- |
| 108 | Chiral | 0.127 | (S)-1-(Morpholin-4-yl-trifluoromethyl-pyridin-3-ylsulfamoyl)-piperidine-2-carboxylic acid 2-benzyloxy-1-benzyloxymethyl-ethyl ester |
| 114 | Chiral | 1.11 | (S)-1-(1,1-Dimethyl-propylsulfamoyl)-pyrrolidine-2-carboxylic acid(3-pyridin-3-yl-propyl)-amide |
| 97 | Chiral | 0.073 | (S)-1-(Pyridin-3-ylsulfamoyl)-piperidine-2-carboxylic acid 4-phenyl-butyl ester |
| 115 | Chiral | 20.4 | (S)-1-(Pyridin-3-ylsulfamoyl)-pyrrolidine-2-carboxylic acid benzyl ester |

TABLE 2-continued
| Compound Number | Structure | | FKBP12 Kiapps, μM | NAME |
|---|---|---|---|---|
| 118 | 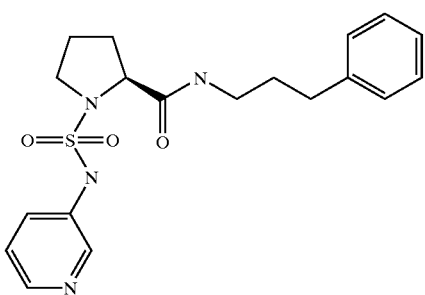 | Chiral | 16.9 | (S)-1-(Pyridin-3-ylsulfamoyl)-pyrrolidine-2-carboxylic acid (3-phenyl-propyl)-amide |
| 116 | 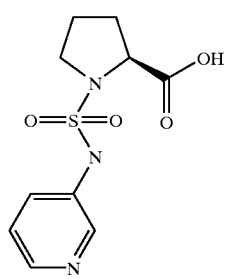 | Chiral | NSI @ 20 | (S)-1-(Pyridin-3-ylsulfamoyl)-pyrrolidine-2-carboxylic acid |
| 117 | 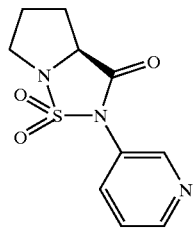 | Chiral | NSI @ 20 | (S)-1,1-Dioxo-2-pyridin-3-yl-hexahydro-1λ$^6$-thia-2,6a-diaza-pentalen-3-one |
| 90 | 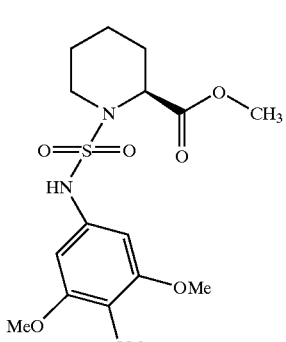 | | 6.9 | (S)-1-(3,4,5-Trimethoxy-phenylsulfamoyl)-piperidine-2-carboxylic acid methyl ester |

TABLE 2-continued

| Compound Number | Structure | FKBP12 Kiapps, μM | NAME |
|---|---|---|---|
| 91 | Chiral | 1.3 | (S)-1-(3,4,5-Trimethoxy-phenylsulfamoyl)-piperidine-2-carboxylic acid(3-piperidin-1-yl-propyl)-amide |
| 99 | Chiral | NI @ 20 | (S)-1-(Hydroxy-phenyl-sulfamoyl)-piperidine-2-carboxylic acid 4-phenyl-butyl ester |
| 93 | 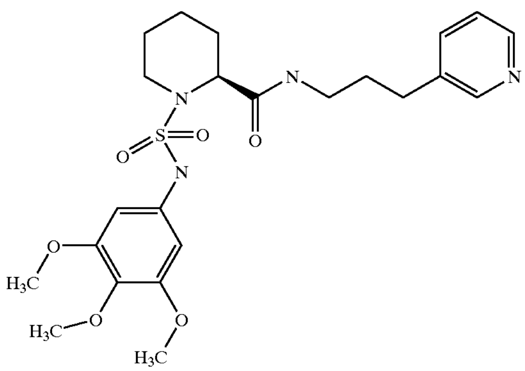 | 0.2 | (S)-1-(3,4,5-Trimethoxy-phenylsulfamoyl)-piperidine-2-carboxylic acid (3-pyridin-3-yl-propyl)-amide |
| 112 | Chiral | 0.041 | (S)-1-(3,4,5-Trimethoxy-phenylsulfamoyl)-piperidine-2-carboxylic acid [(S)-2-methyl-1-(pyridin-3-ylmethoxymethyl)-propyl]-amide |

TABLE 2-continued

| Compound Number | Structure | FKBP12 Kiapps, μM | NAME |
|---|---|---|---|
| 98 | Chiral | 0.218 | (S)-1-(4-Carboxy-3-methoxy-phenylsulfamoyl)-piperidine-2-carboxylic acid 4-phenyl-butyl ester |
| 113 | Chiral | 33 | Benzyl-phenethyl-carbamic acid (S)-1-(dimethyl-propylsulfamoyl)-pyrrolidin-2-ylmethyl ester |
| 119 | 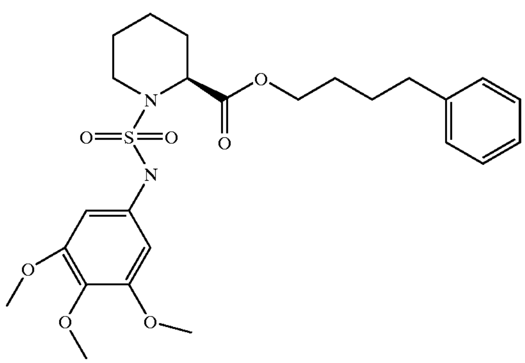 | 1.3 | (S)-2-(6-Phenyl-hexanoyl)-piperidine-1-sulfonic acid (3,4,5-trimethoxy-phenyl)-amide |

NI = no inhibition, NSI = no significant inhibition, NT not tested

FKBP-inhibiting agents of the invention, such as the compounds exemplified above, may be used to prepare pharmaceutical compositions, such as those described below.

The pharmaceutical compositions of this invention comprise an effective neurite-outgrowth-stimulating compound of formula (I) or (II) and an inert, pharmaceutically acceptable carrier or diluent. The pharmaceutical compositions may additionally comprise a neurotrophic factor. These compositions are prepared in unit-dosage forms appropriate for various routes of administration.

In one embodiment, efficacious levels of non-peptide rotamase-inhibiting compounds are provided so as to provide therapeutic benefits involving regulation of FKBP. By "efficacious levels" of compounds is meant levels in which the FKBP binding of FKBP12 is, at a minimum, regulated.

The compounds may be administered in the form of a prodrug which, in general, is designed to enhance absorption and is cleaved in vivo to form the active component. Efficacious levels may also be achieved by administration of pharmaceutically active metabolites (products of metabolic conversions) of the compound.

A compound of formula (I) or (II) is administered in a suitable dosage form prepared by combining a therapeutically effective amount (i.e., an efficacious level sufficient to achieve the desired therapeutic effect through FKBP regulation) of a compound of formula (I) or (II) (as an active ingredient) with standard pharmaceutical carriers or diluents according to conventional procedures. These procedures may involve mixing, granulating, and compressing or dissolving the ingredients as appropriate to attain the desired preparation.

The pharmaceutical carrier employed may be in any suitable form, for example, either a solid or liquid. Exemplary solid carriers include lactose, terra alba, sucrose, talc, gelatin, agar, pectin, acacia, magnesium stearate, stearic acid and the like. Exemplary liquid carriers include syrup, peanut oil, olive oil, water and the like. Similarly, the carrier or diluent may include time-delay material known in the art, such as glyceryl monostearate or glyceryl distearate, alone or with a wax, ethylcellulose, hydroxypropylmethylcellulose, methylmethacrylate or the like.

A variety of pharmaceutical forms can be employed. For example, if a solid carrier is used, the preparation can be tableted, placed in a hard gelatin capsule in powder or pellet form, or formed into a troche or lozenge. The amount of solid carrier may vary, but preferably will be from about 25 mg to about 1 g. If a liquid carrier is used, the preparation will preferably be in the form of syrup, emulsion, soft gelatin capsule, sterile injectable solution or suspension in an ampoule or vial, or nonaqueous liquid suspension.

To obtain a stable water-soluble dose form, a pharmaceutically acceptable salt of a compound of formula (I) or (II) may be dissolved in an aqueous solution of an organic or inorganic acid, such as 0.3 M solution of succinic acid, or more preferably, citric acid. If a soluble salt form is not available, the compound of formula (I) may be dissolved in a suitable co-solvent or combination of co-solvents. Examples of suitable co-solvents include alcohol, propylene glycol, polyethylene glycol 300, polysorbate 80, glycerin and the like in concentrations ranging from 0 to 60% of the total volume. In a preferred embodiment, the active compound of formula (I) or (II) is dissolved in DMSO and diluted with water. The composition may also be in the form of a solution of a salt form of the active ingredient in an appropriate aqueous vehicle, such as water or isotonic saline or dextrose solution.

It will be appreciated that the actual preferred dosages of the compounds of formula (I) or (II) used in the compositions of this invention may vary according to the particular complex being used, the particular composition formulated, the mode of administration and the particular site, and the host and disease being treated. Optimal dosages for a given set of conditions can be ascertained by those skilled in the art using conventional dosage-determination tests, e.g., in view of the experimental data provided herein. For oral administration, the usual daily dose generally employed is from about 0.001 to about 1000 mg/kg of body weight, with courses of treatment repeated at appropriate intervals. Initial pharmacokinetics for humans may be determined from the rat model as described by Gold et al., *Experimental Neurology*, 147:269–278 (1997).

The pharmaceutical compositions containing active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more physiologically acceptable carriers comprising excipients and/or auxiliaries which facilitate processing of the active compounds into preparations that can be used pharmaceutically. Of course, the appropriate formulation is dependent upon the route of administration chosen.

For oral administration, the compounds can be formulated readily by combining the active compounds with pharmaceutically acceptable carriers known in the art. Such carriers allow the compounds of the invention to be formulated as tablets, pills, dragees, capsules, liquids, gels, syrups, slurries, suspensions and the like, for oral ingestion by a patient to be treated. Pharmaceutical preparations for oral use can be obtained by combining an active compound with a solid excipient, optionally grinding the resulting mixture, and processing the mixture of granules, after adding suitable auxiliaries, if desired, to obtain tablets or dragee cores. Suitable excipients include, e.g.: fillers such as sugars, including lactose, sucrose, mannitol, or sorbitol; and cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as cross-linked polyvinylpyrrolidone, agar, or alginic acid or a salt thereof such as sodium alginate.

Dragee cores are provided with suitable coatings. For this purpose, concentrated sugar solutions may be used, which may optionally contain gum arabic, polyvinylpyrrolidone, Carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparation forms that can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate, and, optionally, stabilizers. In soft capsules, the active compounds may be dissolved or suspended in suitable liquids, such as fatty oils, liquid paraffin, or liquid polyethylene glycols. In addition, stabilizers may be added. All formulations for oral administration should be in dosages suitable for such administration. For buccal administration, the compositions may take the form of tablets or lozenges formulated in a conventional manner.

An example for preparing an oral pharmaceutical composition of this invention is as follows: 100 mg of a compound of formula (I) or (II) is mixed with 750 mg of lactose, and the mixture is incorporated into an oral unit-dosage form, such as a hard gelatin capsule, which is suitable for oral administration.

For administration by inhalation, the compounds according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit-dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation and may be selected form those known in the art.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles for preparing such formulations include fatty oils such as sesame oil, or synthetic fatty acid esters such as ethyl oleate or triglycerides, or liposomes. Aqueous injection suspensions may contain substances that increase the viscosity of the suspension, such as sodium carboxymethylcellulose, sorbitol, or dextran. Optionally, the suspension may also contain suitable stabilizers or agents which increase the solubility of the compounds to allow for the preparation of highly concentrated solutions.

A parenteral pharmaceutical composition of this invention suitable for administration by injection may be prepared as follows: 100 mg of a compound of formula (I) or (II) is mixed with 10 ml of a lipophilic solvent such as a fatty oil, and the mixture is incorporated into a unit-dosage form suitable for administration by injection as an emulsion.

Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long-acting formulations may be administered by implantation (for example, subcutaneously or intramuscularly) or by intramuscular injection. For example, the compounds may be formulated with suitable polymeric or hydrophobic materials (for example, as an emulsion in an acceptable oil) or ion-exchange resins, or as sparingly soluble derivatives, for example, as a sparingly soluble salt.

A suitable pharmaceutical carrier for the hydrophobic compounds of the invention is a co-solvent system comprising benzyl alcohol, a nonpolar surfactant, a water-miscible organic polymer, and an aqueous phase. The co-solvent system may be the VPD co-solvent system (VPD is a solution of 3% w/v benzyl alcohol, 8% w/v of the nonpolar surfactant polysorbate 80, and 65% w/v polyethylene glycol 300, made up to volume in absolute ethanol). The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g., polyvinylpyrrolidone; and other sugars or polysaccharides may be substituted for dextrose.

Alternatively, other delivery systems for hydrophobic pharmaceutical compounds may be employed. Liposomes and emulsions are well known examples of delivery vehicles or carriers for hydrophobic drugs. Certain organic solvents such as dimethylsulfoxide also may be employed, although usually at the cost of greater toxicity. Additionally, the compounds may be delivered using a sustained-release system, such as semipermeable matrices of solid hydrophobic polymers containing the therapeutic agents. Various sustained-release materials have been established and are known by those skilled in the art. Sustained-release capsules may, depending on their chemical nature, release the compounds for a period of a few weeks up to over 100 days. Depending on the chemical nature and the biological stability of the therapeutic reagent, additional strategies for protein stabilization may be employed.

The pharmaceutical compositions also may comprise suitable solid- or gel- phase carriers or excipients. Examples of such carriers or excipients include calcium carbonate, calcium phosphate, various sugars, starches, cellulose derivatives, gelatin, and polymers such as polyethylene glycols.

Numerous neurotrophic factors have been identified in the art and any of those factors may be utilized in the compositions of this invention. As used herein, the term "neurotrophic factor" refers to substances that are capable of stimulating growth or proliferation of nervous tissue (but excluding the FKBP-rotamase inhibiting compounds of the invention), e.g., nerve growth factor (NGF), insulin growth factor (IGF-1) and its active truncated derivatives (gIGF-1), acidic and basic fibroblast growth factor (aFGF and bFGF, respectively), platelet-derived growth factors (PDGF), brain-derived growth factors (BDNF), ciliary neurotrophic factors (CNTF), glial cell line derived neurotrophic factor (GDNF), neurotrophin-3 (NT-3), and neurotrophin 4/5 (NT-4/5). Pharmaceutical compositions may include as active ingredients, in addition to one or more agents of the invention, one or more of such neurotrophic factors. The most preferred neurotrophic factor for use in the compositions of this invention is NGF.

Other components of the pharmaceutically acceptable compositions of this invention may include benzyl alcohol or other suitable preservatives, absorption promoters to enhance bioavailability, fluorocarbons, and/or other conventional solubilizing or dispersing agents.

A pharmaceutical composition contains a total amount of the active ingredient(s) sufficient to achieve the intended therapeutic effect. More specifically, the pharmaceutical composition contains a therapeutically effective amount (i.e., an amount effective to prevent development of or to alleviate the existing symptoms of a disease or condition mediated by FKBP) of an FKBP-inhibiting agent of the invention. The total amounts of the FKPB-inhibitory agent of the invention and any optional neurotrophic factor that may be combined with the carrier materials to produce a single-dosage form will vary depending upon the host treated and the particular mode of administration. Preferably, the compositions of the invention each contains both an FKBP-inhibiting agent and a neurotrophic factor, with the FKBP-inhibiting agent acting to potentiate the activity of the neurotrophic factor to enhance stimulation of neurite outgrowth. The amount of neurotrophic factor in such compositions is advantageously less than the amount required in a monotherapy utilizing only the factor. Preferably, the compositions are formulated so that a dosage of between 0.01 to 100 mg/kg body weight/day of a FKBP12-inhibiting agent is administered and a dosage of between 0.01 to 100 $\mu$g/kg body weight/day of a neurotrophic factor is administered to a patient receiving the compositions.

A pharmaceutical composition of the invention may be used in a method of inhibiting the rotamase enzyme activity of an FK-506 binding protein, comprising administering the composition to a patient. The inventive compositions may also be used to stimulate the growth of neurites in nerve cells, to stimulate nerve regeneration, or to promote neuronal regeneration. Preferably, the composition further comprises a neurotrophic factor.

While the invention has been illustrated by reference to specific and preferred embodiments, those skilled in the art will recognize, e.g., through routine experimentation and practice of the invention, that variations and modifications may be made. Thus, the invention is intended not to be limited by the foregoing description, but to be defined by the appended claims and their equivalents.

What is claimed is:

1. A compound of formula:

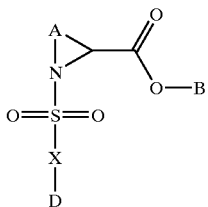

or a pharmaceutically acceptable salt or solvate thereof, wherein:

A is $C_3$–$C_5$ alkylene optionally substituted with one or more suitable substituents excluding 6-membered fused aryl groups and optionally any one of the $CH_2$ groups of the alkylene group may be replaced by O, S, SO or $SO_2$;

B is

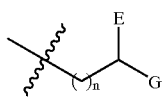

where E and G are independently Ar, H, $C_1$–$C_6$ straight or branched alkyl, $C_1$–$C_6$ straight or branched alkenyl, $C_1$–$C_6$ straight or branched alkyl or alkenyl that is substituted with a $C_5$–$C_7$ cycloalkyl, $C_1$–$C_6$ straight or branched alkyl or alkenyl that is substituted with a $C_5$–$C_7$ cycloalkenyl, or Ar substituted with $C_1$–$C_6$ straight or branched alkyl or alkenyl, wherein, in each case, one or two of the $CH_2$ groups of the alkyl or alkenyl chains may be replaced by 1–2 moieties selected from the group consisting of oxygen, sulfur, SO, $SO_2$, and

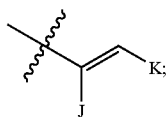

where J is H, $C_1$–$C_6$ straight or branched alkyl, or $C_1$–$C_6$ straight or branched alkenyl; and K is Ar or substituted 5–7 membered cycloalkyl with substituents at positions 3 and 4 which are independently selected from the group consisting of H, OH, —O—$(CH_2)_m$-alkyl, —O—$(CH_2)_m$-alkenyl and carbonyl, wherein m is 1–4;

where Ar is selected from the group consisting of unsubstituted and substituted phenyl, 1-napthyl, 2-naphthyl, 2-furyl, 3-furyl, 2-thienyl, 3-thienyl, 2-pyridyl, 3-pyridyl, 4-pyridyl, and monocyclic and bicyclic heterocyclic ring systems with each ring having 5 or 6 ring atoms optionally, 1–4 heteroatoms independently selected from O, N and S; wherein when substituted, the substituents are from one to three substituents independently selected from the group consisting of hydrogen, halo, hydroxyl, nitro, trifluoromethyl, trifluoromethoxy, $C_1$–$C_6$ straight or branched alkyl, $C_2$–$C_6$ straight or branched alkenyl, O—($C_1$–$C_4$ straight or branched alkyl), O—($C_2$–$C_4$ straight or branched alkenyl), O-benzyl, O-phenyl, 1,2-methylenedioxy, amino, carboxyl and phenyl; and n is an integer from 0 to 4;

D is $C_1$–$C_6$ straight or branched alkyl, $C_1$–$C_6$ straight or branched alkenyl, $C_5$–$C_7$ cycloalkyl, $C_5$–$C_7$ cycloalkenyl substituted with $C_1$–$C_4$ straight or branched alkyl or $C_1$–$C_4$ straight or branched alkenyl, [($C_2$–$C_4$)-alkyl or ($C_2$–$C_4$)-alkenyl]-Ar, or Ar excluding benzyl; and X is $NR^{10}$ or O, where $R^{10}$ is H, $C_1$–$C_4$ alkyl, $C_1$–$C_4$ alkenyl, or hydroxy.

2. A compound as claimed in claim 1, where:

A is selected from an unbranched $C_3$–$C_5$ alkylene group wherein any one of the $CH_2$ groups of the alkylene groups is optionally substituted by S;

B is

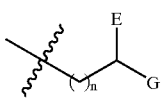

wherein E is selected from H, benzyl, 3-pyridyl, 2-phenylethyl and 3-phenylpropyl; G is selected from phenyl, 3-pyridyl, 3-phenylpropyl, 3-phenoxyphenyl and 4-phenoxyphenyl; and n is 0–4;

D is selected from phenyl, 4-methylphenyl, 4-methoxyphenyl, 2-thienyl, 2,4,6-triisopropylphenyl, 4-fluorophenyl, 3-methoxyphenyl, 2-methoxyphenyl, 3,5-dimethoxyphenyl, 3,4,5-trimethoxyphenyl, methyl, 1-naphthyl, 8-quinolyl, 1-(5-N,N-dimethylamino)-naphthyl, 4-iodophenyl, 2,4,6-trimethylphenyl, 4-nitrophenyl, 2-nitrophenyl, 4-chlorophenyl, 1,1-dimethylpropyl and E-styrenyl; and X is selected from NH and O.

3. A compound selected from the group consisting of:

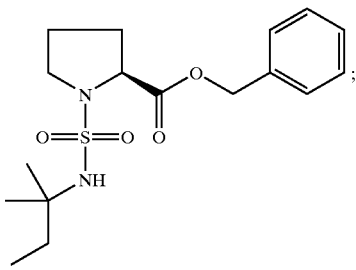

163
-continued

164
-continued

-continued

[Structure: thiomorpholine with N-sulfonyl group bearing NH-3,4,5-trimethoxyphenyl, and carboxylate ester -O-(CH2)4-phenyl]

[Structure: thiomorpholine with N-sulfonyl-NH-3,4,5-trimethoxyphenyl and methyl ester]

and

[Structure: piperidine-2-carboxylate benzyl ester with N-sulfonyl-NH-tert-amyl group]

or a pharmaceutically acceptable salt or solvate thereof.

4. A compound of formula:

[Structure showing J'-N(K')-CH(L')- with N-S(=O)(=O)-M]

or a pharmaceutically acceptable salt or solvate thereof, wherein:

J' and K' taken together with the adjacent nitrogen atom form a heterocycle ring which may contain another heteroatom;

M is selected from the group consisting of —$OR_1$, $$-N(R')-R_1, \quad -N(R')-NR_1R'', \text{ and}$$

$$-N(R')-NHR''; \text{ wherein:}$$

$R_1$ is substituted or unsubstituted alkyl, alkenyl, aryl excluding benzyl, cycloalkyl, heteroaryl, heterocycloalkyl, or cycloalkenyl, or $C(R^{11})(R^{12})(R^{13})$, wherein $R^{11}$ and $R^{12}$ each independently is substituted or unsubstituted alkyl, or $R^{11}$ and $R^{12}$ together with the atom to which they are bound form a cycloalkyl, and $R^{13}$ is H, OH, substituted or unsubstituted alkyl, aryl, heteroaryl, heterocycloalkyl, or $(CH_2)_n$—O—$W^1$, where n is 0, 1, 2, or 3, $W^1$ is $R^2$ or $C(O)R^2$, and $R^2$ is subs or unsubstituted alkyl;

R' is selected from the group consisting of hydrogen, substituted and unsubstituted alkyl, hydroxyl, and amino; or $R_1$ and R' taken together with the adjacent nitrogen atom form a substituted or unsubstituted heterocycle;

R" is hydrogen or substituted or unsubstituted alkyl; or $R_1$ and R" taken together with the adjacent nitrogen atom form a substituted or unsubstituted heterocycle;

[Structures showing two substituent patterns with X', Y', B' and $R_a$, $R_b$, Z, $R_c$, $R_d$]

L' is wherein X' is selected from the group consisting of S, O and N;

Y' is selected from O, NH, S, a direct bond, and $NR_f$, wherein $R_f$ is substituted or unsubstituted alkyl; or X' and Y' taken together with the adjacent carbon atom form a heterocycle ring;

B' is

[Structure with E', G', $(CH_2)_n$]

where n is an integer from 0 to 4;

E' a G' H are independently, substituted or unsubstituted alkyl, aryl, heteroaryl, heterocycloalkyl, alkenyl, cycloalkyl, or cycloalkenyl, wherein, in each case, one or two of the $CH_2$ groups of the alkyl or alkenyl chains may be replaced by 1–2 moieties selected from the group consisting of oxygen, sulfur, SO and $SO_2$, or

[Structure with Q, Q']

where Q' is H, or substituted or unsubstituted alkyl or alkenyl; and

Q is substituted or unsubstituted cycloalkyl, heterocycloalkyl, aryl, or heteroaryl;

$R_a$ and $R_b$ are independently hydrogen, substituted or unsubstituted alkyl or cycloalkyl;

Z is O, NH, $CH_2$ or $NR_e$, wherein $R_e$ is substituted or unsubstituted alkyl; and $R_c$ and $R_d$ are independently hydrogen,

[Structures with E', G', $(CH_2)_n$ or Q, Q']

wherein E', G', Q', Q, and n are as defined above.

5. A compound selected from the group consisting of:

167
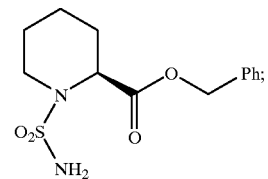 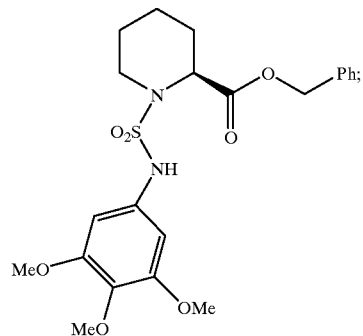
168
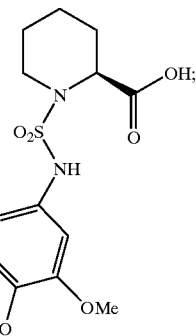
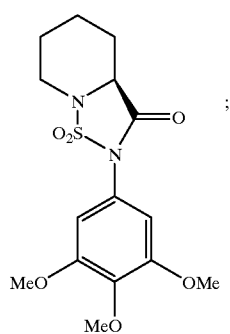 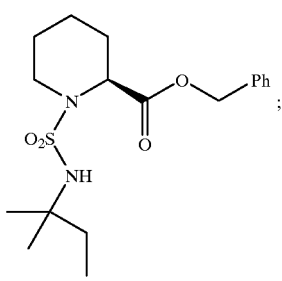 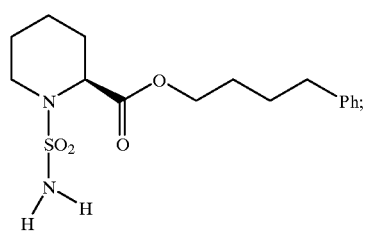
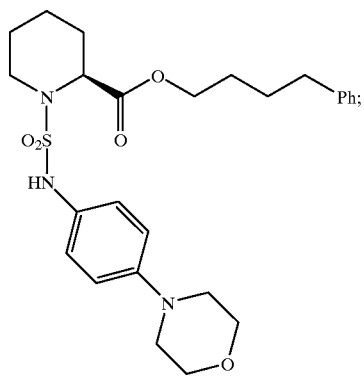 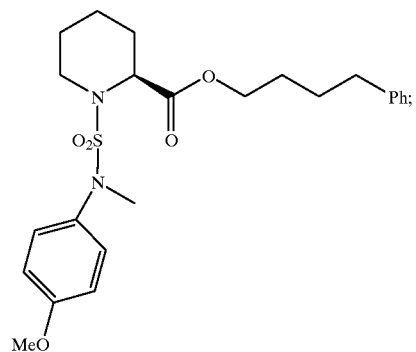
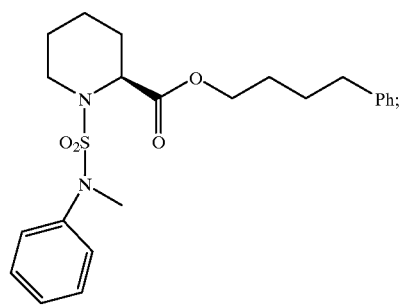 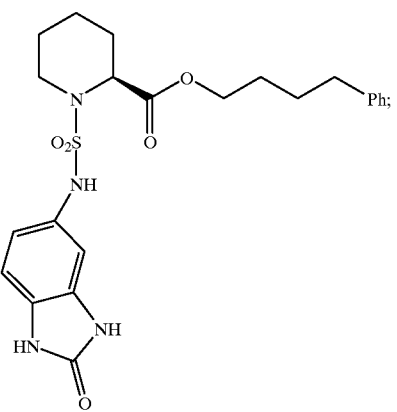

169 170
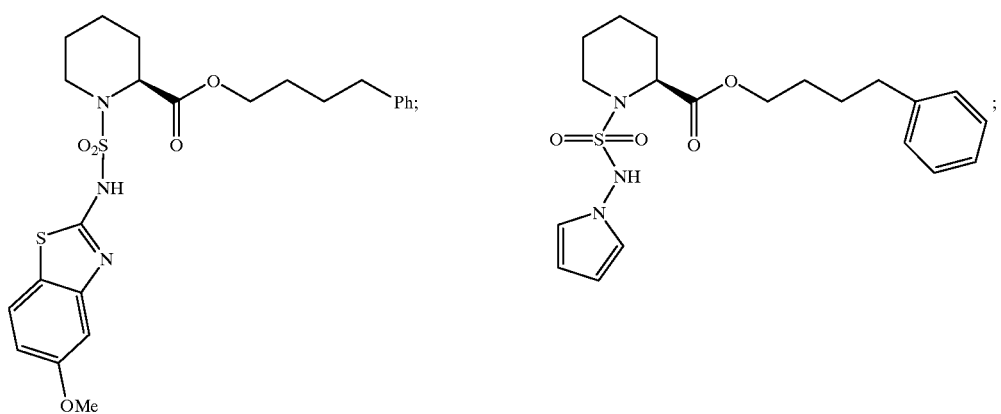
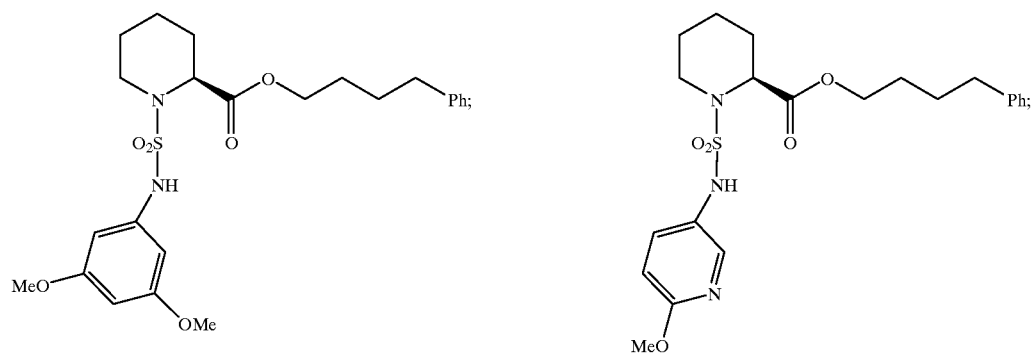
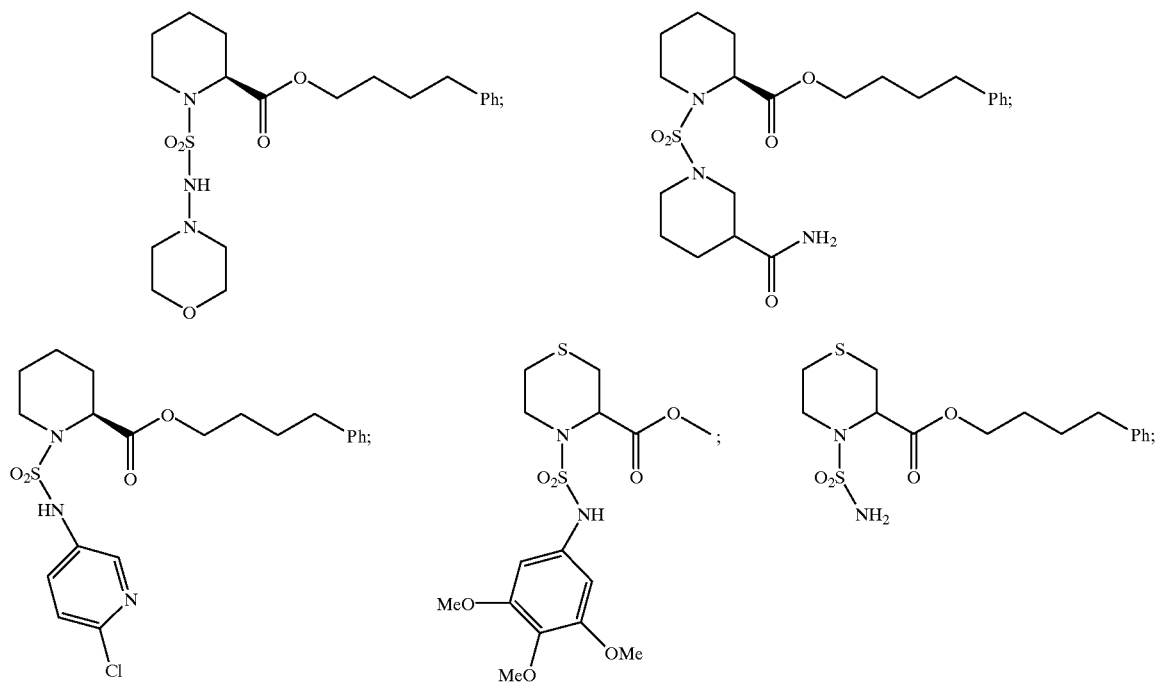

171
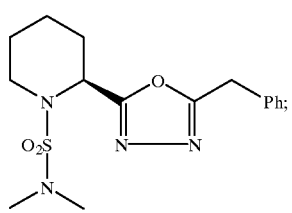
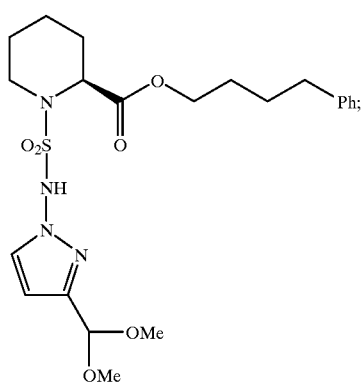
172
-continued
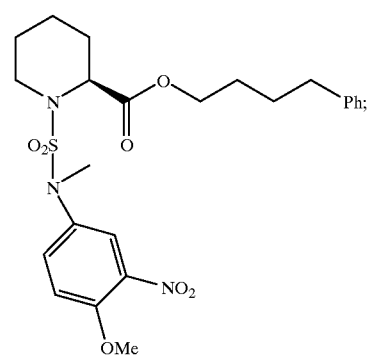
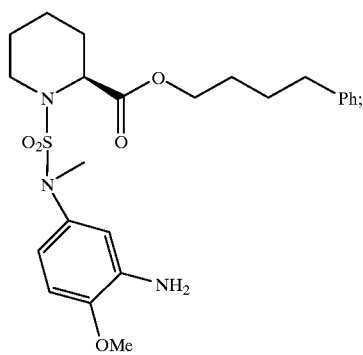
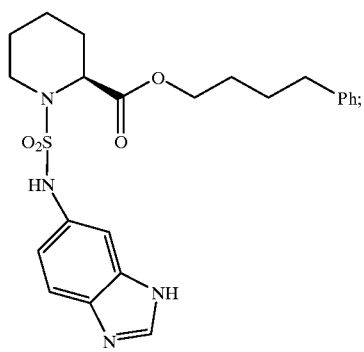
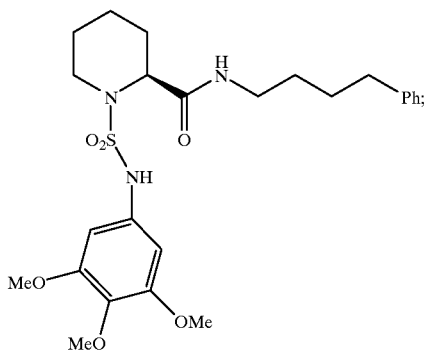
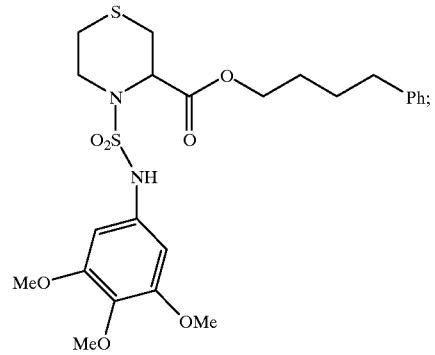
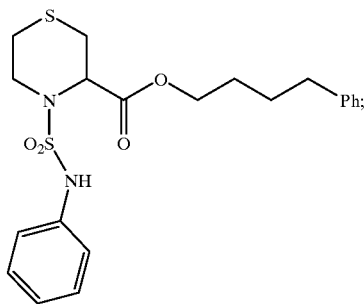
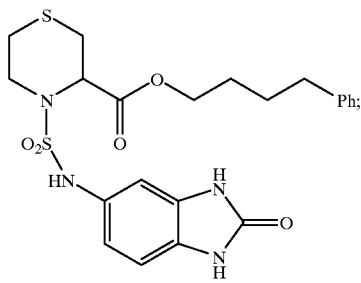

173
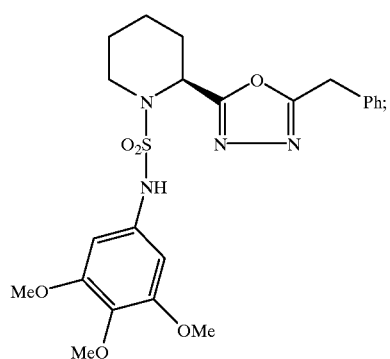
-continued
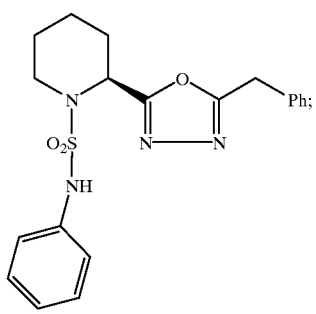
174
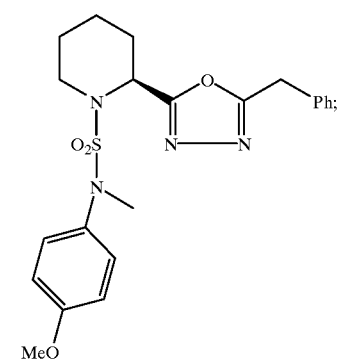
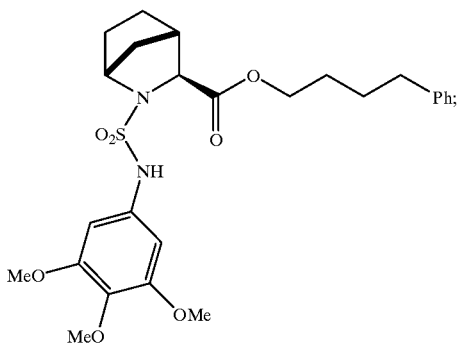
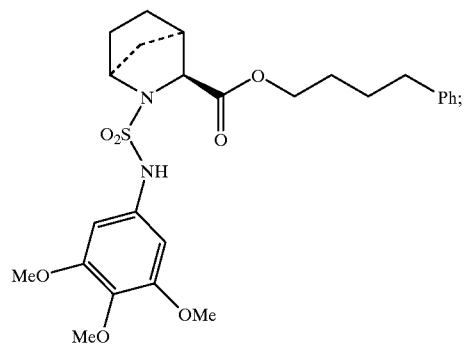
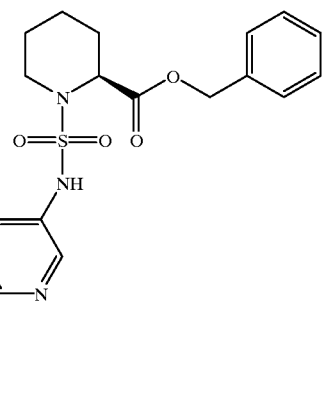
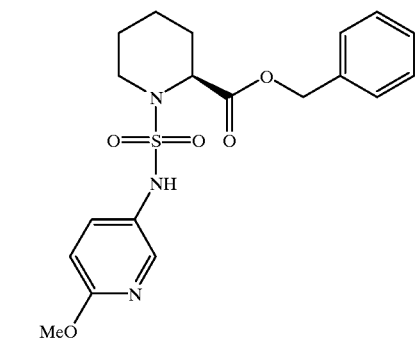
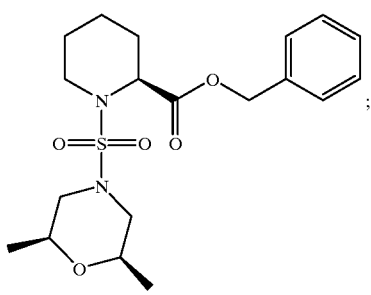
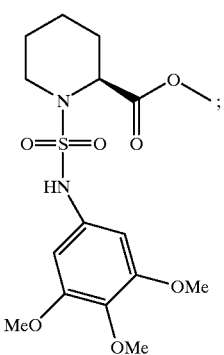
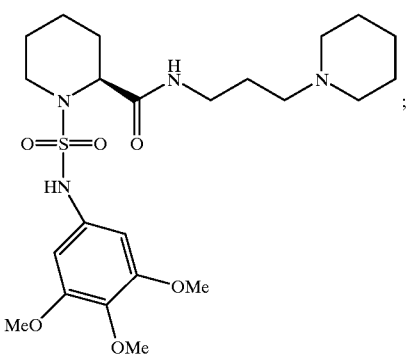

175
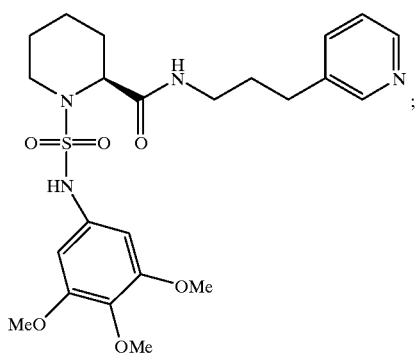
176
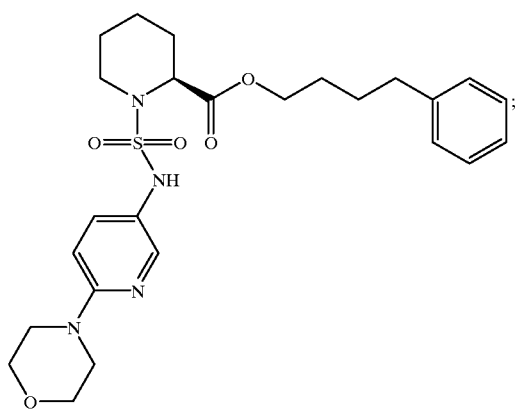
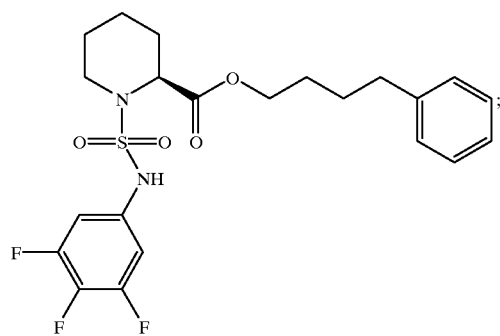
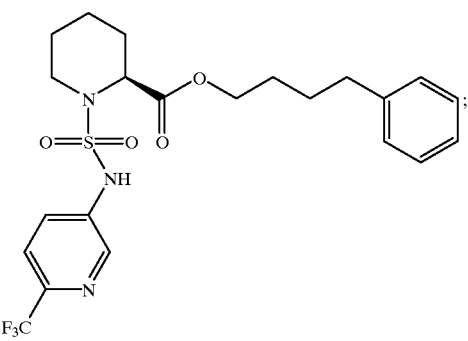
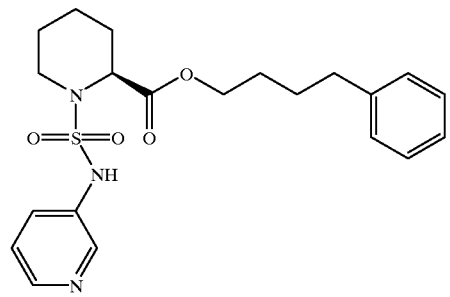
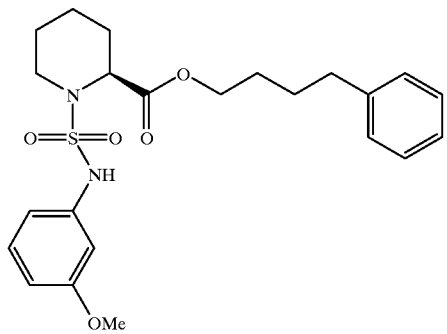
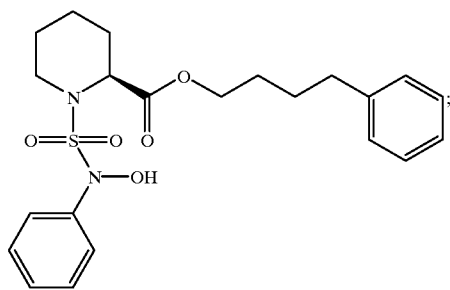
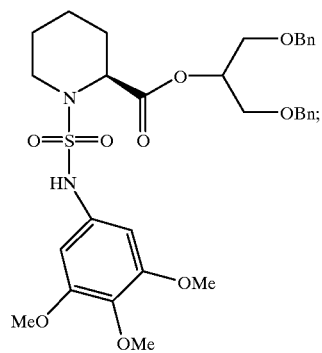 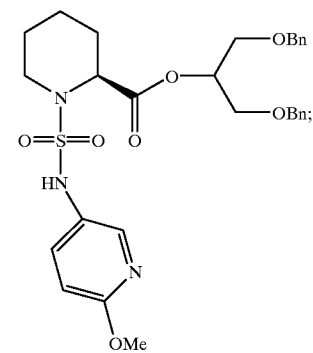

177
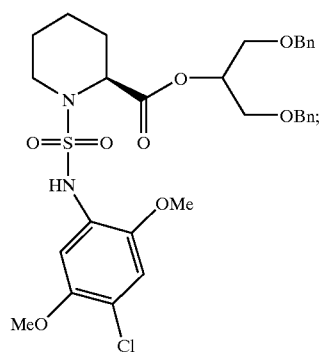
-continued
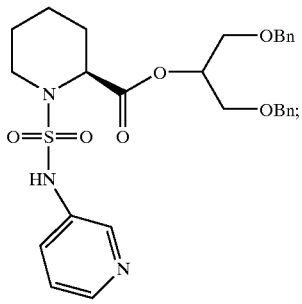
178
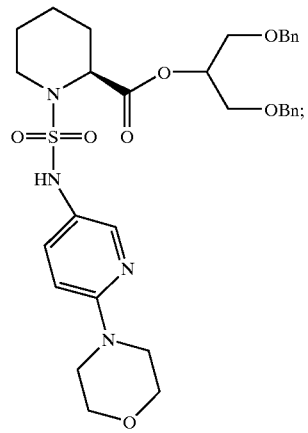
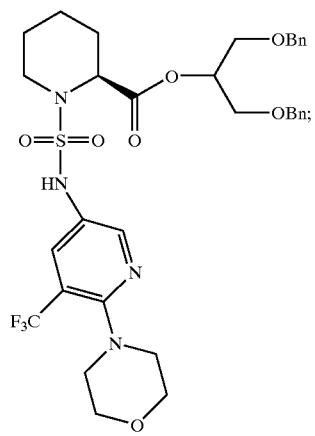
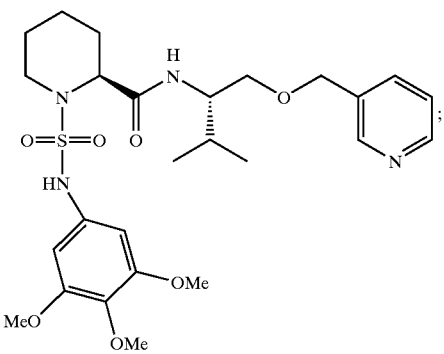
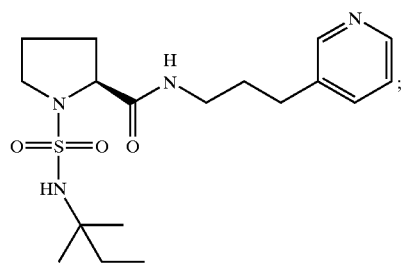
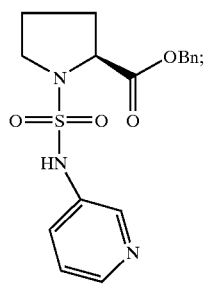
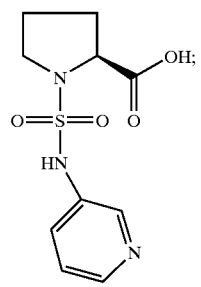
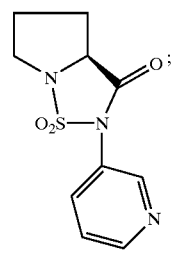
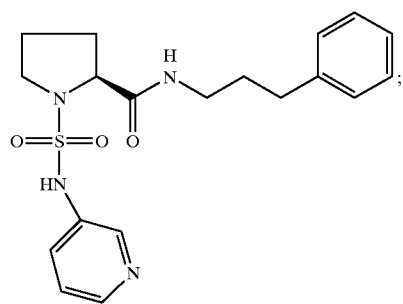
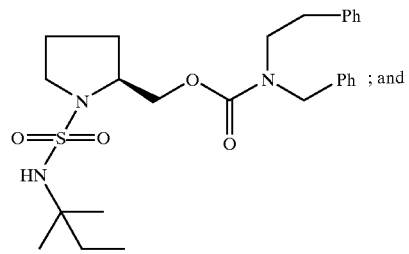

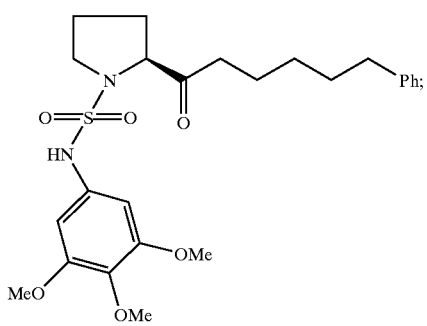

or a pharmaceutically acceptable salt or solvate thereof.

6. A pharmaceutical composition for treating a neurological disorder in a patient comprising a therapeutically effective amount of a compound as claimed in claim 1 and a pharmaceutically acceptable carrier.

7. A pharmaceutical composition according to claim 6, further comprising a neurotrophic factor.

8. A method of treating a neurological disorder in a patient, comprising: administering to the patient a therapeutically effective amount of a compound as claimed in claim 1.

9. A method according to claim 8, wherein the neurological disorder is selected from the group consisting of neuralgias, muscular dystrophy, bell's palsy, myasthenia gravis, Parkinson's disease, Alzheimer's disease, multiple sclerosis, ALS, stroke and ischemia associated with stroke, neural parapathy, other neural degenerative diseases, motor neuron diseases, and nerve injuries including spinal cord injuries.

10. A pharmaceutical composition for treating a neurological disorder in a patient comprising a therapeutically effective amount of a compound as claimed in claim 4 and a pharmaceutically acceptable carrier.

11. A pharmaceutical composition according to claim 10, further comprising a neurotrophic factor.

12. A method of treating a neurological disorder in a patient, comprising: administering to the patient a therapeutically effective amount of a compound as claimed in claim 4.

13. A method according to claim 12, wherein the neurological disorder is selected from the group consisting of neuralgias, muscular dystrophy, bell's palsy, myasthenia gravis, Parkinson's disease, Alzheimer's disease, multiple sclerosis, ALS, stroke and ischemia associated with stroke, neural parapathy, other neural degenerative diseases, motor neuron diseases, and nerve injuries including spinal cord injuries.

14. A compound selected from the group consisting of:

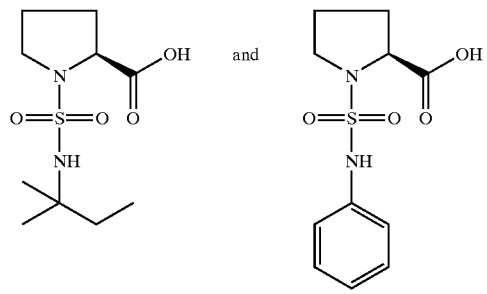

or a pharmaceutically acceptable salt, solvate, prodrug, or pharmaceutically active metabolite thereof.

15. A compound selected from the group consisting of:

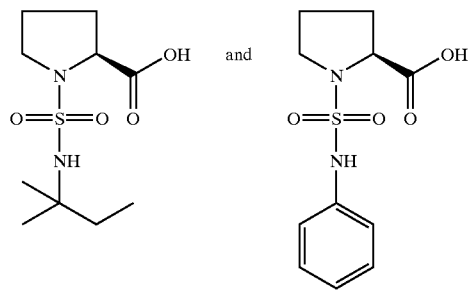

or a pharmaceutically acceptable salt or solvate thereof.

* * * * *